(12) United States Patent
Jones et al.

(10) Patent No.: US 8,367,893 B2
(45) Date of Patent: Feb. 5, 2013

(54) LATE BLIGHT RESISTANCE GENES AND METHODS

(75) Inventors: Jonathan Jones, Norwich (GB); Simon John Foster, Norwich (GB); Zhaohui Chu, Norwich (GB); Tae-Ho Park, Suwon (KR); Edwin Andries Gerard Van Der Vossen, Utrecht (NL); Mathieu Andre Pel, Wageningen (NL); Richard Gerardus Franciscus Visser, Bennekom (NL)

(73) Assignee: Plant Bioscience Limited, Norwich, Norfolk (GB)

( * ) Notice: Subject to any disclaimer, the term of this patent is extended or adjusted under 35 U.S.C. 154(b) by 311 days.

(21) Appl. No.: 12/669,871

(22) PCT Filed: Jul. 18, 2008

(86) PCT No.: PCT/GB2008/002469
§ 371 (c)(1),
(2), (4) Date: Jan. 20, 2010

(87) PCT Pub. No.: WO2009/013468
PCT Pub. Date: Jan. 29, 2009

(65) Prior Publication Data
US 2010/0192257 A1   Jul. 29, 2010

(30) Foreign Application Priority Data
Jul. 20, 2007  (GB) .................................. 0714241.7

(51) Int. Cl.
A01H 5/00   (2006.01)
C12N 15/09  (2006.01)
C12N 15/82  (2006.01)
C12N 15/29  (2006.01)

(52) U.S. Cl. ...... 800/279; 536/23.7; 536/23.1; 435/69.1; 435/468; 800/278; 800/298; 800/317; 800/317.2

(58) Field of Classification Search ........................ None
See application file for complete search history.

(56) References Cited

U.S. PATENT DOCUMENTS
2004/0237137 A1*  11/2004  Osumi et al. .................. 800/279

FOREIGN PATENT DOCUMENTS
EP         1247867 A1    10/2002

OTHER PUBLICATIONS

Franco, J. et al., "Screening for resistance to *Nacobbus aberrans* and *Globodera* spp. in wild potato species resistant to other pathogens," Nematol. Medit. (2006)34:165-169.
Huang, S. et al., "Comparative genomics enabled the isolation of the R3a late blight resistance gene in potato," The Plant Journal (2005) 42:251-261.
Park, T-H. et al., "High resolution mapping and analysis of the resistance locus Rpi-abpt against phytophthora infestans in potato," Molecular Breeding: New Strategies in Plant Improvement (2005) 16(1):33-43.
Park, T-H. et al., "Identification, characterization and high-resolution mapping of resistance genes to phytophthora infestans in potato, Chapter 5—The Late blight resistance locus Rpi-blb3 from solanum bulbocastanum belongs to a major late blight R gene cluster on chromosome 4 of potato," Identification, Characterization and High-Resolution Mapping of Resistance Genes Phytophthora Infestants in Potato (2005) 64-80.
Smilde, W.D. et al., "Solanum mochiquense chromosome IX carries a novel late blight resistance gene Rpi-mocl," Theor. Appl. Genet. (2005) 110:252-258.
Song, J. et al., "Gene RB cloned from solanum bulbocastum confers broad spectrum resistance to potato late blight," Proc. Natl. Acad. Sci. USA (2003) 100(16):9128-9133.
Van Der Vossen, E. et al., "An ancient R gene from the wild potato species solanum bulbocastanum confers broad-spectrum resistance to phytophthora infestans in cultivated potato and tomato," The Plant Journal (2003) 36:867-882.
International Search Report and Written Opinion for Application No. PCT/GB2008/002469 dated Mar. 3, 2009 (15 pages).

* cited by examiner

*Primary Examiner* — Medina A Ibrahim
(74) *Attorney, Agent, or Firm* — Andrus, Sceales, Starke & Sawall, LLP

(57) ABSTRACT

This invention provides novel gene sequences, compositions and methods for enhancing the resistance in crops, in particular but not limited to, potato, to late blight caused by the oomycete pathogen *Phytophthora infestans*.

12 Claims, 22 Drawing Sheets

FIGURE 7

```
                                                                                              SEQ
                                                                                              ID NO
Rpi-oka1   MNYCVYKTWAVDS---------------------YFPFLILFFRKKKFNEELKEMAEILLTAVINKS  :  46         4
Rpi-oka2   ............NTKANSTSFLSFFS...........................................  :  60        12
Tm2-2      -------------------------------------------..........S.....            :  13        14

Rpi-oka1   IEIAGNVLFQESTRLVWLKEDIDWLQREMRHIPSYVDNAKAKEVGGDSRVKNLLKDIQQL            : 106
Rpi-oka2   ............................................................          : 120
Tm2-2      V.....L.I...K.......................A..................E..            :  73

Rpi-oka1   AGDVEDLLDEFLPKIQQSNKFICCLKTVSFADFFAMEIPKIKRRVADIDRVRTTYSITDT            : 166
Rpi-oka2   ............................................................          : 160
Tm2-2      .........D........NY...RS..............V....I,K..N.I..                 : 133

Rpi-oka1   SNNNDDCIPLDRRRLFLHADETEVIGLEDDFNTLQAKLLDHDLPYGVVSIVgmpglgktt            : 226
Rpi-oka2   ............................................................          : 240
Tm2-2      D......VL.............I....D....M......NQ..H................           : 193

Rpi-oka1   laKRLYRHVCHQFECSGLVYVSQQPRAGETLHDIAKQVGLTEEERKENLENNLRSLLKIK           : 286
Rpi-oka2   ............................................................          : 300
Tm2-2      ......LIRD..........S...L......I...QKM.....D..........                 : 253

Rpi-oka1   ryvilldd1wDVEIWDDIKLVLPECDSKIGSRIIITSRNSNVGRYIGGDFSIHVLQPLDS           : 346
Rpi-oka2   ............................................................          : 360
Tm2-2      ...F..................V...............ES.L.A....E.                    : 313

Rpi-oka1   ERSFELFTKKIFNFVNDN--WANASPDLVNIGRCIVERCGqiplaivvtagMLRARGRTEH          : 405
Rpi-oka2   ..................V.......................                             : 419
Tm2-2      .............DDN.S...........N..G....................E....            : 373

Rpi-oka1   AWNRVLESMAHKIQDGCGEVLALSYNDLPIALrpcflyfglYPEDHEIRAFDLTNMWIAE           : 465
Rpi-oka2   ............................................................          : 479
Tm2-2      ........G..V....A..............S...............I......                : 433

Rpi-oka1   KLIVVNTGNGREAESLADDVLNDLVSRNLIQVAKRTYDGRISSCRIHDLLHSLCVDLAKE           : 525
Rpi-oka2   ............................................................          : 539
Tm2-2      .F....S..R....D..E............L.....N..................                : 493

<------------------------------><-------------------
Rpi-oka1   SNFHTERNAFGDFSNVARVPRITFYSDDNAMNEFFHLNFKFMKLRSLFCFTKDRCIFSQ            : 585
Rpi-oka2   ........Y...................................................          : 599
Tm2-2      ......A.D.....G....L........N-V.I...RS...LE...V....A..PS...H          : 552

-><----------------------------><-------------------------><--------
Rpi-oka1   MAHLNFKLLQVLVVVMSQKGYQHVTFPKKIGNMSCLRYVRLEGAIRVKLPNSIVKLKCLE           : 645
Rpi-oka2   ............................................................          : 659
Tm2-2      ..YFD....RT.......SFQAY..I.S.F...T....L....N.CG.........TR..          : 612

----------------------><-----------------------------><------------
Rpi-oka1   TLDIFHSSSK-LFFGVWESKILRHLCY-------TEECYCVSFAS?FCRIMPPNNLQTLMW          : 698
Rpi-oka2   ............-----....................                                  : 712
Tm2-2      .I..DRR.LIQP.S......H......RDYGQACNE.FSI.SFY.NIYSLH.........           : 672

----------><-----------------><----------------------------><
Rpi-oka1   VDDKFCEPRLLHRLINLRTLCIMDVSGSTIKILSALSPVPRALEVLKLRFFKNTSEQINL          : 758
Rpi-oka2   .........................................K.................          : 772
Tm2-2      IF....F..........K.G.LG..N..V.M..IF...LK.......S.SSDP....K.           : 732

-------------><-----------------------><
Rpi-oka1   SSHFNIVELGLVGPSAMLLNIEAFPPNLVKLNLYGLMVDGHLLAVLKKLPKLRILILLWC           : 818
```

Figure 7 (continued)

```
Rpi-oka2  ..........................................  : 832
Tm2-2     ..Y.H.AK.H.NVNRT.A..SQS.....I..TLANFT..RYI.....TF....K.KMFI. : 792

-------------><------------------------><-----------------------
Rpi-oka1  RHDAEKMDLSGDS----FPQLEVLYIEDAQGLSBVTCMDDMSMFKLKKLFLVQGPNISPI : 874
Rpi-oka2  ............................................................ : 888
Tm2-2     KYNE.......EANGYS.......HIMSPN.......T..V.........L.TG-----FHC : 848

><---------------->
Rpi-oka1  SLRVSERLAKLRISQVL : 891
Rpi-oka2  ................. : 905
Tm2-2     RISL....K..SK----- : 861
```

FIGURE 8

```
                                                                              SEQ ID NO
  1 MRYCVYETWAVDSNTFANSTSFLSSFSYFPELILTFRKKKFNEELKEMAEILLTAVIRKS  Rpi-nrs1      16
  1 ................--------------.............................  Rpi-oka1       4
  1 --------------------------------------------------......S...  Tm2²          15

61 IEIBGNVLFQEGTRLYWLKEDIDWLQREMRHIRSTVDHAKAKEVGDSFVKRLLEDIQQL  Rpi-nrs1
 47 ...........................................................  Rpi-oka1
 14 V.....L.I...K.............................A...............E.  Tm2²

121 AGDVEDLLDEFLPKIQQSNKFICCLFTVSFADEFAMEIEKIKPRVADIDRVRTTYSIEDT  Rpi-nrs1
107 ...........................................................  Rpi-oka1
 74 .........D.......NY...RS..................V....T.K..N.⁻..  Tm2²

181 SHDNDDCIPLDRRPLFLEADSTEVIGLREDFNTLQAFILEDHELFVGVVSIVKMACLSKYT  Rpi-nrs1
167 ...........................................................  Rpi-oka1
134 D......VL............I...D....M......NQ..H.................  Tm2²

241 LAEKLYEEVCEQFECSOLVYVSQQPRAOEYLHDIAEQVGLTEEEPKERLENNLRSLLKIE  Rpi-nrs1
227 ...........................................................  Rpi-oka1
194 .......LIRD................S...L.....I....QKM.....D.........  Tm2²

301 PYVIALGGIKDVEIRDGAFLVLPETGSKIGSEIIITSPNSRVGPYIGGEFSEEVIQELDS  Rpi-nrs1
287 ...........................................................  Rpi-oka1
254 ...F....V...................V................ES.L.A....E.   Tm2²

361 EKSFELETEKIPNEVNGE-WANASEDLVRICPCIVERCCKIFLAIVYTACWIRAFGEIEE  Rpi-nrs1
347 ...............-...........................................  Rpi-oka1
314 .............DDN.S.................N..G...................E.  Tm2²

420 AMPRVLEEMAHNIQDEOGKVLADSFRGLFIALAPCFAFFXIFPEDHEIRAPDLENNWIAE  Rpi-nrs1
406 ...........................................................  Rpi-oka1
374 .........G..V....A.............S.....................I.....  Tm2²

480 KLIVVNTGNCFEAESLAGDVIRDLVSRNLIQVRPRCYLGRISSCPIEDLLESLCVDLAFE  Rpi-nrs1
466 ...........................................................  Rpi-oka1
434 .F....S..R....D..E.............L.....N.....................  Tm2²

540 SNFFETEEYASGDESFVARVFRITEYSLGRAHMEPFHLMEFEMFLASLPCETFEPCIFSQ  Rpi-nrs1
526 ........N..................................................  Rpi-oka1
494 ......A.D.....G....L........-..V.I...RS...LE...V....A..PS...H  Tm2²

600 HAHLNFKLLQVLVVVMSQKCXQEVTFEKEICRMSCLRYELECAIPVKLPNGIVPLECLE  Rpi-nrs1
586 ...........................................................  Rpi-oka1
553 ..YFD....HT........SFQAY...I.S.F...T....L.....N.CG........TR..  Tm2²

660 TLEIFSESSKLE-FGVWEESFILRMLCY------TEECYCVSFASPFCPIMPENNLQTLMN  Rpi-nrs1
646 .....-.........------......................................  Rpi-oka1
613 .I..DRR.LIQ.PS......H......RDYGQACNS.FSI.SFY.NIYSLH.........  Tm2²

713 VEDKPCEPRLLHRLIHLRTLCIRGV3GSTIFILSALSEVPKALEVLKLRFFKNESEQIRL  Rpi-nrs1
699 ..........................................R...............  Rpi-oka1
673 IP...F..............K.G.LG..N..V.M..IF...L........S.SSDP....K.  Tm2²

773 SSEFPIVELGLVGESAMLINIEAPPSRLVELNLVGLMVDGHLLAVLEKLPKLPILHLLNC  Rpi-nrs1
759 ...........................................................  Rpi-oka1
733 ..Y.H.AK.H.NVNRT.A..SQS......I..T.ANFT..RYI......TF....K.KMFI.  Tm2²

833 PEGAEKNDLSGDS----FPQLEVLYIEGAQGLSEVTKMEKASMPNLFKLFLVQGPNISFI  Rpi-nrs1
819 ...........----............................................  Rpi-oka1
793 KYNE...A...EANGYS........H.HSPN.......T..V.........L.T-.--FH-C  Tm2²

889 SLPVSERLAKLRISQVL  Rpi-nrs1
875 .................  Rpi-oka1
849 GISL....K..SK      Tm2²
```

FIGURE 12

SEQUENCE LISTING

SEQ. ID. 1 = NUCLEIC ACID SEQUENCE OF Rpi-oka1

```
   1 atgaattatt gtgtttacaa gacttgggcc gttgactctt actttccctt cctcatcctc
  61 acatttagaa aaaagaaatt taacgaaaaa ttaaaggaga tggctgaaat tcttctcaca
 121 gcagtcatca ataatcaatt agaaatagtt ggaaatgtac tctttcaaga aggtacgcgt
 181 ttatattggt tgaaagagga catcgattgg ctccagagaa aaatgagaca cattcgatca
 241 tatgtagaca atgcaaagcc aaaggaagtt ggagcgatt caggggtgaa aaacttatta
 301 aaagatattc aacaactggc aggtgatgtg gaggatctat tagatgagtt tcttccaaaa
 361 attcaacaat ccaataagtt catttgttgc cttaagacgg tttcttttgc cgatgagttt
 421 gctatggaga ttgagaagat aaaaagaaga gttgctgata ttgaccgtgt aaggacaact
 481 tacagcatca cagatacaag taccaataat gatgattgca ttccattgga ccggagaaga
 541 ttgttccttc atgctgatga aacagaggtc atcggtctga aagatgactt caatacacta
 601 caagccaaat tacttgatca tgatttgcct tatgagtg ttcaatagt tggcatgcc
 661 ggtttgggaa aaacaactgc tgccaagaaa cttatagga atgtctgtca tcaatttgag
 721 tgttcgggac tggtctatgt tcacaacag ccaagggcg gagaaatctt acatgacata
 781 gccaaacaag ttggactgac ggaagaggaa aggaagaaa acttgagaa caacctacga
 841 tcactcttga aaataaaaag gtatgttatt ctcttagatg acatttggga tgttgaaatt
 901 tgggatgatc taaaacttgt cctcctgaa tgtgattcaa aaattggcag taggataatt
 961 ataacctctc gaaatagtaa tgtaggcaga tacataggag gggatttctc aatccacgtg
1021 ttgcaacccc tagattcaga gaaagcttt gaactcttta ccaagaaat ctttaattt
1081 gttaatgata attgggccaa tgcttcacca gacttggtaa atatggtag atgtatagtt
1141 gagagatgtg gaggtatacc gctagcaatt gtggtgactg caggcatgtt aagggcaaga
1201 ggaagaacag aacatgcatg gaacagagta cttgagagta tggctcataa aattcaagt
1261 ggatgtggta aggtattggc tctgagttac aatgattgc ccattgcatt aaggccatgt
1321 ttctttgtact ttggtctta cccgaggac catgaaattc gtgcttttga tttgacaat
1381 atgtggattg ctgagaagc gatagttgta aatactggca atgggcgaga ggctgaaagt
1441 ttggcggatg atgtcctaaa tgatttggtt tcaagaaact tgattcaagt tgccaaaagg
1501 acatatgatg gaagattttc aagttgtcgc atacatgact tgttacatgt tttgtgtgtg
1561 gacttggcta aggaaagtaa cttcttcac acggagcaca atgcatttgg tgatcctagc
1621 aatgttgcta gggtgcgaag gattacattc tactctgatg ataatgccat gaatgagttc
1681 ttccatttaa atcctaagcc tatgaagctt cgttcacttt tctgtttcac aaaagaccgt
1741 tgcatatttt ctcaaattgc tcatcttaac ttcaaattac tgcaagtgtt ggttgtagtc
1801 atgtctcaaa agggttatca gcatgttact ttccccaaaa aaattgggaa catgagttgc
1861 ctacgttatg tgcgattgga ggggcaatt agagtaaaat tgccaaatag tattgtcaag
1921 ctcaaatgtc tagagaccct ggatatattt catagctcta gtaaacttcc ttttggtgtt
1981 tgggagtcta aaatattgag acatacttgt tacacagagg aatgttactg tgtctctttt
2041 gcaagtccat tttgcgaat catgcctcct aatatctcac asacttgat gtgggtggat
2101 gataaatttt gtgaaccaag attgttgcac cgattgatsa attaagaac attgtgtata
2161 atggatgtat ccggttctac cattaagata ttatcagcat tgagccctgt gcctagagcg
2221 ttggaggttc tgaagctcag atttttcaag aacacgagtg agcaaataaa cttgtcgtcc
2281 catccaaata ttgtcgagtt gggtttggtt ggtttctcag caatgctctt gaacattgaa
2341 gcattcccta caaatcttgt caagcttaat cttgtcggct tgatggtaga cggtcatcta
2401 ttggcagtgc ttaagaaatt gcccaaatta aggatactta tattgcttg gtgcagacat
2461 gatgcagaaa aaatggatcc ctctggtgat agcttccgc aacttgaagt tttgtatatt
2521 gaggatgcac aagggttgtc tgaagtaacg tgcatggatg atatgagtat gcctaaattg
2581 aaaagctat ttcttgtaca aggcccaaac atttcccaa ttagtctcag gtctcggaa
2641 cggcttgcaa agttgagaat atcacaggta ctataa
```

SEQ. ID. 7 = NUCLEIC ACID SEQUENCE OF Rpi-oka2

```
   1 atgaattatt gtgtttacaa gacttgggcc gttgactcta acactaaagc aaatagtaca
  61 tctttcttat ccttttctc ttactttccc ttcctcatcc tcaatttag aaaaagaaa
 121 ttcaacgaaa aattaaagga gatggctgaa attcttctca cagcagtcat caataaatcc
 181 ataaaatag ctggaaatgt actctttcaa gaaggtacgc gtttatattg gttgaaagag
 241 gacatcgatt ggctccagag agaaatgaga cacattcgat catatgtaga caatgcaaag
 301 gcaaaggaag ttggaggcga ttcaaggtg aaaacttat aaaagatat tcaacaactg
 361 gcaggtgatg tggaggatct attagatgag tttcttccaa aaattcaaca atccaataag
 421 ttcatttgtt gccttaagac ggtttcttt gctgatgagt ttgctatgga gattgagaag
 481 ataaaaagaa gagttgctga tattgaccgt gtaaggacaa cttacagcat cacagataca
 541 agtaacaata tgatgattg cattccattg gaccggagaa gattgttcct tcatgctgat
 601 gaaacagagg tcatcggtct ggaagatgac ttcaatacac tacaagccaa attacttgat
 661 catgatttgc cttatgagt tgtttcaata gttggcatgc ccggtttggg aaaaacaact
 721 cttgccaaga aacttatagg aatgtctgt catcaatttg agtgttcatg tgtggtctat
 781 gttcacaacag ccaagggc gggagaaatc ttacatgaca tagccaaaca agttggactg
 841 acggaagagg aaaggaaga aaacttggag aacaacctac gatcactctt gaaataaaa
 901 aggtatgtta ttctcttaga tgacatttgg gatgttgaaa ttgggatga tctaaaactt
 961 gtccttcctg aatgtgattc aaaaattggc agtaggataa ttataacctc tcgaaatagt
1021 aatgtaggca gatacatagg aggggatttc tcaatccacg tgttgcaacc cctagattca
1081 gagaaagctt tgaactcttt accaagaaa tcttttaatt ttgctaatga taattgggcc
1141 aatgcttcac cagacttggt aaatatggt agatgtatag ttgagagtg tggaggtata
1201 ccgctagcaa ttgtggtgac tgcaggcatg ttaagggcaa gaggaagaac agaacatgca
```

Figure 12 (continued)

```
1261 tggaacagag tacttgagag tatggctcat aaaattcaag atggatgtgg taaggtattg
1321 gctctgagtt acaatgattt gcccattgca ttaaggccat gtttcttgta ctttggtctt
1381 tacccgagg accatgaaat tcgtgtttt gatttgacaa atatgtggat tgctgagaag
1441 ctgatagttg taaatactgg caatgggcga gaggctgaaa gtttggcgga tgatgtccta
1501 aatgatttgg ttcaagaaa cttgattcaa gttgccaaaa ggacatatga tggaagaatt
1561 tcaagtgtc gcatacatga cttgttacat agtttgtgtg tggacttggc taaggaaact
1621 aacttcttc acacggagca ctatgcattt ggtgatccta gcaatgttgc tagggtgcga
1681 aggattacat tctactctga tgatgatgcc atgaatgagt tcttccattt aaatcctaag
1741 cctatgaagc ttcgttcact tttctgtttc acaaaagacc gttgcatatt ttctcaaatg
1801 gctcatctta acttcaaatt attgcaagtg ttggttgtag tcatgtctca aaagggttat
1861 cagcatgtta cttcccaa aaaattggg aacatgagtt gctacgcta tgtgcgattg
1921 gaggggcaa ttagagtaaa attgccaaat agtattgtca agctcaaatg tctagagacc
1981 ctggatatat ttcatagctc tagtaaactt cctttgtg ttgggagtc taaaatattg
2041 agacatcttt gttacacaga agaatgtac tgtgtctctt ttgcaagtcc attttgccga
2101 atcatgcctc ctaataatct acaaacttg atgtggtgg atgataaatt ttgtgaacca
2161 agattgttgc accgattgat aaatttaaga acattgtgta taatggatgt atccgttct
2221 accattaaga tattatcagc attgagccct gtgcctaaag cgttggaggt tctgaagctc
2281 agattttca agaacacgag tgagcaata ccattgtgt cccatccaaa tattgtcgag
2341 tgggttgg ttgtttctc agcaatgctc ttgaacattg aagcattccc tccaaatctt
2401 gtcaagctta atcttgtcgg cttgatggta gacggtcatc tattggcagt gcttaagaaa
2461 ttgcccaaat taaggatact tatattgctt tggtgcagac atgatgcaga aaaatggat
2521 ctctctggtg atagctttc gcaacttgaa gtttgtata ttgaggatgc acaagggttg
2581 tctgaagtaa cgtgcatgga tgatatgagt atgcctasat tgaaaagct attctttgta
2641 caaggccaa acatttccc aattagtctc agggtctgg aacggcttgc aaagttgaga
2701 atatcacagg tactataa
```

SEQ. ID. 8 = NUCLEIC ACID SEQUENCE OF *Rpi-oka1* TRANSGENE FROM PSLJ21152
(INCLUDES OWN PROMOTER AND TERMINATOR)

```
   1 agttatacac cctacattct actcgagtca ttatgatgat gtctcacgac caaatcaaat
  61 caaagttaaa taaatatcga acgaacgcc cactctgtat gagtatggca aaagatttg
 121 agagaatcaa gttgcataaa agcctaattt tcatggaaca tacaaattga gtctcataat
 181 agcccaaact cacagccatg aaccaaatt gggtaaagtt ttgcaagacg ttcatcaaac
 241 agttaggaaa catasaatgg cgctagatat ataataaatt ttttaacat atggtgtgat
 301 tgatagttat atactaaaga tgttttgctta gttacgtaat tttttcaaaa aaaaaggta
 361 cattatcaat catcagtcac aaaatattaa aagttactgt ttgtttttta aattccatgt
 421 cgaatttaat tgaatgacac ttaaattggg acgaacggtg taatttcttt tgactattct
 481 actagtatct atccacagca cgtgttgttc cttcttctt tcgttttca tttacttgac
 541 attattagga gacttggcc tgaactccaa ctattctaag ctgacctttc ttttccttta
 601 ccaattatct tcttctttct aatttcgttt tacgcgtagt actgcctgaa tttctgact
 661 ctcaacgttt gttattcatg cttgaaacg aaataccagc taccaaaga tgaattattg
 721 tgtttacaag acttgggcg ttgactctta cttccctc ctcatcctca cattagaaa
 781 aaagaaattt aacgaaaat taaggagat ggctgaaatt cttctcacag cagtcatcaa
 841 taaatcaata gaaatagctg gaaatgtact ctttcaagaa ggtacgcgtt tatattggtt
 901 gaaagacgac atcgattggc tccagagaga atgagacac attcgatcat atgtagacaa
 961 tgcaaacgca aggaagttg gagcgattcc aagggtgaaa aacttattaa aagatattca
1021 acaactggca ggtgatgtgg aggatctatt agatgagttt cttccaaaaa ttcaacaatc
1081 caataagtc atttgttgcc ttaagacggt ttctttgcc gatgagtttg ctatggagat
1141 tgaacagata aaaagaagag ttgctgaatt tgaacgtgta aggacaactt acagcatcac
1201 agatacaagt aacaataatg atgattgcat tccattggac cggagaagat tgttccttca
1261 tgctgatgaa acagaggtca tcggtctgga agatgactc aatacactac aagccaaatt
1321 acttgatcat gatttgcctt atggagttgt ttcaatagtt ggcatgccg gtttgggaaa
1381 aacaactctt gccagaaac tttataggca tgtctgtcat caattgagt gttcgggact
1441 ggtctatgtt tcacaacagc caagggcggg agaaatctta catgacatag ccaaacaagt
1501 tggactgacg gaagaggaaa ggaaagaaaa cttggagaac aacctacgat cactcttgaa
1561 aataaaaagg tatgttattc tcttagatga cattgggat gttgaaattc gggatgtct
1621 aaaacttgtc cttcctgaat gtgattcaaa aattgcagt aggataatta taccctctg
1681 aaatagtaat gtaggcagat acataggagg ggatttctca atccacgtgt tgcaaccct
1741 agattcagag aaaagctttg aactctttac caagaaaatc tttaattttg tcaatgataa
1801 ttgggccaat gcttccacag acttggtaaa tattggtaga tgtatagttg agagatgtgg
1861 aggtatacg ctagcaattg tggtgactgc aggcatgtta agggcaagag aagaacaga
1921 acatgcatgg aacagagtac ttgagagtat ggctcataaa attcaagatg gatgtgtaa
1981 ggtattggct ctgagttaca atgatttgcc cattgcatta agccatgtta tcttgtactt
2041 tggtctttac cccgaggacc atgaaattgc tgtttttgat ttgat ttgacaaata tgtgattgc
2101 tgagaagctg atagttgtaa atactggcaa tgggcgagag gctgaaagtt tggcggatga
2161 tgtcctaaat gatttggttt caagaaactt gattcaagtt gccaaaagga catatgatgg
```

Figure 12 (continued)

```
2221 aagaatttca agttgtcgca tacatgactt gttacatagt ttgtgtgtgg acttggctaa
2281 ggaaagtaac ttcttccaca cggagcacaa tgcatttggt gatcctagca atgttgctag
2341 ggtgcgaagg attacattct actctgatga taatgccatg aatgagttct tccatttaaa
2401 tcctaagcct atgaagcttc gttcacttt ctgtttcaca aaagaccgtt gcatatttc
2461 tcaaatggct catcttaact tcaaattatt gcaagtgttg gttgtagtca tgtctcaaaa
2521 gggttatcag catgttactt tccccaaaaa aattgggaac atgagttgcc tacgttatgt
2581 gcgattggag ggggcaatta gagtaaaatt gccaaatagt attgtcaagc tcaaatgtct
2641 agagacctg gatatatttc atagctctag taaacttcct tttggtgttt gggagtctaa
2701 aatattgaga catctttgtt acacagaaga atgttactgt gtctctttg caagtccatt
2761 ttgccgaatc atgcctccta ataatctaca aactttgatg tgggtggatg ataaattttg
2821 tgaaccaaga ttgttgcacc gattgataaa tttaagaaca ttgtgtataa tggatgtatc
2861 cggttctacc attaagatat tatcagcatt gagccctgtg cctagagcgt tggaggttct
2941 gaagctcaga ttttcaaga acacgagtga gcaaataaac ttgtcgtccc atccaaatat
3001 tgtcgagttg ggtttggttg gttctcagc aatgctcttg aacattgaag cattccctcc
3061 aaatcttgtc aagcttaatc ttgtcggctt gatggtagac ggtcatctat tggcagtgct
3121 taagaaattg cccaaattaa ggatacttat attgctttgg tgcagacatg atgcagaaaa
3181 aatggatctc tctggtgata gcttccgca acttgaagtt ttgtatattg aggatgcaca
3241 agggttgtct gaagtaacgt gcatggatga tatgagtatg cctaaattga aaagctatt
3301 tcttgtacaa ggcccaaaca tttccccaat tagtctcagg gtctcggaac ggcttgcaaa
3361 gttgagaata tcacaggtac tataaataat tatttacgtt taatatcctat gattttttta
3421 aatttgtatt tagttcatca actaaatatt ccatgtctaa taaattgcag ggatgccttt
3481 gaaaatgatt ctgtgttgga gagaatcttc tgatgcctgt tggtattata atactaataa
3541 taagagaaaa agtttgatta ctgtttcaag ttaattgctt gtgatttgta aaaacaaatt
3601 acttttatat ttctctttgt tttattttat gttattttat cttctaattaa tggagtaata
3661 aaataaaaat cttatttca atagaaaaaa gtagacctta tttgtggtgc atgtatggta
3721 tctttttgaa attttgata tatttgctct ttgattcgaa tttcttgctt atatgatgat
3781 ttgcataaat ataaaatatt atacaaatac ctatgggttg gaaaatatag aaatatgcca
3841 atcaaatgta tacaaaaatc attaatagat agaatcgtaa aagatataca aatgagaaat
3901 gcttgactaa gaagcttgt gcaacctctc acactgagca caatgcattt ggtgatctcg
3961 gcactattgc tgttacttgt aagactacgt tccccaataa gtctttccaa acggcttgca
4021 aagctgagaa tatgaaaatc tcataggtta gtttgctgcg ttaattattt acatttaata
4081 tgctcgtaa ggtgattta aaaaatttg tactagttaa ttcatgaact aaatatttca
4141 tttaatactc cataattcltg aatatggaaa atsaataata tttaataaca agaataaaat
4201 gataaattat tcattgattt tataaattgg atsaatatta ttaaatattc ttaaataata
4261 taatgaacaa gtgaagatga acggagggag tatgaagcct ctttcaaag
```

SEQ. ID. 2 = NUCLEIC ACID SEQUENCE OF *Rpi-mcq1.1*

```
   1 atgctgaaa ttcttcttac agcagtcatc aatsaatctg tagaaatagc tggaaatgta
  61 ctcttcaag aaggtacgcg ttatattgg ttgaaggagg atatagattg gctccaaaga
 121 gaaatgagac acattcgatc atatgtagac aatgcaaagg ccaaggaagt tggaggtgat
 181 tcaagggtga aaaacttatt aaaagatatt caacaactcg caggtgatgt ggaggatctc
 241 ctagatgagt ttcttccaaa aattcaacaa tccagtaagt tcaaaggcgc aatttgttgc
 301 cttaagaccg ttttctttgc ggatgagttt gctatggaga ttgagaagat aaaagaagg
 361 gttgtggaca ttgatcgtgt aaggacaact tacaacatca tggatacaaa taacaacaat
 421 gattgcattc cattggacca gagaagattg ttccttcatg ttgatgaaac agaggtcatc
 481 ggtttggatg atgacttcaa tacactacaa gccaaattac ttgaccaaga ttgccttat
 541 gggttgttt caatagttgg catgcccgt ctaggaaaaa caactcttgc caagaaactt
 601 tataggcatg tccgtcataa atttgagtgt tcgggactgg tctatgtttc acaacagcca
 661 agggcgggag aaatcttaat cgacatagcc aaacaagttg gactgacgga agacgaaagg
 721 aaagaaaact tggagaacaa cctacggtca ctcttgaaaa gaaaaaggta tgttattctc
 781 ttagatgaca tttgggatgt tgaaatttgg gatgatctaa aacttgcct tcctgaaagc
 841 gattcaaaaa ttggcagtag gataattata acctctcgaa atagtaatgt aggcagatac
 901 ataggagggg attttcaat tcacgtgttg caacctctaa attcggagaa cagttttgaa
 961 ctctttaccca agaaaatctt tatttttgat aacaataata attggaccaa tgcttcacca
1021 aacttggtag atattggtag aagtaragtt ggtagatgtg gtggtatacc actagccatt
1081 gtgtgactg caggcatgtt aagggcaaga gaaagaacga aacgtgcatg gaacaggtta
1141 cttgagagta tgagccataa agttccagat ggatgtgcta aggtattggc tctgagttac
1201 aatgatttgc caattgcatt aaggccatgt ttcttgtatt tggccttta cccgaggat
1261 catgaaattc gtgcttttga tttgacaaat atgtggattg ctgagaagtt gatagttgta
1321 aatagtggca atggcgaga ggctgaaagt ttggccgaaagt atgtcctaaa tgatttgtt
1381 tcaagaaaca tgattcaagt tgccaaaagg acatatgatg gaagaattc aagttgtcgc
1441 atacatgct tgttacatag tttgtgtgtt gacttggcta aggaaagcaa cttctttcac
1501 acgagcaca atgcattggg tgatccgga aatgttgcta ggctgcgaag gattacattc
1561 tactctgata atgatgccat gaatgagttc ttccttaagcc tgaaagcett
1621 cgtgcacttt tctgttttac agaagaccct tgcatatttt ctcaactggc tcatcttgat
1681 ttcaaattat tgcaagtgtt ggttgtagtc atctttgttg atgatatttg tgtgtcagt
1741 atcccaaaca catttgggaa catgaggtgc ttacgttatc tggattcca ggggcatttt
1801 tatgggaaac tgccaaattg tatggtgaag ctcaaacgtc tagagaccct cgatattggt
```

Figure 12 (continued)

```
1861 tatagcttaa ttaaattttcc tactggtgtt tggaagtcta cacaattgaa acatcttcgt
1921 tatggaggtt ttaatcaagc atctaacagt tgcttttcta taagcccatt tttcccaaac
1981 ttgtactcat tgcctcataa taatgtacaa acttgatgt ggctggatga taaattttt
2041 gaggcgggat tgttgcaccg attgatcaat ttaagaaaac tgggtatagc aggagtatct
2101 gattctacag ttaagatatt atcagcattg agcctgtgc caacggcgtt ggaggttctg
2161 aagctcaaaa ttacaggga catgagtgag caaataaact tgtcgtccta tccaaatatt
2221 gttaagttgc gttgaatgt tgcggaaga atgcgcttga actgtgaagc atttcctcca
2281 aatcttgtca agcttactct tgtcgggat gaggtagacg gtcatgtagt ggcacagctt
2341 aagaaattgc ccaaattaag gatacttaaa atgtttgggt gcagtcataa tgaagaaaag
2401 atggatctct ctggtgatgg tgatagcttt ccgcaacttg aagttctgca tattgatgaa
2461 ccagtgggt tgtctgaagt aacgtgtagg gatgatgtca gtatgcctaa attgaaaaag
2521 ttgttacttg tacaacgcg cccttctcca attagtctct cagaacgtct tgcaaagctc
2581 agaatatga
```

SEQ. ID. 9 = NUCLEIC ACID SEQUENCE OF *Rpi-mcq1.2*

```
   1 atggctgaaa ttcttcttac aacagtcatc aataaatctg taggaatagc tgcaaatgta
  61 ctcttcaag aaggaacgcg tttatattgg ttgaaagagg acatagattg gctccaacga
 121 gaaatgagac acattcgatc atatgtagac gatgcaaaga ccaaggaagt tggaggcgat
 181 tcaagggtca gaaacttatt aaagatatt caaaacttat caggtgatgt ggaggatcta
 241 ttagatgagt ttcttccaaa aattcaacaa tccaataagt tcatttgttg ccttaagaca
 301 gtttcttttg ccgatgagtt tgccatggag attgagaaga taaaagaag agttgctgat
 361 attacccgtg taaggacaac ttacaacatc acagatacaa gtaacaataa tgatgattgc
 421 attccattgg accggagaag attgttcctt catgctgatg aaacagaggt catgggtctg
 481 gaagatgact tcaatacact aaaagccaas ttacttgatc aagatttgcc ttatggagtt
 541 gtttcaatag ttggcatgcc cggtctagga aaacaactc ttgccaagaa acttatagg
 601 catgtccgtg atcaatttga gagctcggga ctggtctacg tgtcccaaca gccaagagcg
 661 ggagaaatct tacgtgacat agccaaacaa gttggactgc caaagagga aagaaagaa
 721 aacttggagg gcaacctacg atcactcttg aaaacaaaaa ggtatgttat cctcctagat
 781 gacatttggg atgttgaaat ttgggatgat ctaaaactcg tccttcctga atgtgattca
 841 gaaattggca gtaggtaat tataacctct cgaaatagta atgtaggcag atacataga
 901 ggggatttct caattcacat gttgcaacct ctagattcgg agaacagttt tgaactcttt
 961 accaagaaaa tctttacttt tgataacaat aataattggg ccaatgcttc accagacttg
1021 gtagatattg gtagaagtat agttggtaga tgcggaggta tacctctagc cattgtggtc
1081 actgcaggca tgttaaggcg aagagaaaga acagaacatg catggaacag agtacttgag
1141 agtatgggcc ataaagttca agatggatgt gctaaggtat tggctttgag ttacaatgat
1201 ttgcccattg cattaaggcc atgtttcttg taccttggcc ttttccccga ggaccatgaa
1261 attgtgcct ttgatttgac aaatatgtgt attgctgaga agctgatagt tgtaaatagt
1321 ggcaatgggc gagaggctga aagtttggcg gaggagtgtc taaatgattt tgtttctaga
1381 aacttgattc aagtttccaa aagaaaatgt aatggaagaa tttcaagtta tcgcatacat
1441 gacttgttac atagtttgtg cgtcgaattg ggcaaggaas gtaacttttt tcactctgaa
1501 cacaatgcat tggtgatcc agacaatgtt gctagggtgc gaaggattac attctactct
1561 gataataatg ccatgagtaa gtcttctcgt tcaaatccta agcctaagaa acttcgtgca
1621 cttttctgtt tcacaaattt agactcttgc atatttctc atttggctca tcatgacttc
1681 aaattattac aagtgttggt tgtagttatc tcttataatt ggttgagtgt cagtatctca
1741 aacaaatttg ggaagatgag ttgcttgcgc tattttgagat tggagggggcc aattgtggga
1801 gaactgtcaa atagtattgt gaagctcaaa cgtgtagaga ccatagatat tgcagcggat
1861 aacattaaaa ttccttgtgg tgttgggagg tctaaacaat tgagacatct ccgtaataga
1921 gaagaacgtc gctatattctt ttctgtaagc ccattttgcc taaacatgta cccattgcct
1981 cctaataato tacaaacttt ggtgtggatg gatgataaat tttttgaacc gagattgttg
2041 cacccgattga tcaattcaag aaaattgggt atatggggca catctgattc tacaattaag
2101 atatttatcag cattgagcc tgtgccaaca gcgttgaagg ttctgaagct ctacttttttg
2161 agggacctga gtgagcaaat aaacttgtca acctatccaa atattgttaa gttgaatttg
2221 caaggattcg taagatgcg cttgaactct gaacaattcc ctcaaaatct tgtcaagctt
2281 attcttgaca aaattgaggt agagggtcat gtagtgcag ttcttaagaa attgccaaaa
2341 ttaaggatac ttaaaatgta tgggtgcaaa cataatgaag aaaagatgga tctctctggt
2401 gatggtgatg gtgatagctt tccgcaactt gaagtttgc atattgagag accattcttc
2461 ttgtttgaaa taacgtgcac agatgatgac agtatgccta attgaaaaa gctattactt
2521 acaacttcga acgttaggct ctcggaaaga cttgcaaaac tgagagtatg a
```

SEQ. ID. 10 = NUCLEIC ACID SEQUENCE OF A PORTION OF *Rpi-mcq1.1*

TRANSGENE FROM PSLJ21153 (INCLUDES OWN PROMOTER AND TERMINATOR)

```
   1 ggatctgggt tttaccggt cttttattaa atgggtggta gaaaataaat
  51 tatatatata tatttttgg agtgaacaca cgcgcaggtg ctgagattac
 101 cattgttgtc caaatggtgt atttataatg gttgaaaatt gtttcgtggt
```

Figure 12 (continued)

```
 151  gtaataggac tcccacaaac tttaagtgtc tgcttcaaaa aatggtttaa
 201  gtttaatggg gtaactatgt atttcctcta actaaaaatc aaaaaccata
 251  gcaaaaaat aaggtaaaga accataatat aatcaaataa gcataaaccc
 301  atctcaaaaa actcattttt tttaacaata aaccaaacat aaaaccaata
 351  taccccaaag acttaacaaa gtttcatatt aactaaaaat caaaaaccat
 401  agtaaagcaa taacgtaaag aaccataata taatcaaaata agcataaacc
 451  catctcaaaa actcattttt ttcatcaaac atcaaaaaac aatgagtaaa
 501  agttctacaa caagaaccaa acataaaacc aagagaccc aaagacttaa
 551  caaagttcca tattaacaaa aaatcaacaa ccataacaaa acaataaggc
 601  aaagaacaat agcataacca aataagcata aacccatctt aaaaaactca
 651  tttttatcac caaacattaa aaaactcatt tttttcacca aacatcaaaa
 701  aacaatgagt aaaagttcta caacatgaac caaacataaa accaacatac
 751  cccaaacact taacaaagct ccatataaac aacaaaacaa caaggcaaag
 801  aagcataata tagcaaaata agcataaatc catctcaaac aaattataaa
 851  aaaactaacc taatgaagac aagttttcag ggtttaagag gcaagaaaat
 901  gagagcggc taggtcttac tgtgaactgt ggggtttaag aaagggtata
 951  tataagtaca ctgcctttcg acttttcag agtgaaaaaa atactcatat
1001  atctgcggcg ttttaaaagg agctcgaggg taatttact gcttagaggt
1051  gttgtacctt gattttaaa gagagtattt ttggaattaa tgtacaacat
1101  gcattatgcg aactcataat agtttgtaaa tgagcaattg tcgagattat
1151  gaaagctatt ttaggatgtt atgtgaatta tttgtattta tttcgaaata
1201  gttttcact ttatttcaaa agcagtttga ttgtaaaaat cgtcaatttt
1251  tagttgtttt attctttcat ttgcaagaaa aaaaaattaa gcataaatct
1301  atttttcaatt tcaattctat aaatattacg aaaaatattt gaatttcaca
1351  atcaaatgcc catttagttt tttttttttt aaactttaat acgagacttt
1401  tttcatattt tatattttcc tcaaattaga tcctttttt tcctttcctt
1451  gttgtaagtc cttgtgaaaa aacctccaaa tcctaacttg tgttgtgata
1501  ccacaaggat ttaaagatta cacataatga aacaaaaaaa aaaaaaaatc
1551  aattcgagct tgaaaatga aaaaaattga taaattttt ttttctttaa
1601  tcactattac gtgatacaaa tttgaattag tcgaattaat atatttaaaa
1651  caaaacactc cttatcagaa aagtgaagaa attctgacca ttccactaga
1701  gtcattatgg tgatggaagt ttaataaaat agaaccgaag aatcgaatgc
1751  ccactcaaat tttttttgaga gcccaaactc acagccatga acccaaattg
1801  ggtaaagttt tgcaagacgt tcatctaaca gttaggaaac ttaaaatgcc
1851  gtctagatat ataatttatt tttttaacat atcgtgtgat tgatatatac
1901  taaagatgtt tgcttagtta cgtgattttt ttaaaaaaaa agagagtaca
1951  ttatcaatca tcagccacaa aatattaaaa gtcacagttt gtttcttaaa
2001  ttccatatcg aattaaattg aatgacagtt aaattggaat gaatggtgta
2051  atttcctttg actattgtac tagtatctta tccacagcat gtgttgttcc
2101  ttccttcttt cgttttcat ttacttgaca ttagtaggag acttggcagt
2151  ggactccaac tattctaagc tgaccttct tttcctttac caattatctt
2201  ctcttttcta atttctcatt ctgatcggtt tttgtagcta ctgaaaaaga
2251  aagagtgaag aaatggctga aattcttctt acagcagtca tcaataaatc
2301  tgtagaaata gctggaaatg tactctttca agaaggtacg cgtttatatt
2351  cgttgaagga ggatatagat tggctccaaa gagaaatgag acacattcga
2401  tcatatgtag acaatgcaaa ggccaaggaa gttggaggtg atcaagggt
2451  gaaaaactta ttaaaagata ttcaacaact cgcaggtgat gtggaggatc
2501  tcctagatga gttttcttcca aaaattcaac aatccagtaa gttcaaaggc
2551  gcaatttgtt gccttaagac cgtttcttt gcggatgagt ttgctatgga
2601  gattcagaag ataaaaagaa gggttgtgga cattgatcgt gtaaggacaa
2651  cttacaacat catggataca aataacaaca atgattcat tccattggac
2701  cagacaagat tgttccttca tgttgatgaa acagaggtca tcggtttgga
2751  tgatgacttc aatacactac aagccaaatt acttgaccaa gatttgcctt
2801  atggagtgt ttcaatagtt ggcatgcccg gtctaggaaa aacaactctt
2851  gccagaaac tttataggca tgtccgtcat aaatttgagt gttcgggact
2901  ggtctatgtt tcacaacagc caagggcggg agaaatctta atcgacatag
2951  ccaaacaagt tggactgacg gaagacgaaa ggasagaaaa cttggagaac
3001  aacctacggt cactcttgaa aagaaaaagg tatgttattc tcttagatga
3051  catttgggat gttgaaattt gggatgatct aaaacttgtc cttcctgaat
3101  gtgattcaaa aattggcagt aggataatta taacctctcg aaatagtaat
```

Figure 12 (continued)

```
3151 gtaggcagat acataggagg ggatttctca attcacgtgt tgcaacctct
3201 aaattcggag aacagttttg aactctttac caagaaaatc tttattttttg
3251 ataacaataa taattggacc aatgcttcac caaacttggt agatattggt
3301 agaagtatag ttggtagatg tggtggtata ccactagcca ttgtggtgac
3351 tgcaggcatg ttaagggcaa gagaaagaac agaacgtgca tggaacaggt
3401 tacttgagag tatgagccat aaagttcaag atggatgtgc taaggtattg
3451 gctctgagtt acaatgattt gccaattgca ttaaggccat gtttcttgta
3501 ttttggcctt taccccgagg atcatgaaat tcgtgcttttt gatttgacaa
3551 atatgtggat tgctgagaag ttgatagttg taaatagtgg caatgggcga
3601 gaggctgaaa gtttggcgga tgatgtccta aatgatttgg tttcaagaaa
3651 catgattcaa gttgccaaaa ggacatatga tggaagaatt tcaagttgtc
3701 gcatacatga cttgttacat agtttgtgtg ttgacttggc taaggaaagc
3751 aacttctttc acaccgagca caatgcattg ggtgatccg gaaatgttgc
3801 taggctgcga aggattacat tctactctga taataatgcc atgaatgagt
3851 tcttccgttc aaatcctaag cttgagaagc ttcgtgcact tttctgtttt
3901 acagaagacc cttgcatatt ttctcaactg gctcatcttg atttcaaatt
3951 attgcaagtg ttggttgtag tcatctttgt tgatgatatt tgtggtgtca
4001 gtatcccaaa cacatttggg aacatgaggt gcttacgtta tctgcgattc
4051 cagggcatt tttatgggaa actgccaaat tgtatggtga agctcaaacg
4101 tctagagacc ctcgatattg gttatagctt aattaaattt cctactggtg
4151 ttggaagtc tacacaattg aaacatcttc gttatggagg ttttaatcaa
4201 gcatctaaca gttgctttc tataagccca ttttttcccaa acttgtactc
4251 attgcctcat aataatgtac aaactttgat gtggctggat gataaatttt
4301 ttgaggcggg attgttgcac cgattgatca atttaagaaa actgggtata
4351 gcaggagtat ctgattctac agttaagata ttatcagcat tgagccctgt
4401 gccaacggcg ctggaggttc tgaagctcaa aatttacagg gacatgagtg
4451 agcaaataaa cttgtcgtcc tatccaaata ttgttaagtt gcgtttgaat
4501 gtttgcggaa gaatgcgctt gaactgtgaa gcatttcctc caaatcttgt
4551 caagcttact cttgtcggcg atgaggtaga cggtcatgta gtggcagagc
4601 ttaagaaatt gcccaaatta aggatactta aaatgtttgg gtgcagtcat
4651 aatgaagaaa agatggatct ctctggtgat ggtgatagct ttccgcaact
4701 tgaagttctg catattgatg aaccagatgg gttgtctgaa gtaacgtgta
4751 gggatgatgt cagtatgcct aaattgaaaa agttgttact tgtacaacgc
4801 cgcccttctc caattagtct ctcagaacgt cttgcaagc tcagaatatg
4851 aaattcacaa tgtgtcaata tataggttag tttgctacgt taatctccca
4901 ttatgtctaa tgaattgcgc gcagatgcat ttgagaatga ttgattgtaa
4951 attgtaattg taataaataa ataatgttt gattgctttc tgaagttgat
5001 gtatttgtgg cttgtgtattt gtaaaacata ttttatttatt gtcttatcac
5051 ttatgtttat ttaccttttgg aattagcagt agctttcgtt tcttctcttc
5101 ttcaataatc aatgctcgca aatataaatt aggggcgtat tttattggtt
5151 tggtttatcg gtttataaat tcgtttaatt aataaccaat tcaattaaat
5201 attttttat cggtttgggg tccttagcgg ttcgatattt gatttaacca
5251 ataagaaaat acttataaaa caaatatatg acttctcaaa caatttagcg
5301 tggcaagata atacgtaac tttacaaata ctcatataat agaaacaaca
5351 ataactaaca tgaaagaat tatacaagtg taacacaaag aaaaactaag
5401 aggaatatgc ttcttacttt acatttgac gttttgtata atgtgaattt
5451 ttgaacttaa agtcactgtg aagtgtgatg tgaaggtgaa aggacaaatg
5501 cactaactag taagtattg cgattaatat ttaatgttta tgtatgagta
5551 aaatagtaaa ttattatagt tttattgggt tatcagtata cccaataact
5601 caatattaaa aatcaaaatc gaaccggtaa cccaatattt ttttcttttct
5651 ataaaaccat taaaacctca ttgacccaat aacccaataa caataaatca
5701 atagcacttt ttccattttta atttatcgat cgattagatt tttgcaaccc
5751 actaatataa attactacct gttatagcaa gtgcaagtag agaattgata
5801 tatagctcac attttacaaa ttctttctag tgttaatcgt caaaaacatt
5851 agcttctcaa taatatatgg c
```

SEQ. ID. 11 = NUCLEIC ACID SEQUENCE OF A PORTION OF *Rpi-mcq1.2* TRANSGENE FROM PSLJ21148 (INCLUDES OWN PROMOTER AND TERMINATOR)

Figure 12 (continued)

```
   1  aatagggtta aaatggtaaa ctcactacac caatcattgt tttgcatatt
  51  gaggaaccgg acatgttgcc tgaagttatt gtattttcta tatcatttac
 101  atatcataca attaggtcca atcgcgtttc ctttcttttt tggctagaat
 151  ccagcaatat gaacaagaaa aataatacaa acagtaaatg aaaataaaat
 201  tatctgataa tatatttagc ttcagaacca aagattgctt gttacaggtg
 251  aaaaaaatac tactccaatg caacgcttaa aactcttcga taatcatata
 301  aaaaggctag tctagattgt actcgaatgt tatcacgtac atggccacat
 351  atctgactcc aaagagagag atatctgccc tcaacacctt cctagctgca
 401  atcatcagca gaaatttact tgttcaaaca ggctcgcgct tatatatatt
 451  ggttgaaaga ggacaatgac tggagaagtg aggcacattc gatattatct
 501  agctaggaag gacaactttt ggtatcactc atacaagtaa caacaatgac
 551  caatatgact acgttccact agacgtgga agattattcc ttcatgttga
 601  tgaaacagag gtcattggtt tgggaaaat actatcaaat attcaagttt
 651  actggtaatt aaaactactg atagtttagt ggatttgaat aaaatgtgtt
 701  atgtttataa tggtctttag atattctacc tatattgaaa gtttcaaact
 751  attggaagca atcatttctg catatataaa aacttatttg cacggaatat
 801  ttgtcgcttt acgagttctt tctttcttct ttcgtatact tgacaatagg
 851  agacttgttt gtggactaaa agcgaatagt ggaatatcat tatttcctta
 901  ataactttca gattagaagg aagtccgtag ctcttccaa tatgtatggt
 951  ctctatatgt ttgagcttga caatatcatt ttacagttct ccaggaatat
1001  cccctccaat ctcaaatagt caatagtgat atcttcataa taatcttgag
1051  gcatgactac caccaacatt tgcaataatt tgaagtcaaa atgagtcatt
1101  tgataaaata tgcaaggctc ttttgtgaaa caaaaagcct tttaggttta
1151  ggattcaaag aattgaactc attcataaca tcatcagagt agaatgtaat
1201  ccttcgcagc gtagcaacgt tgtcaggatc accaaatgca tagtgatcag
1251  tgtgaaataa gttactacta tcaacttctc agcaatccac atatttgtcc
1301  aatcaaaacc atgaatttca aggtccttgg gggaaaaggc caaagtacaa
1351  atttctacta aatcgtccca aaattgagtt ccacattcct ttagatttac
1401  taaatctatt ccgacaattc ccactcgaaa gaaatttcaa tttcggaacc
1451  aaaaagggtt gtgatggagt ggtaaatatt cctcatcct taaccaaatc
1501  cggatttaat cgggcttcaa attgagtggt ggaaaaactt tcaatgacct
1551  tattaatatt tacttttttt aaaactagaa agcaaattat gagtgatttg
1601  ttaactattc tagctactga tgctacatac taatacaatc aaatctctac
1651  aactaaagtt gtttgtcctg tttacgtttt agttgttata gcataatgtt
1701  gatataaaaa acatttgata taatataatg taacataaat attgtttttt
1751  attttccaaa aaataacatg ttaattaatg tattactcct ttttcattag
1801  tgtgtagctg cccccacgtt gtctctccct ttcttctgtc ttttgtttaa
1851  tttacttgac attattagga gacttgattg tggactccag cactaaaaag
1901  aaaaagcaaa tagcagatgg aatgagttta agctgatctt tcttttcctaa
1951  ttactcgttc tgatctattt tttctagcta ctgaaaaga gagaaaaaaa
2001  tggctgaaat tcttcttaca acagtcatca ataaatctgt aggaatagct
2051  gcaaatgtac tctttcaaga aggaacgcgt ttatattggt tgaaagagga
2101  catagattgg ctccacagag aaatgagaca cattcgatca tatgtagacg
2151  atgcaaaggc caaggaagtt ggaggcgatt caagggtcag aaacttatta
2201  aaagatattc aacaactggc aggtgatgtg gaggatctat tagatgagtt
2251  tcttccaaaa attcaacaat ccaataagtt catttgttgc cttaagacag
2301  tttcttttgc ccatgagttt gccatggaga ttgaagagat aaaaagaaga
2351  gttgctgata ttacccgtgt aaggacaact tacaacatca cagatacaag
2401  taacaataat gatgattgca ttccattgga ccggagaaga ttgttcctttc
2451  atgctgatga aacagaggtc atcggtctgg aagatgactt caatacacta
2501  aaagccaaat tacttgatca agatttgcct tatggagttg tttcaatagt
2551  tggcatgccc ggtctaggaa aaacaactct tgccaagaaa ctttataggc
2601  atgtccgtga tcaatttgag agctcgggac tggtctacgt gtcccaacag
2651  ccaagagcgg gagaaatctt acgtgacata gccaaacaag ttggactgcc
2701  aaaagaggaa aggaaagaaa acttggaggg caacctacga tcactcttga
2751  aaacaaaaag gtatgttatc ctcctagatg acatttggga tgttgaaatt
2801  tgggatgatc taaaactcgt ccttcctgaa tgtgattcag aaattggcag
2851  taggataatt ataacctctc gaaatagtaa tgtaggcaga tacataggag
2901  gggatttctc aattcacatg ttgcaacctc tagattcgga gaacagtttt
```

Figure 12 (continued)

```
2951 gaactctttta ccaagaaaat ctttactttt gataacaata ataattgggc
3001 caatgcttca ccagacttgg tagatattgg tagaagtata gttggtagat
3051 ggggagtat acctctagcc attgtggtca ctgcaggcat gttaagggca
3101 agagaaagaa cagaacatgc atggaacaga gtacttgaga gtatgggcca
3151 taaagttcaa gatggatgtg ctaaggtatt ggctttgagt tacaatgatt
3201 tgcccattgc attaaggcca tgtttcttgt acctggcct tttccccgag
3251 gaccatgaaa ttcgtgcctt tgatttgaca aatatgtgga ttgctgagaa
3301 gctgatagtt gtaaatagtg gcaatgggcg agaggctgaa agtttggcgg
3351 aggatgttct aaatgatttt gtttctagaa acttgattca agtttcccaa
3401 agaaaatgta atggaagaat ttcaagttat cgcatacatg acttgttaca
3451 tagtttgtgc gtcgaattgg gcaaggaaag taacttttt cacactgaac
3501 acaatgcatt tggtgatcca gacaatgttg ctagggtgcg aaggattaca
3551 ttctactctg ataataatgc catgagtaag ttcttccgtt caaatcctaa
3601 gcctaagaaa cttcgtgcac ttttctgttt cacaaattta gactcttgca
3651 tattttctca tttggctcat catgacttca aattattaca agtgttggtt
3701 gtagttatct cttataattg gttgagtgtc agtatctcaa acaaatttgg
3751 gaagatgagt tgcttgcgct atttgagatt ggaggggcca attgtgggag
3801 aactgtcaaa tagtattgtg aagctcaaac gtgtagagac catagatatt
3851 gcagggata acattaaaat tccttgtggt gtttgggagt ctaaacaatt
3901 gagcatctc cgtaatagag aagaacgtcg ctatttcttt tctgtaagcc
3951 cattttgcct aaacatgtac ccattgcctc ctaataatct acaaactttg
4001 gtgtggatgg atgataaatt ttttgaaccg agattgttgc accgattgat
4051 caatttaaga aaattgggta tatggggcac atctgattct acaattaaga
4101 tattatcagc attgagccct gtgccaacag cgttggaggt tctgaagctc
4151 tactttttga gggacctgag tgagcaaata aacttgtcaa cctatccaaa
4201 tattgttaag ttgaatttgc aaggattcgt aagagtgcgc ttaactctg
4251 aagcattccc tccaaatctt gtcaagctta ttcttgacaa aattgaggta
4301 gagggtcatg tagtggcagt tcttaagaaa ttgcccacat taaggatact
4351 taaaatgtat gggtgcaaac ataatgaaga aaagatggat ctctctggtg
4401 atggtgatgg tgatagcttt ccgcaacttg aagttttgca tattgagaga
4451 ccattcttct tgtttgaaat aacgtgcaca gatgatgaca gtatgcctaa
4501 attgaaaaag ctattactta ccacttcgaa cgttaggctc tcggaaagac
4551 ttgcaaaact gagagtatga aaatcccaat gtgtcaacag gttagttatt
4601 tacttctaat atctcggaat aagctaattc atatttaatt gatgaactaa
4651 atattttatg tctaataaat tgcagatgca tttcagaatg atttaagtct
4701 ttgctggaga gcatcttcta tgcctgtttg tatttgaaat aaataaataa
4751 aatgtttgat tgcttctga agttgatgta tttgtggctt gtgatttgta
4801 aaacatattt atttattgtc ttatgtatat ttacctttgg atttagcagt
4851 agctttagtt tattttcttc ttcaagaatc aaagttcaca atataagtta
4901 tgacttgcat cgatcggttc gggttgattt tatgtattgt catttcagtt
4951 tattggtttt tggttatggt ttatctatca attggtttaa ccaataagaa
5001 aatgcttata aaataaatat ataatttctc taacaattta acatgacaag
5051 ataataacaa aactttacaa atgttcataa aatagaaatt ataataacta
5101 acattgaaag aactatacaa gtgtagcaca aagagaaact aataggaata
5151 gtgttcttac tttatgtttt gacgttttgt ataatgtgaa gttttgaatt
5201 taaagtcatt atgaagtttt gaagttaagg ctaaaggaca gatgcactaa
5251 ctagtaaggt attgagatta atatttaata tttatgtaca tgaaaagtac
5301 tatattacta taatcttatt ggttatcgg tatacccaat aacccaatat
5351 aaaaagcgaa aaccaagcca ataatccttt ttttttata aaatcattaa
5401 aaactattaa cccaataacc caatagaaat aaactaatcc cgggataatt
5451 tttgagtggc ctttaattca ttgtttggtt gcaaaggtag ggataactta
5501 tcccaggatt aacaattagt cctgggataa tttatccctc actagggatc
5551 atatagtaat cccatga
```

SEQ. ID. 3 = NUCLEIC ACID SEQUENCE OF *Rpi-nrs1*

```
  1 atgaattatt gtgtttacaa gacttgggcc gttgactcta acactaaagc aaatagtaca
 61 tcttttctta tccttttctc ttactttccc ttcctcatcc tcacatttag aaaaaagaaa
```

Figure 12 (continued)

```
 121 tttaacgaaa aattaaagga gatggctgaa attcttctca cagcagtcat caataaatca
 181 atagaaatag ctggaaatgt actctttcaa gaaggtagc gttttatattg gttgaaagag
 241 gacatcgatt ggctccagag agaaatgaga cacattcgat catatgtaga caatgcaaag
 301 gcaaaggaag ttggaggcga ttcaaggctg aaaacttat taaaagatat tcaacaactg
 361 gcaggtgatg tggaggatct attagatgag ttcttccaa aaattcaaca atccaataag
 421 ttcattcgtt gccttaagac ggttttcttttt gccgatgagt ttgctatgga gattgagaag
 481 ataaaaagaa gagttgctga tattgaccgt gtaaggaca cttacagcat cacagataca
 541 agtaacaata atgatgattg cattccattg gacggagaa gattgttcct tcatgctgat
 601 gaaacagagg tcatcggtct ggaagatgac ttcaatacac tacaagccaa attacttgat
 661 catgatttgc cttatggagt tgtttcaata gttggcatgc ccggtttggg aaaaacaact
 721 cttgccaaga aacttatag gcatgtctgt catcaatttg agtgttgggg actgctctat
 781 gttcacaaac agccagggc gggagaaatc ttacatgaca tagccaaaca agttggactg
 841 acggaagagg aaaggaaaga aaactggag aacaactac gatcactctt gaaaataaaa
 901 aggtatgtta ttctcttaga tgacatttgg gatgttgaaa tttgggatga tctaaaactt
 961 gtccttcctg aattgtgattc aaaaattggc agtaggataa ttataacctc tcgaaatagt
1021 aatgtaggca gatacatagg aggggattc tcaatccacg tgttgcaacc cctagattca
1081 gagaaagct ttgaactctt taccaagaaa atctttaatt ttgttaatga taattgggcc
1141 aatgttcac cagacttggt aaatattggt agatgtatag ttgaagatg tggaggtata
1201 ccgctagcaa ttgtcgtgac tgcaggcatg ttaaggcaa gaggaagac agaacatgca
1261 tggaacagag tactgagag tatggctcat aaaattcaag atggatgtgg taagtattg
1321 gctctgagtt acaatgattt gcccattgca ttaaggccat gttcttgta ctttggtctt
1381 tacccgagg accatgaat tcgtgctttt gatttgacaa atatgtggat tgctgagaag
1441 ctgatagttg taaatactgg caatgagcga gaggctgaaa gtttggcga tgatgtccta
1501 aatgatttgg tttcaagaaa cttgattcaa gttgccaaaa ggacatatga tggaagaatt
1561 tcaagttgtc gcatacatga cttgttacat agttgtgtg tggacttgc taaggaaagt
1621 aacttctttc acaggagca ctatgcattt ggtgatccta gcaatgttgc tagggtgcga
1681 aggattacat tctactctga tgataatgcc atgaatgagt tcttccattc aaatcctaag
1741 cctatgaagc ttcgttcact tttctgtttc acaaaagacc gttgcatatt ttctcasatg
1801 gctcatctta acttcaaatt attgcaagtg ttggttgtag tcatgtctca aaagggttat
1861 cagcatgtta ctttccccaa aaaaattggg aacatgagtt gcctacgcta tgtgcgattg
1921 gaggggcaa ttgagtaaa attgccaaat agtattgtca agctcaaatg tctagagacc
1981 ctggatatat ttcatagcto tagtaaactt cctttggtg tttgggagtc taaaatattg
2041 agacatcttt gttacacaga agaatgttac tgtgtctctt ttgcaactc atttgcga
2101 atcatgcctc ctaataatct acaactttg atgtgggtgg atgataaatt ttgtgaacca
2161 agattgttgc accgattgat aaattttaaga acattgtgta taaggatgt atccggttct
2221 accattaaga tattatcagc attgagccct gtgcctaaag cgttggaggt tctgaagctc
2281 agattttca agaacacgag tgagcaaata aacttgtcgt cccatccaa tattgtcgag
2341 ttgggttttg ttggtttctc agcaatgctc ttgaacattg aagcattcc tccaaatctt
2401 gtcaagctta atcttgtcgg cttgatgta gacggtgatc tattggcagt gcttaagaaa
2461 ttgcccaaat taaggatact tatattgctt tggtgcagac atgatgcaga aaaaatggat
2521 ctctctggtg atagctttcc gcaacttgaa gttttgtata ttgaggatgc acaggggttg
2581 tctgaagtaa cgtgcatgga tgatatgagt atgcctaaat tgaaaaagct tttctgta
2641 caaggcccaa acattcccc aattagtctc agggtctcgg aacggcttgc aaagttgaga
2701 atatcacagg tactataa
```

SEQ. ID. 4 = AMINO ACID SEQUENCE OF Rpi-oka1

```
   1 MNYCVYKTWA VDSYFPPLIL TFRKKKFNEK LKEMAEILLT AVINKSIEIA GNVLFQEGTR
  61 LYWLKEDIDW LQREMRHIRS YVDNAKAKEV GGDSRVKNLL KDIQQLAGDV EDLLDEFLPK
 121 IQQSNKFICC LKTVSFADEF AMEIEKIKRP VADIDRVRTT YSITDTSNDN DDCIPLDRRR
 181 LFLHADETRV IGLEDDFNTL QAKLLDHDLP YGVSIVGMP GLGKTTLAKK LYRHVCRQFE
 241 CCGLVYVSQQ PRAGEILHDI AKQVGLTEEE RKENLENNLR SLLKIKRYVI LLDDINDVEI
 301 NDDLKLVLPE CDSKIGSRII ITSRNSNVGR YIGGDFSIHV LQPLDSEKSF ELFTEKIFNF
 361 VNDNWANASP DLVNIGRCIV ERCGGIPLAI VVTAGMLRAR GRTEHAWNRV LESMARKIQD
 421 GCGKVLALSY NDLFIALEEC FLYFGLYPED BEIPAFDLTN MWIAEKLIVV NTGNGREAES
 481 LADDVLNDLV SRNLIQVAKR TYDGRISSCR IRDLLHSLCV DLAKESNFFH TEHNAPGDPS
 541 NVARVRRITF YSDDNAHNEF FHLNFKRKL RSLECFTKDR CIFSQAAHLH FRLLQVLFYV
 601 MSQKGYQHVT FPNKIGNMSC LRYVRLEGAI RVKLPNSIVK LKCLETLGIF BSSSKLEFGV
 661 NESKILRHLC YTEECYCVSF ASPFCRIMPP NNLQTLMWVD DKFCEPRLLH RLINLRTLCI
 721 RDVSGSTIKI LSALSPVPPA LEVLKLRFFK NTSEQINLSS HPNIVELGLV GFSAGLLNIE
 781 AFFPNLVELR LVGIMVDGHL LAVLRKLPKL RILILLWCRH DAERMDLSGD SFPQLEVLYI
 841 EDAQGLSEVT CMDDMSMPKL RKLFLVQGPN ISPISLRVSE RLAKLRISQV L*
```

SEQ. ID. 12 = AMINO ACID SEQUENCE OF Rpi-oka2

```
   1 MNYCVYKTWA VDSNTKANST SFLSFTSYFP FLILTFRKKK FNEKLKEMAE ILLTAVINKS
  61 IEIAGNVLFQ EGTRLYWLKE DIDWLQREMR HIRSYVDNAK AKEVSGDSRV KNLLKDIQQL
 121 AGDVEDLLDE FLPKIQQSNK FICCLKTVSF ADEFAMEIEK IKRVADIDRA VRTTYSITDT
 181 SNNNDDCIPL DRRRLFLHAD ETEVIGLEDD FNTLQAKLLD HDLPYGVVSI VGMPSLGKTT
 241 LAKKLYRHVC HQFECSGLVY VSQQPRAGEI LHDIAKQVGL TEEERKENLE NNLRSLLKIK
 301 RYVILLDDIW DVEINDDLKL VLPECDSKIG SRIITSRNS NVGRYIGGDF SIHVLQPLDS
```

Figure 12 (continued)

```
361 EKSPELFTKK IFNFVNDNWA NASPDLVNIG RCIVERCGGI PLAIVVTAGM LRARGRTEHA
423 WNRVLESMAH KIQDGCGKVL ALSYNDLPIA LRPCFLYFGL YPEDHEIRAF DLTNMWIAEK
481 LIVVNTGNGR EAESLADDVL NDLVSRNLIQ VAKRTYDGRI SSCRIHDLLH SLCVDLAKES
541 NFFHTEHYAF GDPSNVARVR RITFYSDDNA MNEFFHLNPK PRKLRSLFCF TKDRCIFSQM
601 AHLNFKLLQV LVVVMSQKGY CHVTFPKKIG NMSCLRYVRL EGAIRFKLPN SIVKLKCLET
661 LDIFHSSSKL PFGVWESKIL RHLCYTEECY CVSFASPFCR IMEPPNNLQTL MNVDDKPCEP
721 RLLHRLINLR TLCIMDVSGS TIKILSALSP VPKALEVLKL RFFKNTSEQI NLSSHPNIVE
781 LGLVGFSAML LNIEAFFPNL VKLNLVGLMV DGHLLAVLKK LPKLRILILL WCRHDAEKMD
841 LSGDSFPQLE VLYIEDAQGL SEVTCMDDWS MPKLKKLFLV QGPNISPISL RVSERLAKLR
901 ISQVL*
```

SEQ. ID. 5 = AMINO ACID SEQUENCE OF *Rpi-mcq1.1*

```
  1 MAEILLTAVI NKSVEIAGNV LFQEGTRLYW LKEDIDWLQR EMRHIRSYVD HAKAKEVGGD
 61 SRVKNLLKDI QQLAGDVEDL LDEFLPKIQQ SSKFKGAICC LKTVSKADEF AMEIEKIKKR
121 VVOIDRVRTT YNIMDTNNNN DCIPLDQRRL FLBVDETEVI GLDDDFNTLQ AKLLDQDLPY
181 GVVSIVGMPG LGKTTLAKKL YRHVREKFEC SGLVYVSQQP RAGEILIDIA KQVGLTEDER
241 RENLENNLRS LLKRKRYVIL LDDIWDVEIW DDLKLVLPEC DSKIGSRIII TSRMSHVGRY
301 IGGDFSIHVL QFLNSENSFE LFTKKIFIFD NNNNWTMASP NLVDIGRSIV GRCGGIPLAI
361 VVTAGMLRAR ERTERAWNRL LRSMSHKVQD QCAKVLALSY NDLPIALRPC FLYFGLYPED
421 HEIRAFDLTN MWIAEKLIVV NSGNGREAES LADDVLNDLV SRNMIQVAKR TYDGRISSCR
481 IHDLLHSLCV DLAKESNFFH TEHHALGDPG NVARLRRITF YSDNNAMNEF FRSNPKLEKL
541 RALFCFTEDP CIFSQLAHLD FKLLQVLVVV IFVDDICGVS IPNTFGNMRC LRYLAFQGHF
601 YGKLPNCMVK LKRLETLDIG YSLIKFPTGV WKSTQLKHLR YGGFNQASNS CFSISPFFPN
661 LYSLPHNNVQ TLMWLDDKFP EAGLLHRLIN LRKLGIAGVS DSTVKILSAL SPVPTALEVL
721 KLKIYRDMSE QINLSSYPNI VKLRLRVCGR GRLNCEAFFP NLVKLTLVGD EVDGHVVAEL
781 KKLPKLRILK MPGCSHNEEK MDLSGDGDSF PQLEVLRIDE PDGLSEVTCR DDVSMPELKK
841 LLLVQSRPSP ISLSERLAKI RI*
```

SEQ. ID. 13 = AMINO ACID SEQUENCE OF *Rpi-mcq1.2*

```
  1 MAEILLTTVI NKSVGIAANV LFQEGTRLYW LKEDIDWLHR EMRHIRSYVD DAKAKEVGGD
 61 SRVRNLLKDI QQLAGDVEDL LDEFLPKIQQ SNKPICCLKT VSPADEFAME IEKIKPRVAD
121 ICPVRTTYNI TDTSNNNDDC IPLDRRRLFL HADETEVIGL EDDFNTLKAR LLDQDLPGV
181 VSIVGMPGLG KTTLAKKLYR HVRDQFESSG LVYVSQQPRA GEILRDIARQ VGLFKEERKE
241 NLEGNLRSLL KYKRYVILLD DIWDVEIWDD LKLVLPRCDS RIGGRIIITS RNSNYGRYIG
301 GDFSIHMLQP LDSENSFELF TKKIFTPDNN NNWANASPDL VDIGKSIVGR CGGIPLAIVV
361 TAGMLRARER TERAWNRVLE SHGHKVQDSC AKVLALSYND LPIALRPCFL YLGLFPEDHE
421 IRAFDLTNMW IAEKLIVVRS GNGREAESLA EDVLNDFVSR NLIQVSQRKC NCRISSYRIR
481 OLDRSLCVEL GKESNFFHTE RNAFGDPDNV ARVRKITFYS DNNAMSKFER SNPKPKLEKA
541 LKCFTNLDSC IFSHLAHRDF KLLQVLVVVI SYNWLSVGIS NKFGKHSCLR YLRLEGSIVG
601 ELSNSIVKLK RVETIDIAGD NIKIFCGVWE SKQLRHLRNR ERRRYFFSVS PFCLNMYRLP
661 PNRLQTLVWH DDKFFEPRLL HRLINLRKLG IWGTSDSTIK ILSALSPVPT ALEVLKLYFL
721 RDLSEQINLS TYPNIVKLNL QGFVRVRLNS EAFPPNLVKL ILDKIEVEGR VVANLKKLFT
781 LRILKMYGCK HNSEKMDLSG DGDGDSFPQL EVLRIERPFP LPEITCTDDD SMPKLKKLLL
841 TTSNVRLSER LAKLRV*
```

SEQ. ID. 6 = AMINO ACID SEQUENCE OF *Rpi-nrs1*

```
  1 MRYCVYKTWA VDSNTKANST SFLSFFSYFP FLILTFRKKK FNEKLKEHAE ILLTAVINKS
 61 IEIAGNVLPQ EGTRLVWLRE DIDWLQREHR HIRSYVDNAK AKEVGGDSRV KNLLKDIQQL
121 AGDVEDLLDE FLPKIQQSNK FICCLKTVSF ADEFAMEIEK IKRRVADIDR VRTTYSITDT
181 SNNNDDCIPL DRRRLFLHAD ETEVIGLEDD FNTLQARDLD HDLPYGVVSI VGMPGLGKTT
241 LAKKLYRHVC HQFECSGLVY VSQQPRAGEI LHDIAFQVGL TEEERKENLE NNLRSLLKIK
301 RYVILLDDIW DVEIWDDLKL VLPECDSKIG SRIIITSRNS NVGRYIGGDF SIHVLQPLDS
361 EKSFELFTKK IFNFVNDNWA NASPDLVNIG RCIVERCGGI PLAIVVTAGM LRARGRTEHA
421 WNRVLESMAH KIQDGCGKVL ALSYNDLPIA LRPCFLYFGL YPEDHEIRAF DLTNSWIEEK
481 LIVVNTGNGR EABSLADDVL NDLVSRNLIQ VAKRTYDGRI SSCRIHDLLH SLCVDLAKES
541 NFFHTEHYAF GDPSNVARVR RITFYSDDNA MNEFFHLNPK PRKLRSLFCF TKDRCIFSQM
601 AHLNFKLLQV LVVVHSQKGY QHVTFPKKIG NMSCLRYVRL EGAIRVKLPN SIVKLKCLET
661 LDIFHSSSKL PFGVWESKIL RHLCYTEECY CVSFASPFCR IMPPPNLQTL HRVDDKPCEP
721 RLLHRLINLR TLCIMDVSGS TIKILSALSP VPKALEVLKL RFFKNTSEQI NLSSHPNIVE
781 LGLVGFSAML LNIEAFFPNL VKLNLVGLMV DGHLLAVLKK LPKLRILILL WCRHDAEKMD
841 LSGDSFPQLE VLYIEDAQGL SEVTCMDDMS MPKLKKLFLV QGPNICPISL RVSERLAKLR
901 ISQVL*
```

LATE BLIGHT RESISTANCE GENES AND METHODS

CROSS-REFERENCE TO RELATED APPLICATIONS

This patent application is a national stage filing under 35 U.S.C. 371 of International Application No. PCT/GB2008/002469, filed on Jul. 18, 2008, which claims foreign priority benefits to United Kingdom Patent Application No. 0714241.7, filed on Jul. 20, 2007. These applications are incorporated herein by reference in their entireties.

FIELD OF THE INVENTION

Novel genes, compositions and methods for enhancing crop resistance to late blight.

BACKGROUND OF THE INVENTION

Potato (*Solanum tuberosum* L.) is the fourth most important crop and the most important non-cereal food crop in the world. In potato cultivation, the major natural factor which limits yield is late blight caused by the oomycete pathogen *Phytophthora infestans* (Mont.) de Bary. This devastating disease can result in complete loss of crop yield unless controlled (Świeżyński and Zimnoch-Guzowska 2001). Fungicide treatment is currently the most common method to control late blight. However, the high cost of fungicide application is problematic, especially in developing countries. Moreover, because fungicide application can impact on health and environmental safety, the use of the chemicals is becoming restricted. In addition, the pathogen quickly evolves and some of the new variants are insensitive to commonly used fungicides (Day and Shattock 1997; Goodwin et at 1996). Therefore, the introduction of genetic resistance into cultivated potato is considered a valuable method to achieve durable resistance to late blight.

Two main types of resistance to late blight have been described in potato (Umaerus and Umaerus 1994). First, general resistance is often based on a major quantitative trait loci (QTL) and a few minor QTLs and results in partial resistance. Second, specific resistance is based on major dominant resistance (R) genes. In early breeding programs during the first half of last century, 11 R genes (R1-R11) derived from *S. demissum* were identified. Nine R genes, R3 (now separated as R3a and R3b) and R5-R11 were localized on chromosome 11 (Bradshaw et al. 2006; El-Kharbotly 1994, 1996; Huang et al. 2004; Huang 2005). Other R genes originating from *S. demissum* were mapped to different locations including R1 on chromosome 5 (El-Kharbotly et al. 1994; Leonards-Schippers et al. 1992) and R2 on chromosome 4 (Li et al., 1998). All R genes introgressed from *S. demissum* to cultivated potatoes have been overcome by the pathogen as new strains rapidly evolve that are virulent on the previously resistant hosts (Umaerus and Umaerus 1994). Consequently, partial resistance conferred by QTLs was thought to be more durable than resistance conferred by single R genes (Turkensteen 1993). However, partial resistance is strongly correlated with maturity type and makes resistance breeding more difficult (Wastie 1991). Also the genetic positions of QTLs often correspond to the region of R gene clusters (Gebhart and Valkonen 2001; Grube et al. 2000).

Hence, recent efforts to identify late blight resistance have focused on major R genes conferring broad-spectrum resistance derived from diverse wild *Solanum* species. Beside *S. demissum*, other wild *Solanum* species such as *S. acaule, S. chacoense, S. berthaultii, S. brevidens, S. bulbocastanum, S. microdontum, S. sparsipilum, S. spegazzinii, S. stoloniferum, S. sucrense, S. toralapanum, S. vernei* and *S. verrucosum* have been reported as new sources for resistance to late blight (reviewed by Jansky 2000; Hawkes 1990). To date, three R genes, RB/Rpi-blb1, Rpi-blb2 and Rpi-blb3 from *S. bulbocastanum* have been mapped on chromosome 8, 6 and 4, respectively (Nasess et al. 2000; Park et al. 2005a; van der Vossen et al. 2003, 2005). Another R gene, Rpi-abpt, probably from *S. bulbocastanum*, has been localized on chromosome 4 (Park et al. 2005b). Rpi1 from *S. pinnatisectum* on chromosome 7 (Kuhl et al. 2001), Rpi-mcq1 from *S. mochiquense* (Smilde et al. 2005) and Rpi-phu1 from *S. phureja* on chromosome 9 (Śliwka et al. 2006) have also been reported.

It is evident from a review of the existing art in this area that a significant need remains for novel genes, compositions and methods for conferring late blight resistance. In this patent disclosure, we meet this need by screening wild *Solanum* species and by cloning, and introducing and expressing novel Rpi resistance genes into potato.

SUMMARY OF THE INVENTION

We have isolated, identified and characterised several different late blight R genes derived from the potato wild species *S. okadae* plus also from *S. mochiquense* and *S. neorossii*.

This invention provides novel gene sequences, compositions and methods for enhancing the resistance in crops, in particular but not limited to, potato, to late blight caused by the oomycete pathogen *Phytophthora infestans*.

BRIEF DESCRIPTION OF THE DRAWINGS

FIG. 7 Alignment of the deduced protein sequences of Rpi-oka1 (SEQ ID NO: 4), Rpi-oka2 (SEQ ID NO: 12) and Tm-2² (SEQ ID NO: 14). The complete amino acid sequence of Rpi-oka1 is shown and dots indicate identical residues in the other two proteins. Where residues from Rpi-oka2 and Tm-2² differ from Rpi-oka1, the residues in these proteins are given. The two amino acid differences between Rpi-oka1 and Rpi-oka2 are indicated in bold type. Predicted coiled coil domains are underlined and the first and fourth hydrophobic residues of each heptad repeat are double-underlined. Conserved motifs within the NB-ARC domain are indicated in lower case italics. Putative leucine-rich repeats (LRRs) are indicated above the sequence line.

FIG. 8 Alignment of Rpi-oka1 (SEQ ID NO: 4), Rpi-nrs1 (SEQ ID NO: 16) and Tm-$2^2$ (SEQ ID NO: 15) protein sequences. The CC, NB-ARC and LRR domains are highlighted in red, green and orange respectively. Conserved motifs within the NB-ARC domain are underlined in italic.

FIG. 12 provides nucleic acid and amino acid sequences of the indicated genes and proteins.

DETAILED DISCLOSURE OF THE PREFERRED EMBODIMENTS OF THE INVENTION

Figure 1:
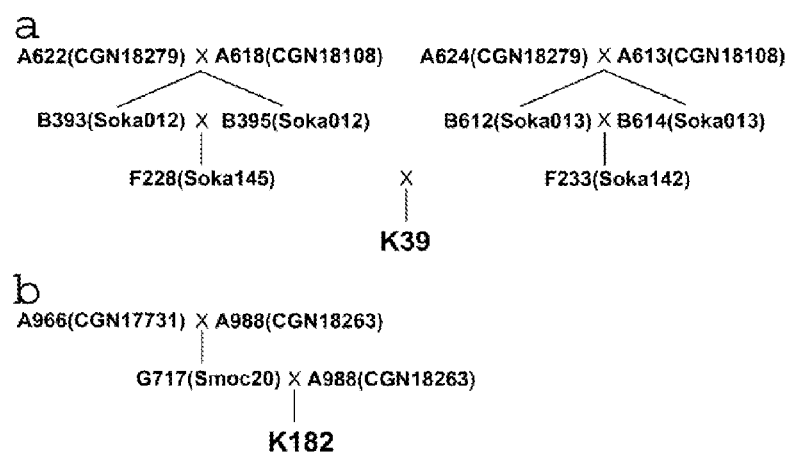
FIG. 1 Pedigrees of the genotypes used to construct BAC libraries. (a): K39 and (b): K182

The following sequences are annexed hereto as FIG. 12:

| Seq ID | Rpi Sequence |
|---|---|
| 1 | oka1 nt |
| 7 | oka2 nt |
| 8 | oka1 transgene inc. promoter and terminator from pSLJ21152 nt |
| 2 | mcq1.1 nt |
| 9 | mcq1.2 nt |
| 10 | mcq1.1 transgene inc. promoter and terminator from pSLJ21153 nt |
| 11 | mcq1.2 transgene inc. promoter and terminator from pSLJ21148 nt |
| 3 | nrs1 nt |
| 4 | oka1 aa |
| 12 | oka2 aa |
| 5 | mcq1.1 aa |
| 13 | mcq1.2 aa |
| 6 | nrs1 aa |

(nt = nucleotide sequence, aa = polypeptide sequence)

The above sequences represent extended sequences compared to those disclosed in GB0714241.7 from which the present application claims priority. Specifically, they have been extended as follows:
SEQ ID 1a—extended by 99 additional bases at beginning
SEQ ID 1b—extended by 141 additional bases at beginning
SEQ ID 3—extended by the same 141 ditional bases at beginning
SEQ ID 4a—extended by 33 additional amino acids at beginning
SEQ ID 4b—extended by 47 additional amino acids at beginning
SEQ ID 6—extended by the same 47 additional amino acids at beginning Nevertheless that earlier subject matter is not abandoned. Thus where any aspect or embodiment of the present invention is disclosed in respect of the extended sequences defined above, it should be understood as applying mutatis mutandis the earlier shorter sequence. Thus each and everyone of such aspects or embodiments of the invention will apply mutatis mutandis also to:
SEQ ID 1a—nucleotides 100-2676
SEQ ID 1b—nucleotides 142-2718
SEQ ID 3—nucleotides 142-2718
SEQ ID 4a—amino acids 34-891
SEQ ID 4b—amino acids 48-905
SEQ ID 6—amino acids 48-905

The following sequences are expression cassettes including some of the above sequences:
In SEQ ID 1c (Rpi-oka1)—the Rpi-oka1 promoter is included within the bases 1-709, including a 5' untranslated region (UTR) from bases 627-709. The Rpi-oka1 open reading frame (ORF) is present at bases 710-3382 and the terminator from base 3383 onwards. This was cloned into pSLJ21152 and then used to transform *S. tuberosum* and *S. lycopersicum* to confer resistance against *P. infestans.*
SEQ ID 2b (Rpi-mcq1.1)—The Rpi-mcq1.1 promoter is included within the bases 1-2262, the Rpi-mcq1.1 open reading frame (ORF) is present at bases 2263-4848 and the terminator from base 4849 onwards. This was cloned into pSLJ21153 and then used to transform *S. tuberosum* and *S. lycopersicum* to confer resistance against *P. infestans.*
SEQ ID 2d (Rpi-mcq1.2)—The Rpi-mcq1.2 promoter is included within the bases 1-1999, the Rpi-mcq1.2 open reading frame (ORF) is present at bases 2000-4567 and the terminator from base 4568 onwards. This was cloned into pSLJ21148 and then used to transform *S. tuberosum* and *S. lycopersicum* to confer resistance against *P. infestans.*

As shown in FIG. 8, the Rpi-oka1 and Rpi-nrs1 sequences are extremely closely related.

As described below, it is believed that the sequences for Rpi-oka2 are in fact identical to Rpi-nrs1, but these are included for completeness.

However the Rpi-oka3 sequences referred to herein below are identical to Rpi-oka2, and are therefore not set out explicitly.

Finally, different candidate Rpi genes were identified from *S. mochiquense* and these are both set out in the sequences. These are both believed to be functional R genes with distinct recognition specificities.

Thus in a first aspect of the present invention there are disclosed isolated nucleic acid molecules encoding a functional Rpi gene, which may optionally be selected from *S. okadae, S. mochiquense* and *S. neorossii.*

In particular embodiments the invention provides an isolated Rpi resistance gene having a sequence provided herein as SEQ. ID. 1a, 1b, 2a, 2b or 3.

Nucleic acid molecules according to the present invention may be provided isolated and/or purified from their natural environment, in substantially pure or homogeneous form, or free or substantially free of other nucleic acids of the species of origin. Where used herein, the term "isolated" encompasses all of these possibilities.

The nucleic acid molecules may be wholly or partially synthetic. In particular they may be recombinant in that nucleic acid sequences which are not found together in nature (do not run contiguously) have been ligated or otherwise combined artificially.

Alternatively they may have been synthesised directly e.g. using an automated synthesiser.

Preferred nucleic acids consist essentially of the gene in question, optionally in an expression vector as described in more detail below.

Nucleic acid according to the present invention may include cDNA, RNA, genomic DNA and modified nucleic acids or nucleic acid analogs. Where a DNA sequence is specified, e.g. with reference to a figure, unless context requires otherwise the RNA equivalent, with U substituted for T where it occurs, is encompassed. Where a nucleic acid of the invention is referred to herein, the complement of that nucleic acid will also be embraced by the invention. The 'complement' of a given nucleic acid (sequence) is the same length as that nucleic acid (sequence), but is 100% complementary thereto.

Where genomic nucleic acid sequences of the invention are disclosed, nucleic acids comprising any one or more (e.g. 2) introns or exons from any of those sequences are also embraced.

A resistance gene in this context is one which controls resistance to the late blight caused by P. infestans. Such a gene may encode a polypeptide capable of recognising and activating a defence response in a plant in response to challenge with said pathogen or an elicitor or Avr gene product thereof.

Nucleic acids of the first aspect may be advantageously utilised, for example, in potatoes.

A nucleic acid of the present invention may encode one of the amino acid sequences described above (4a, 4b, 5a, 5b, 6) e.g. be degeneratively equivalent to the corresponding nucleotide sequences.

In a further aspect of the present invention there are disclosed nucleic acids which are variants of the sequences of the first aspect.

Equally the fragments may have utility in probing for, or amplifying, the sequence provided or closely related ones. Suitable lengths of fragment, and conditions, for such processes are discussed in more detail below.

Also included are nucleic acids which have been extended at the 3' or 5' terminus.

Sequence variants which occur naturally may include alleles or other homologues (which may include polymorphisms or mutations at one or more bases).

Artificial variants (derivatives) may be prepared by those skilled in the art, for instance by site directed or random mutagenesis, or by direct synthesis. Preferably the variant nucleic acid is generated either directly or indirectly (e.g. via one or amplification or replication steps) from an original nucleic acid having all or part of the sequences of the first aspect. Preferably it encodes a P. infestans resistance gene.

The term "variant" nucleic acid as used herein encompasses all of these possibilities. When used in the context of polypeptides or proteins it indicates the encoded expression product of the variant nucleic acid.

Some of the aspects of the present invention relating to variants will now be discussed in more detail.

Calculated nucleotide identities were as follows:

|  | Rpi-oka1 | Rpi-oka2 | Rpi-nrs1 | Rpi-mcq1.1 | Rpi-mcq1.2 |
| --- | --- | --- | --- | --- | --- |
| Rpi-oka1 |  |  |  |  |  |
| Rpi-oka2 | 98% |  |  |  |  |
| Rpi-nrs1 | 98% | 100% |  |  |  |
| Rpi-mcq1.1 | 84% | 83% | 83% |  |  |
| Rpi-mcq1.2 | 83% | 82% | 82% | 87% |  |
| Tm2-2 | 80% | 79% | 79% | 85% | 84% |

Calculated amino acid identities were as follows:

|  | Rpi-oka1 | Rpi-oka2 | Rpi-nrs1 | Rpi-mcq1.1 | Rpi-mcq1.2 |
| --- | --- | --- | --- | --- | --- |
| Rpi-oka1 |  |  |  |  |  |
| Rpi-oka2 | 98% |  |  |  |  |
| Rpi-nrs1 | 98% | 100% |  |  |  |
| Rpi-mcq1.1 | 76% | 75% | 75% |  |  |
| Rpi-mcq1.2 | 76% | 75% | 75% | 81% |  |
| Tm2-2 | 72% | 71% | 71% | 77% | 75% |

A variant nucleic acid molecule shares homology with, or is identical to, all or part of the coding sequence discussed above. Generally, variants may encode, or be used to isolate or amplify nucleic acids which encode, polypeptides which are capable of mediating a response against P. infestans, and/or which will specifically bind to an antibody raised against the polypeptides described above (4a, 4b, 5a, 5b, 6).

Variants of the present invention can be artificial nucleic acids (i.e. containing sequences which have not originated naturally) which can be prepared by the skilled person in the light of the present disclosure. Alternatively they may be novel, naturally occurring, nucleic acids, which have been or may be isolatable using the sequences of the present invention e.g. from S. mochiquense, S. okadae and S. neorossii.

Thus a variant may be a distinctive part or fragment (however produced) corresponding to a portion of the sequence provided. The fragments may encode particular functional parts of the polypeptide, e.g. LRR regions, or termini.

The above multiple comparisons were performed, using AlignX (Vector N11 Suite Invitrogen) with an engine based on the CLUSTAL matix.

More generally homology (i.e. similarity or identity) may be as defined using sequence comparisons are made using BestFit and GAP programs of GCG, Wisconsin Package 10.0 from the Genetics Computer Group, Madison, Wis. CLUSTAL is also a matrix used by BestFit. Parameters are preferably set, using the default settings, as follows: Gap Creation pen: 9; Gapext pen: 2. Homology may be at the nucleotide sequence and/or encoded amino acid sequence level. Preferably, the nucleic acid and/or amino acid sequence shares at least about 50%, or 60%, or 70%, or 80% homology, most preferably at least about 81%, 82%, 83%, 84%, 85%, 86%, 87%, 88%, 89%, 90%, 91%, 92%, 93%, 94%, 95%, 96%, 97%, 98% or 99% homology with SEQ. ID. 1a, 1b, 2a, 2b or 3 or 4a, 4b, 5a, 5b, or 6 as appropriate.

In particular the invention provides an isolated Rpi resistance gene having a sequence which is at least about 80% homologous to the nucleic acid sequence provided herein as SEQ. ID. 1a, 1b, 2a, 2b or 3.

It further provides an isolated protein having an amino acid sequence which is at least 80% homologous to the amino acid sequence provided herein as SEQ. ID. 4a, 4b, 5a, 5b, or 6. Thus a variant polypeptide in accordance with the present invention may include within the sequences shown herien, a single amino acid or 2, 3, 4, 5, 6, 7, 8, or 9 changes, about 10, 15, 20, 30, 40 or 50 changes, or greater than about 50, 60, 70, 80, 90, 100, 200, 400 changes. In addition to one or more changes within the amino acid sequence shown, a variant polypeptide may include additional amino acids at the C-terminus and/or N-terminus.

Thus in a further aspect of the invention there is disclosed a method of producing a derivative nucleic acid comprising the step of modifying the coding sequence of a nucleic acid of the present invention e.g. SEQ. ID. 1a, 1b, 2a, 2b or 3.

Changes to a sequence, to produce a derivative, may be by one or more of addition, insertion, deletion or substitution of one or more nucleotides in the nucleic acid, leading to the addition, insertion, deletion or substitution of one or more amino acids in the encoded polypeptide. Changes may be desirable for a number of reasons, including introducing or removing the following features: restriction endonuclease sequences; codon usage; other sites which are required for post translation modification; cleavage sites in the encoded polypeptide; motifs in the encoded polypeptide (e.g. binding sites). Leader or other targeting sequences may be added or removed from the expressed protein to determine its location following expression. All of these may assist in efficiently cloning and expressing an active polypeptide in recombinant form (as described below).

Other desirable mutation may be random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Also included are variants having non-conservative substitutions. As is well known to those skilled in the art, substitutions to regions of a peptide which are not critical in determining its conformation may not greatly affect its activity because they do not greatly alter the peptide's three dimensional structure.

In regions which are critical in determining the peptides conformation or activity such changes may confer advantageous properties on the polypeptide. Indeed, changes such as those described above may confer slightly advantageous properties on the peptide e.g. altered stability or specificity. For instance, the manipulation of LRR regions of the polypeptides encoded by the nucleic acids of the present invention may allow the production of novel resistance specificities e.g. with respect to P. infestans isolates.

LRR regions may also be grafted on to other NBS regions (e.g. from other resistance genes). Thus methods for generating novel specificities may include mixing or incorporating sequences from related resistance genes into the Rpi sequences disclosed herein. An alternative strategy for modifying Rpi sequences would employ PCR as described below (Ho et al., 1989, Gene 77, 51-59) or DNA shuffling (Crameri et al., 1998, Nature 391).

A detailed analysis of some of the ORFs of the present invention is provided in the Examples below, including the existence of variants having substitutions, and identification of regions of interest.

In a further aspect of the present invention there is provided a method of identifying and/or cloning a nucleic acid variant from a plant which method employs a distinctive Rpi nucleotide sequence (e.g. as present in SEQ. ID. 1A, 1B, 2A, 2B or 3 or the complement thereof, or degenerate primers based thereon).

An oligonucleotide for use in probing or amplification reactions comprise or consist of about 30 or fewer nucleotides in length (e.g. 18, 21 or 24). Generally specific primers are upwards of 14 nucleotides in length. For optimum specificity and cost effectiveness, primers of 16-24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

Preferably the probe/primer is distinctive in the sense that it is present in all or some of the Rpi sequences disclosed herein, but not in resistance gene sequences of the prior art.

For instance, the functional allele data presented herein (see e.g. FIG. 10 or FIG. 11) permits the identification of functional Rpi alleles as follows.

In a further embodiment, a variant in accordance with the present invention is also obtainable by means of a method which includes:

(a) providing a preparation of nucleic acid, e.g. from plant cells, (b) providing a nucleic acid molecule which is a probe as described above, (c) contacting nucleic acid in said preparation with said nucleic acid molecule under conditions for hybridisation of said nucleic acid molecule to any said gene or homologue in said preparation, and identifying said gene or homologue if present by its hybridisation with said nucleic acid molecule.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter or nylon. Labelled probe may be hybridised to the DNA fragments on the filter and binding determined. DNA for probing may be prepared from RNA preparations from cells.

Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.), such as is described hereinafter. Probing may optionally be done by means of so-called "nucleic acid chips" (see Marshall & Hodgson (1998) Nature Biotechnology 16: 27-31, for a review).

Preliminary experiments may be performed by hybridising under low stringency conditions. For probing, preferred conditions are those which are stringent enough for there to be a simple pattern with a small number of hybridisations identified as positive which can be investigated further.

For instance, screening may initially be carried out under conditions, which comprise a temperature of about 37° C. or less, a formamide concentration of less than about 50%, and a moderate to low salt (e.g. Standard Saline Citrate ("SSC")= 0.15 M sodium chloride; 0.15 M sodium citrate; pH 7) concentration.

Alternatively, a temperature of about 50° C. or less and a high salt (e.g. "SSPE" 0.180 mM sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid.

Suitable conditions include, e.g. for detection of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

It is well known in the art to increase stringency of hybridisation gradually until only a few positive clones remain. Suitable conditions would be achieved when a large number of hybridising fragments were obtained while the background hybridisation was low.

Using these conditions nucleic acid libraries, e.g. cDNA libraries representative of expressed sequences, may be searched. Those skilled in the art are well able to employ suitable conditions of the desired stringency for selective hybridisation, taking into account factors such as oligonucleotide length and base composition, temperature and so on. One common formula for calculating the stringency conditions required to achieve hybridization between nucleic acid molecules of a specified sequence homology is (Sambrook et al., 1989):

$T_m$=81.5° C.+16.6 Log [Na+]+0.41 (% G+C)−0.63 (% formamide)−600/# bp in duplex. As an illustration of the above formula, using [Na+]=[0.368] and 50-% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (see below) or RN'ase cleavage. The identification of successful hybridisation is followed by isolation of the nucleic acid which has hybridised, which may involve one or more steps of PCR or amplification of a vector in a suitable host.

Thus one embodiment of this aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a product able to influence a resistance characteristic of a plant, particularly an Rpi-resistance response.

In a further embodiment, hybridisation of nucleic acid molecule to a variant may be determined or identified indirectly, e.g. using a nucleic acid amplification reaction, particularly the polymerase chain reaction (PCR) (see "PCR protocols; A Guide to Methods and Applications", Eds. Innis et al, Academic Press, New York, (1990)).

The methods described above may also be used to determine the presence of one of the nucleotide sequences of the present invention within the genetic context of an individual plant. This may be useful in plant breeding programmes e.g. to directly select plants containing alleles which are responsible for desirable traits in that plant species, either in parent plants or in progeny (e.g hybrids, F1, F2 etc.).

As used hereinafter, unless the context demands otherwise, the term "Rpi nucleic acid" is intended to cover any of the nucleic acids of the invention described above, including functional variants.

In one aspect of the present invention, the Rpi nucleic acid described above is in the form of a recombinant and preferably replicable vector. "Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eucaryotic (e.g. higher plant, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter.

Thus this aspect of the invention provides a gene construct, preferably a replicable vector, comprising a promoter operatively linked to a nucleotide sequence provided by the present invention, such as SEQ. ID. 1a, 1b, 2a, 2b or 3 or a variant thereof.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press (or later editions of this work).

Many known techniques and protocols for manipulation of nucleic acid, for example in preparation of nucleic acid constructs, mutagenesis (see above discussion in respect of variants), sequencing, introduction of DNA into cells and gene expression, and analysis of proteins, are described in detail in *Current Protocols in Molecular Biology,* Second Edition, Ausubel et al. eds., John Wiley & Sons, 1992. The disclosures of Sambrook et al. and Ausubel et al. are incorporated herein by reference.

In one embodiment of this aspect of the present invention, there is provided a gene construct, preferably a replicable vector, comprising an inducible promoter operatively linked to a nucleotide sequence provided by the present invention. The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Particular of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy R R D ed) Oxford, BIOS Scientific Publishers, pp 121-148).

Suitable promoters which operate in plants include the Cauliflower Mosaic Virus 35S (CaMV 35S). Other examples are disclosed at pg. 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

Purely by way of example, SEQ. ID. 1c, 2c and 2d show the nucleotide sequences of oka1, mcq1.1 and mcq1.2 and include promoter and terminator sequences that may be used in contstructs used to transform both potato and tomato.

It may be desirable to use a strong constitutive promoter. If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising introduction of such a construct into a host cell, particularly a plant cell.

In a further aspect of the invention, there is disclosed a host cell containing a heterologous construct according to the present invention, especially a plant or a microbial cell. The term "heterologous" is used broadly in this aspect to indicate that the gene/sequence of nucleotides in question (an Rpi gene) have been introduced into said cells of the plant or an ancestor thereof, using genetic engineering, i.e. by human intervention. A heterologous gene may replace an endogenous equivalent gene, i.e. one which normally performs the same or a similar function, or the inserted sequence may be additional to the endogenous gene or other sequence.

Nucleic acid heterologous to a plant cell may be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homolog is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

The host cell (e.g. plant cell) is preferably transformed by the construct, which is to say that the construct becomes established within the cell, altering one or more of the cell's characteristics and hence phenotype e.g. with respect to *P. infestans*.

Nucleic acid can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

Purely by way of example, transformation strategies for potato, tomato, and tobacco are set out in Example 6 hereinafter. Other strategies, particularly those applicable to the genus *Solanum*, are well known to those skilled in the art (see e.g. Mansure and Magioli, Acta Botanica Brasilica, 2005 (Vol. 19) (No. 1) 139-148). The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration. Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Generally speaking, following transformation, a plant may be regenerated, e.g. from single cells, callus tissue or leaf discs, as is standard in the art. Almost any plant can be entirely regenerated from cells, tissues and organs of the plant.

Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

Plants which include a plant cell according to the invention are also provided.

In addition to the regenerated plant, the present invention embraces all of the following: a clone of such a plant, selfed or hybrid progeny and descendants (e.g. F1 and F2 descendants) and any part of any of these. The invention also provides parts of such plants e.g. any part which may be used in reproduction or propagation, sexual or asexual, including cuttings, seed and so on, or which may be a commodity per se e.g. tuber.

The invention further provides a method of influencing or affecting the degree of resistance of a plant to a pathogen, particularly *Phytophthora infestans*, more particularly to any of the isolates discussed herein, the method including the step of causing or allowing expression of a heterologous nucleic acid sequence as discussed above within the cells of the plant.

The step may be preceded by the earlier step of introduction of the nucleic acid into a cell of the plant or an ancestor thereof.

Preferred plants for transformation are of the family Solanaceae, more preferably genus *Solanum*. Optionally the plant may be *S. tuberosum* or *S. lycopersicum*

The methods may also include the manipulation of other genes e.g. which may be involved in transduction of the resistance signal, or in generating a resistance response.

Thus provided are methods of influencing or affecting the degree of resistance of a plant to *P. infestans*, the method including the step of causing or allowing expression of a heterologous nucleic acid as described above within the cells of the plant.

In preferred methods more than one Rpi gene is introduced into the plant. In other strategies, a plurality of plants is provided each having a different endogenous or heterologous Rpi gene (wherein at least one of said plants includes a heterologous Rpi gene of the present invention i.e. has been generated by the technical methods described above). The plurality of plants may be planted together in a single area such as to maximise the extent or durability of the crop's resistance to *P. infestans*. Alternatively the plurality of plants may be planted successively in the area (e.g. on a rotation) to achieve the same effect.

The foregoing discussion has been generally concerned with uses of the nucleic acids of the present invention for production of functional Rpi polypeptides in a plant, thereby increasing its pathogen resistance. Purely for completeness it is noted that the information disclosed herein may also be used to reduce the activity or levels of such polypeptides in cells in which it is desired to do so (e.g. in an experimental model). Nucleic acids and associated methodologies for carrying out down-regulation (e.g. complementary sequences) form one part of the present invention.

As noted above the present invention also encompasses the expression product of any of the Rpi (particularly functional Rpi) nucleic acid sequences disclosed above, plus also methods of making the expression product by expression from encoding nucleic acid therefore under suitable conditions, which may be in suitable host cells.

A preferred polypeptide includes the amino acid sequence shown in SEQ. ID. 4a, 4b, 5a, 5b, or 6. However a polypeptide according to the present invention may be a variant (allele, fragment, derivative, mutant or homologue etc.) of these polypeptides.

Also encompassed by the present invention are polypeptides which although clearly related to a functional Rpi polypeptides (e.g. they are immunologically cross reactive with the polypeptide, or they have characteristic sequence motifs in common with the polypeptide) no longer have Rpi function.

Following expression, the recombinant product may, if required, be isolated from the expression system. Generally however the polypeptides of the present invention will be used in vivo (in particular in planta).

Purified Rpi or variant proteins of the invention, produced recombinantly by expression from encoding nucleic acid therefor, may be used to raise antibodies employing techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80-82). Antibodies may be polyclonal or monoclonal. As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide with Rpi function (in accordance with embodiments disclosed herein), including screening candidate peptides or polypeptides with a polypeptide including the antigen-binding domain of an antibody (for example whole antibody or a fragment thereof) which is able to bind an Rpi peptide, polypeptide or fragment, variant or variant thereof or preferably has binding specificity for such a peptide or polypeptide, such as having an amino acid sequence identified herein.

Specific binding members such as antibodies and polypeptides including antigen binding domains of antibodies that bind and are preferably specific for polypeptides of the sequence SEQ. ID. 4a, 4b, 5a, 5b, or 6 or a mutant, variant or derivative thereof represent further aspects of the present invention, as do their use and methods which employ them.

The above description has generally been concerned with the translated and coding parts of Rpi genes. Also embraced within the present invention are untranscribed parts (UTRs) of the genes.

Thus a further aspect of the invention is an isolated nucleic acid molecule encoding the promoter, or other UTR (3' or 5'), of an Rpi gene described herein.

As noted above, SEQ. ID. 1c, 2c and 2d show the nucleotide sequences of oka1, mcq1.1 and mcq1.2 and include promoter and terminator sequences that may be used in constructs used to transform both potato and tomato.

In summary, it can be seen that the present inventors have isolated, identified and characterised several different late blight R genes derived from the potato wild species *S. okadae* plus also from *S. mochiquense* and *S. neorossii*. Accordingly this invention provides novel gene sequences, compositions and methods for enhancing the resistance in crops, in particular but not limited to, potato, to late blight caused by the oomycete pathogen *Phytophthora infestans*.

In order to clone these late blight R genes a variety of methodologies were innovatively combined. As set out in more detail in the Examples below we constructed two BAC libraries from genomic DNA of the two species. In this patent disclosure, we describe the construction and analysis of the two BAC libraries. Furthermore, we identify and characterize BAC clones linked to late blight R genes using PCR-based markers developed during preliminary mapping experiments. This process has facilitated fine-scale mapping of the R genes, chromosome walking toward the target genes, physical mapping and finally gene cloning.

Construction of libraries with large genomic DNA inserts is one of the essential steps for map-based gene cloning strategies. Several methods have been developed for the construction of libraries, including yeast artificial chromosome (YAC), P1-derived artificial chromosome (PAC), plasmid-based clone (PBC), plant transformation-competent artificial chromosome (TAC), bacterial artificial chromosome (BAC) and binary bacterial artificial chromosome (BIBAC) (cited in Feng et al. 2006). During the last few years, BAC libraries have been constructed from a wide variety of plant species including the staple crops rice, wheat and potato (Tao et al. 2002; Nilmalgoda et al. 2003; Chen et al. 2004), and other species such as peach, garlic, banana, sugar beet, soybean, peanut and sunflower (Georgi et al. 2002; Lee et al. 2003; Vilarinhos et al. 2003; McGrath et al. 2004; Wu et al. 2004; Yüksel et al. 2005; Bouzidi et al. 2006; Feng et al. 2006).

We have been working to isolate genes from wild species *S. okadae* and *S. mochiquense* conferring resistance to late blight in potato using a map-based gene cloning approach. The gene derived from *S. mochiquense* has already been reported, albeit that it was not previously isolated (Smilde et al. 2005) and recently the genes derived from *S. okadae* have been identified (Foster et al. unpublished data). As a step towards map-based cloning of these R genes, we constructed two BAC libraries from K39 containing Rpi-oka1 and Rpi-oka2 and K182 containing Rpi-mcq1. To construct high-quality BAC libraries, it is crucial to optimize partial digestion conditions and to accurately size-select partially digested DNA fragments. Smaller fragments often produce smaller insert clones with higher transformation efficiency, but larger fragments often result in higher percentages of clones lacking inserts and lower transformation efficiency (Feng et al. 2006). In this study, fragments of 100-200 Kb were selected for the BAC libraries.

The size of the haploid *Solanum* species ranges from 800 Mb to 1,200 Mb depending on species. Arumuganathan and Earle (1991) reported that the haploid genome size of *S. berthaultii* is 840 Mb and that of *S. tuberosum* is 800-930 Mb. In the present study, a total of 105,216 and 100,992 BAC clones with average insert sizes of 103.5 Kb and 85.5 Kb were obtained for the K39 and K182 libraries, respectively. Assuming a potato haploid genome size of 1,000 Mb, we estimate that these libraries contain approximately 10.9 and 8.6 genome equivalents for the K39 and K182 libraries, respectively. Although we selected the DNA fragments in the range of 100-200 Kb, the average insert sizes of both libraries is smaller than expected. This discrepancy has been observed by others (Danesh et al. 1998; Meksem et al. 2000; Yuksel and Paterson 2005) and could be caused by the presence of smaller fragments that were not fully removed in the size-selection steps as suggested by Frijters et al. (1997). Given the genome coverage, we expected that all regions of the genome should be well represented. We tested this using PCR-based markers known to be linked to the R genes Rpi-oka1, Rpi-oka2 and Rpi-mcq1.

In order to minimize the number of PCR reactions required, we used a pooling strategy for screening of the libraries. Previously several different pooling strategies have been employed for screening BAC libraries (Klein et al. 2000; Ozdemir et al. 2004; Bouzidi et al. 2006). In our study, we used a plate pooling strategy combined with a column and row pooling strategy within plate pools. Each 384-well plate was pooled and plasmid DNA from each pool was prepared. Based on the genome equivalents of each library, theoretically we expected that 11 and 9 pools would be positive to a particular marker and that half of these pools, after digestion with restriction enzymes to identify resistant allele-specific markers would contain BAC clones from the haplotype corresponding to each gene.

The positive BAC clones in the K39 and K182 libraries to PCR-based markers were consistent with or slightly better than estimated genome equivalents and were identified with average numbers of 15 and 12.5, respectively. Both are slightly more than numbers expected based on estimate of the genome equivalents. These could be caused by over-estimation of the potato haploid genome size or under-estimation of the average insert sizes of the BAC clones obtained. On the other hand, the BAC libraries we constructed could be biased due to an over- or under-representation of HindIII sites within our region of interest. In order to achieve better representation, others have used two or three different restriction enzymes, rich in either NT or G/C when they constructed BAC libraries (Chang et al. 2001; Tao et al. 2002; Chen et al. 2004).

Based on the results of BAC screening with PCR markers linked to the Rpi genes, we sequenced the BAC-ends of eight single BAC clones for each library. Of these, one identified from each of the K39 and K182 libraries was similar to Tm-$2^2$, the tomato mosaic virus R gene on tomato chromosome 9 (Lanfermeijer et al. 2003). Additionally two other BAC end sequences from the K182 library were similar to several different resistance proteins. These results combined with the genetic linkage maps of Rpi-oka1, Rpi-oka2 and Rpi-mcq1 constructed in our complementary researches (Foster et al. unpublished; Zhu et al. unpublished) indicated that we had identified BAC clones that covered the genomic region containing the genes.

Large-insert BAC libraries are a valuable tool for chromosome walking, BAC contig construction and physical mapping in regions containing R genes. Although we haven't yet identified the precise physical location of the R genes, as shown in the results of BAC screening by the PCR-based approach and BAC-end sequences of selected BAC clones, the construction of BAC libraries covering 10.9- and 8.6-fold of the potato haploid genome from *S. okadae* and *S. mochiquense* has facilitated the cloning of the Rpi genes and will be of value for further potato genomic studies which require map-based cloning steps.

Having generally disclosed this invention, including methods of making and using compositions useful in conferring late blight resistance, the following examples are provided to further the written description and fully enable this invention, including its best mode and equivalents thereof. However, those skilled in the art will appreciate that the invention which these examples illustrate is not limited to the specifics of the examples provided here. Rather, for purposes of apprehend-

EXAMPLES

Example 1

**Construction of Bac Libraries from the Wild Potato Species *Solanum okadae* and *Solanum mochiquense* and the Identification of Clones Near Late Blight Resistance Loci** a. Plant Materials

The pedigrees of the plants used to construct the two BAC libraries are shown in FIG. 1. The *S. okadae* plant K39 is a transheterozygote carrying both Rpi-oka1 originally from the parent A618 and Rpi-oka2 from A624 (Foster et al. unpublished data). The *S. mochiquense* plant K182 is heterozygous for Rpi-mcq1 (formerly named Rpi-moc1; Smilde et al. 2005) and was obtained from a BC1 population.

b. Preparation of High-Molecular-Weight Insert DNA

A method used for high-molecular-weight (HMW) DNA preparation was slightly modified from Liu and Whittier (1994) and Chalhoub et al. (2004). Plant materials were grown on Murashige and Skoog (MS) medium without sucrose in vitro and young leaf tissues were harvested and stored at −80° C. Twenty grams frozen leaf tissue was used to prepare DNA plugs containing HMW DNA. The DNA plugs were prepared in 0.7% in Cert agarose (Biozym, Oldendorf, Germany), washed in lysis buffer solution (1% sodium lauryl sarcosine, 0.2 mg/ml proteinase K and 3.8 mg/ml sodium diethyldithiocarbamate dissolved in 0.5 M EDTA, pH 8.5) and stored at 4° C. in 0.5 M EDTA until required without decreasing DNA quality as suggested by Osoegawa et al. (1998). The stored plugs were soaked in TE buffer, chopped into small pieces and partially digested with 5 units of HindIII for 1 hour based on the results of prior optimisation experiments which showed that these conditions generated DNA of a size range 50-300 kb.

Triple size selection was used to improve the size and uniformity of the inserts as described in Chalhoub et al. (2004). The first size selection was performed on 1% Seakem LE agarose (Biozym, Oldendorf, Germany) using clamped homogeneous electric field (CHEF) pulsed field gel electrophoresis (Bio-rad, Hercules, USA) at 1-40 seconds, 120°, 16 hours and 200 V in 0.25×TBE buffer directly followed by the second size selection in the same gel at 4-5 seconds, 120°, 6 hours and 180 V in the same buffer. The regions of gel containing partially digested DNA between 100 and 200 Kb were excised and divided into two. For the third size selection, the excised gel slices were separately run on 1% Sea Plaque GTG Low-melting point agarose (Biozym, Oldendorf, Germany) at 3-4.5 seconds, 120°, 14 hours and 180 V. Size-selected DNA fragments were excised from the gel and stored at 4° C. in 0.5 M EDTA (pH 8). DNA was recovered in 40 µl 1×TAE buffer by electro-elution using a BioRad Electro-elution system (Bio-rad, Hercules, USA).

c. BAC Library Construction

Ligation and transformation were performed according to the methods described in Allouis et al. (2003) and Chalhoub et al. (2004) with some modification. The total eluted DNA from the size-selected DNA fragment was ligated in a 100 µl reaction with 10 ng pindigoBAC-5 vector (EpiCentre Biotechnologies, Madison, USA) and 800 U T4 DNA ligase (New England Biolabs, Ipswich, USA). The ligation was dialysed on 0.5×TE buffer for 3 hours using Millipore membrane (Millipore, Billerica, USA). Three microliter of dialysed ligation was mixed with 20 µl ElectroMax DH10B electrocompetent cells (Invitrogen, Paisley, UK), incubated for 1 minute on ice and electroporated at 180 V, 200 ohms and 25 µF. Transformed cells were recovered in 1 ml of SOC medium (Invitrogen, Paisley, UK), incubated at 37° C. for 1 hour, plated on selective LB medium with 17 µg/ml chloramphenicol, 125 µg/ml IPTG (isopropylthio-β-D-galactoside) and 100 µg/ml X-Gal (5-bromo-4-chloro-3-indolyl-(β-D-galactoside) and grown at 37° C. overnight. White colonies were picked into 384-well microtiter plates (Genetix Ltd., Dorset, UK) containing Freezing broth (1% Tryptone, 0.5% Yeast Extract, 0.5% NaCl, 0.63% $K_2HPO_4$, 0.045% Sodium Citrate, 0.009% $MgSO_4$, 0.09% $(NH_4)_2SO_4$, 0.18% $KH_2PO_4$, 4.4% Glycerol and 17 µg/ml chloramphenicol, pH 7.2) using a Q-Pix instrument (Genetix Ltd., Dorset, UK), incubated at 37° C. overnight and stored at −80° C.

d. BAC Insert Sizing

To determine the insert size of the BAC clones, randomly selected BAC clones were cultured in 3 ml LB containing 17 µg/ml chloramphenicol at 37° C. overnight. BAC DNA was isolated using the method slightly modified from the Qiagen plasmid midi kit (Qiagen Ltd, Crawley, UK) and digested with NotI for 3 hours to release the insert DNA from the vector. Digested DNA was separated on a 1% agarose gel using CHEF gel electrophoresis (Bio-rad, Hercules, USA) at 5-15 seconds, 120°, 16 hours and 200 V in 0.5×TBE buffer.

e. BAC Library Screening and BAC Clone Characterization

The BAC clones stored in separate 384-well plate were pooled and plasmid DNA from each pool was prepared. The pooled-DNA was screened with eight PCR-based markers (Table 1a) known to be linked to the identified Rpi genes. Once positive pools were identified using particular marker primers, the original 384-well library plate of the library was replicated onto solid LB medium using a high density replicator tool and rows and columns of clones were screened by PCR using the same primers to select single positive clones. Selected positive clones were BAC-end sequenced using Big Dye v. 3.1 cycle sequencing reagents (Applied Biosystems, Foster City, USA). Sequencing reactions were run on an ABI 3730 at the John Innes Centre Genome Laboratory (Norwich, UK).

In addition, the pooled plasmid DNA from the BAC pools of the K39 library was spot-blotted onto Hybond-N+ membrane and probed by hybridisation with $^{32}P$-labelled okaNBS-Hae marker as a probe. The 384-well BAC plates corresponding to the pools identified using this probe were then double spotted onto Hybond-N+ membrane and hybridised to the same probe to identify individual BAC clones from the pools. BAC DNA was isolated from identified BAC clones and subjected to SNaPshot fingerprinting to construct contigs from BACs containing sequences homologous to the probe. Selected BAC clones which were positive by PCR using selected marker primers (TG551 and TG35) were also included in the SNaPshot analysis.

f. Results

BAC Library Construction and Characterization

With the goal of isolating potato late blight R genes, we constructed two BAC libraries from two plants, K39 and K182 (FIG. 1). Results of outcrosses with a susceptible *S. okadae* genotype indicate that K39 is transheterozygous for Rpi-oka1 and Rpi-oka2. Analysis of the phenotype and genotypes of plants from the K182 pedigree indicate that K182 is heterozygous for Rpi-mcq1

Two BAC libraries were constructed from the HindIII, partially digested potato DNA. The libraries from K39 and K182 consisted of 105,216 and 100,992 clones stored in 274×384- and 263×384-well microtiter plates, respectively.

Figure 2:
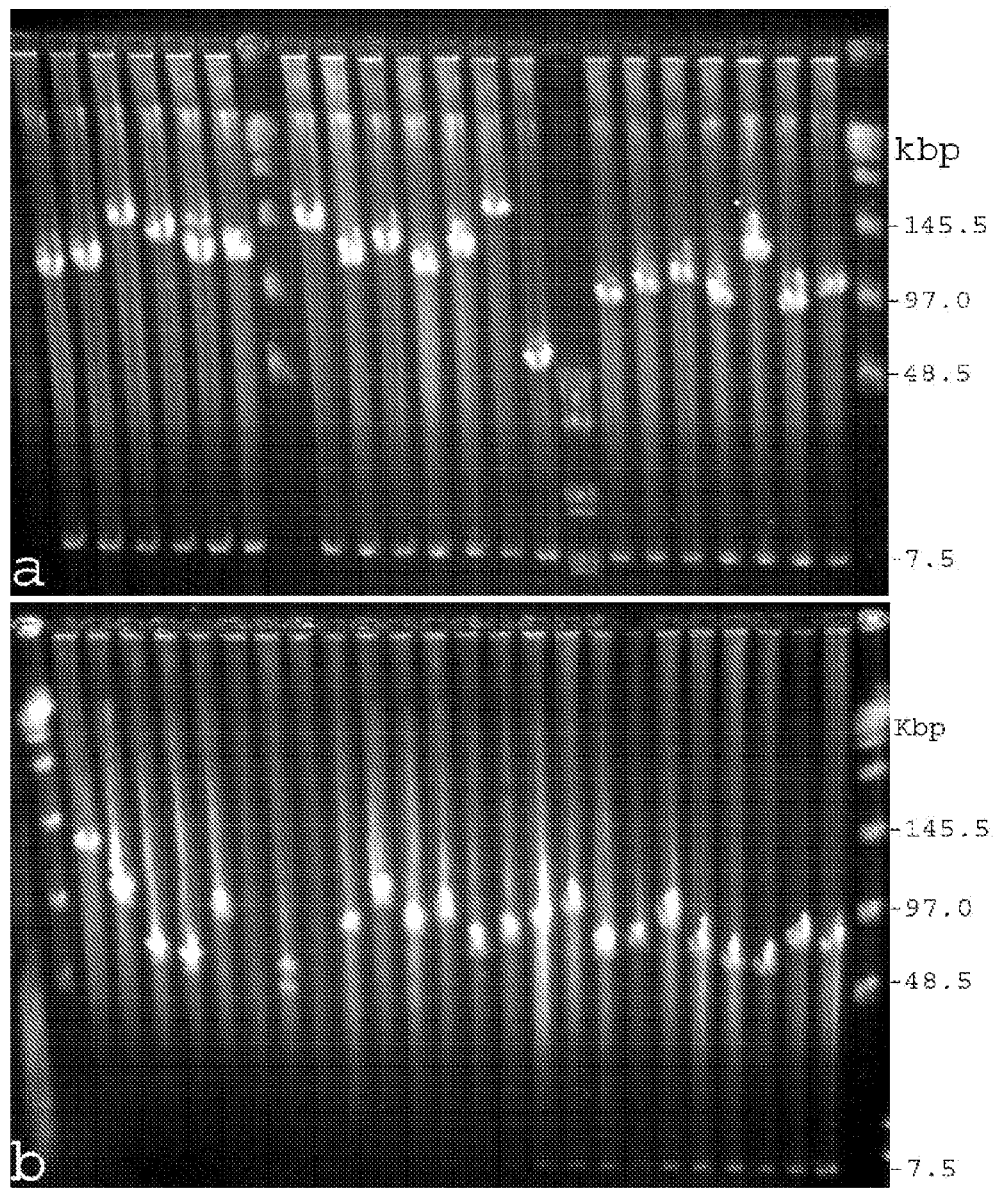
FIG. 2 Analysis of insert size of randomly selected BAC clones from two BAC libraries, K39 (a) and K182 (b) by pulsed-field gel electrophoresis. The BAC clones were digested with NotI. The bands at 7.5 Kb are derived from the cloning vector pindigoBAC-5. Molecular weight size markers given by the lambda ladder (Sigma Chemical) are indicated on the right of the pictures FIG. 3 Map positions of the late blight resistance genes Rpi-oka1, Rpi-oka2 and Rpi-oka3 from *S. okadae* and Rpi-nrs1 from *S. neorossii*.

Average insert sizes were estimated based on pulsed-field gel analysis of NotI digested DNA from 38 and 40 randomly selected clones from the K39 and K182 libraries, respectively. The patterns of NotI digested clones from the two libraries are shown in FIG. 2. The estimated insert sizes ranged from 60 to 165 Kb with an average of 103.5 Kb for the K39 library and from 50 to 130 Kb with an average of 85.5 Kb for the K182 library. The haploid genome size of potato is estimated to be about 1,000 Mb, therefore the genome equivalents are predicted to be 10.9× and 8.6× for the K39 and K182 libraries, respectively.

Example 2

Identification, Mapping and Cloning of Rpi Genes from *Solanum okadae* and *S. neorossii* a. Plant Growth Conditions

Seed of 12 Solarium okadae and 4 *S. neorossii* accessions (Table 1b) was obtained from the Centre for Genetics Resources in Wageningen, the Netherlands (CGN). Seed was surface sterilised in 70% ethanol for 1 minute, disinfected with 1.5% hypochlorite for 5 minutes, rinsed 3 times in sterile distilled water and placed on solid MS (murashige and Skoog) medium (2% agarose) containing 3% sucrose for germination. Germinated seedlings were transferred to glasshouse facilities and treated regularly with fungicides and pesticides to control thrips, aphids, spider mites, powdery mildew and early blight (*Alternaria solani*).

b. *Phytophthora infestans* Strains, Inoculation and Pathotest Scoring

*P. infestans* isolate 98.170.3 (race 1.3.4.10.11; Smilde et al. 2005) was provided by Dr David Shaw at Bangor University, UK. Isolates 90128 (race 1.3.4.7.8.9.10.11), IPO-complex (race 1.2.3.4.6.7.10.11), IPO-0 (virulence spectrum unknown) and EC1 (race 3.4.7.11) were provided by Dr Edwin van der Vossen at Plant Research International, Wageningen, The Netherlands. The 'SuperBlight' isolate was provided by Dr Paul Birch, SCRI, Dundee, UK and is an isolate currently virulent on a large number of commercially grown potato cultivars in the UK and Europe. Isolates MP324, MP717, MP778, MP674, MP622, MP618 and MP650 were obtained from IHAR, Poland.

The isolates were maintained at 18° C. on Rye B agar. Fresh sporangia were produced in a two-weekly cycle by sub-culturing to fresh plates. Periodically, the ability of isolates to infect host material was confirmed on detached leaves of a suitable, sensitive plant. Mature, fresh sporangia were harvested after 10 days growth on Rye B medium by flooding the plate with sterile deionised water and allowing the harvested spore suspension to stand for 20 minutes in a fresh Petri dish. After this time most sporangia are stuck to the plastic surfaces of the dish. Water from the original suspension was replaced by fresh cold water, the sporangia resuspended and incubated at 4° C. for 1 to 4 hours to induce zoospore release.

A detached leaf assay was used to screen for resistance to *P. infestans* (modified from (Vleeshouwers et al. 1999)). Two leaves per plant were detached, inserted in a small portion of wet florist sponge and placed in a 9 cm Petri dish. Leaves were inoculated with 10 µl droplets of a zoospore suspension (20,000 to 50,000 zoospores ml$^{-1}$) and the inoculum gently spread over the abaxial leaf surface with an artist's brush. Petri dishes were wrapped in plastic film and incubated for 7 to 12 days under controlled environmental conditions (18° C.; 18 h light/6 h dark cycle) before scoring phenotypes. Plants with leaves showing sporulating lesions were scored as susceptible; plants with leaves showing no visible symptoms or necrosis in the absence of sporulation were scored as resistant. When the two leaves did not show the same reaction, the plant phenotype was considered intermediate (weak resistance). To confirm these intermediate phenotypes, at least three independent inoculations were carried out. For clear cut phenotypes (either both leaves resistant or both sensitive), two independent rounds of inoculations were considered sufficient.

c. DNA Isolation

DNA was isolated from plant material using either the DNeasy 96 Plant kit (Qiagen) or the protocol of (Park et al. 2005). Briefly approximately 50 mg of leaf material was harvested into 250 µl of nuclear lysis buffer (200 mM Tris-HCl pH 7.5, 50 mM EDTA, 2 M NaCl, 2% CTAB) to which 200 µl of DNA extraction buffer (100 mM Tris-HCl pH 7.5, 350 mM sorbitol, 20 mM sodium bisulfite) was added. The leaf material was then disrupted using a Retsch MM300 milling machine with two 3 mm steel ball bearings for each sample and incubated at 65° C. for 1 hour. Two hundred and fifty microliters of ice cold chloroform was added, the samples mixed and centrifuged at 3500 rpm for 10 minutes. The supernatant was transferred to a fresh tube and the DNA precipitated by the addition of an equal volume of isopropanol followed by centrifugation at 3500 rpm for 60 min. Precipitated DNA was air dried and resuspended in 100 µl TE.

d. AFLP and SSR Analysis and PCR-Based Mapping

AFLP was performed essentially as described in (Thomas et al. 1995) and (Vos et al. 1995) on PstI/MseI-digested template DNA using a pre-amplification step with PstI+0 and MseI+1 primers and a selective amplification step using PstI+2 and MseI+3 primers. AFLP reaction products were denatured and separated by electrophoresis on a 4.5% acrylamide/7.5 M urea/0.5×TBE (45 mM Tris-borate, 1 mM EDTA) gel run at 100 W for 2.5 h. After electrophoresis, gels were transferred to Whatman 3 mM paper, dried without fixing and exposed to X-ray film (X-OMAT AR, Kodak) for 1-7 days.

Informative AFLP bands were cut from the gel and rehydrated in TE (10 mM Tris-HCl pH 8.0, 0.1 mM EDTA). The gel slices were then transferred to fresh TE, crushed and the debris removed by centrifugation at 14000 g for 1 min. For cloning, AFLP fragments were first re-amplified by PCR using 2 µl of the supernatant and the same cycling conditions and primers as for the original amplification. Resulting products were cloned into pGEM-T Easy (Promega, Madison, Wis.) following the manufacturer's instructions and sequenced using the ABI PRISM Big Dye (v. 3.1) Terminator Cycle Sequencing Ready Reaction kit (PE Applied Biosystems) according to the manufacturer's instructions.

SSR PCR reactions were done in 25 µl reaction volumes containing 20 mM Tris-HCl (pH 8.4), 50 mM KCl, 2.5 mM MgCl$_2$, 0.4 mM each of dCTP, dTTP and dGTP, 0.012 mM non-labelled dATP, 370 kbq [γ$^{33}$P)]NATP (Amersham Biosciences,), 0.4 µM of each primer, 1 U Taq DNA polymerase (Invitrogen, Carlsbad, Calif.) and 100 ng template DNA. Thermal cycling conditions consisted of an initial denaturation step at 94° C. for 4 min, followed by a primer annealing step (either 50° C. or 55° C. depending upon the primer pair used; see Table 2) for 2 min and an extension step at 72° C. for 90s. Subsequent cycles were as follows: 29 cycles of 94° C. for 1 min, primer annealing temperature for 2 min, 72° C. for 90 s, followed by a final extension step of 72° C. for 5 min. Amplification products were denatured by the addition of an equal amount of stop solution (95% formamide containing bromophenol blue and xylene cyanol) and heated to 98° C. for 10 min. Two to five microliters of the reaction were run on 6% denaturing polyacrylamide gels containing 6 M urea at 100 W for 2-4 hours. Gels were dried and exposed to X-ray film as for AFLP reactions.

Conventional PCRs were done in 15 µl reaction volumes containing 20 mM Tris-HCl (pH 8.4), 50 mM KCl, 1.5 mM MgCl$_2$, 200 µM each dNTP, 0.4 µM of each primer, 0.5 U Taq polymerase (Invitrogen) and 10-100 ng template DNA. Thermal cycling conditions typically consisted of an initial denaturation step of 94° C. for 2 min followed by 35 cycles of 94° C. for 15 s, primer annealing temperature (Table 2) for 30 s, 72° C. for 1 min per kb of amplified product followed by a final extension step of 72° C. for 10 min. For sequencing, primers and dNTPs were removed from PCR products by incubation with 1.2 U Exonuclease I and ×1.2 U SAP at 37° C. for 30 min followed by incubation at 80° C. for 20 min to denature the enzymes. Sequencing was done using the ABI PRISM Big Dye (v. 3.1) Terminator Cycle Sequencing Ready Reaction kit (PE Applied Biosystems) according to the manufacturer's instructions. Sequences were examined for single nucleotide polymorphisms (SNPs) between resistant and sensitive haplotypes that could be used to develop CAPS (cleaved amplified polymorphic sequences) markers for mapping in segregating populations.

e. Results

Variation for Resistance to *P. infestans* in CGN Accessions

Screening of 12 *S. okadae* accessions using *P. infestans* isolate 98.170.3 in detached leaf assays showed phenotypic variation for resistance in six of them (Table 1b). The remaining six accessions were all sensitive to this particular isolate, despite CGN data indicating that at least three of these accessions were moderately or very resistant to *P. infestans*. Resistance was evident as a complete lack of sporulation on leaf tissue whereas extensive mycelial growth was evident on leaves of sensitive individuals from 4 days post inoculation (FIG. 1.). Sensitive leaves often turned completely black by seven days post inoculation.

Development of *S. okadae* and *S. neorossii* Mapping Populations

Resistant individuals from five of the *S. okadae* accessions were crossed with sensitive individuals from either the same or different accessions (Table 3). In each of the crosses, resistance to *P. infestans* segregated 1:1 in the resulting progeny indicating the presence of potentially five heterozygous Rpi genes in the resistant parents. An interspecific cross between a susceptible *S. okadae* plant and a resistant *S. neorossii* plant was made. Analysis of resistance in the resulting progeny indicated the presence of a dominant Rpi gene that segregated in a 1:1 ratio.

Mapping Rpi Genes in *S. okadae*

Rpi-oka1

A total of 72 AFLP primer combinations were used to screen the Soka014 resistant and sensitive pools to obtain fragments linked to Rpi-oka1. Primer combination PstI+CT/MseI+AGA produced a 97 by fragment that was amplified only from the resistant parent and resistant pools of the Soka014 population. The sequence of this fragment was similar to the expressed sequence tag (EST) SGN-U214221 from the *Lycopersicon* combined EST library (http://www.sgn-.cornell.edu). PCR primers were designed from the sequence of SGN-U214221 and used to amplify a band of approximately 2 kb from *Solanum lycopersicum* (formerly *Lycopersicon esculentum*, Le) and *S. pennellii* (formerly *L. pennellii*, Lp) which showed polymorphism between the two species when digested with AluI. Analysis of the polymorphism in Le/Lp introgression lines (Eshed and Zamir 1994) located this marker in IL 9.2, indicating that the marker could be in either arm of chromosome IX. The polymorphism was not in IL 9.1, which overlaps IL 9.2 substantially, suggesting that the marker is situated proximal to the centromere on either chromosome arm.

Using different PCR primers (SokaM2.9LF5 and SokaM2.9LR5) and Ddel digestion, this marker (SokaM2.9L) was mapped in the Soka014 population, giving a distance of approximately 6 cM (3 recombinants out of 48 segregants) from Rpi-oka1 (FIG. 3).

Additional markers were developed by designing PCR primers from known chromosome IX RFLP marker sequences within the SGN database, sequencing the PCR products amplified from both resistant and sensitive parental DNA and identifying SNPs that could be used to develop CAPS markers (Table 2). In this way, Rpi-oka1 was mapped to a 6.0 cM region of chromosome IX, delimited by markers C2_At4g02680 and TG186. The markers TG551 and TG35 were found to co-segregate with Rpi-oka1 (FIG. 3).

Rpi-oka3

The resistant and sensitive pools of the Soka040 population were screened with a total of 48 AFLP primer combinations. Primer combination PstI+AT/MseI+GCT produced a linked fragment of 108 bp. No significant sequence similarities were found for this fragment and although it was possible to amplify a fragment from Le and Lp using PCR primers designed from the sequence, no polymorphisms were found that could be used to map the marker in the introgression lines. However, a Ddel polymorphism was present between the parents of the Soka040 population, which enabled the converted PCR marker (M6.44) to be mapped approximately 23 cM from Rpi-oka3 (FIG. 3).

AFLP primer combination PstI+AA/MseI+GTC produced a linked fragment of approximately 260 bp. Primers designed from this sequence amplified a fragment from Le and Lp that gave a polymorphism when digested with either Haelll or Sau3Al. This polymorphism was present in introgression line IL 9-2. No polymorphisms were found between the parents of the Soka040 population and so the marker could not be mapped in relation to Rpi-oka3.

To confirm the placing of Rpi-oka3 on chromosome IX, four SSR markers (Stm0010, Stm 0017, Stm 1051 and Stm 3012; (Milbourne et al. 1998)) were investigated for linkage to Rpi-oka3. Stm0017 did not amplify successfully from the sensitive parent and thus could not be used for mapping. Stm0010, Stm1051 and Stm3012 which all map to the short arm of chromosome IX (Milbourne et al. 1998) all showed polymorphism between resistant and sensitive parents and pools and thus provided further evidence that the gene was on chromosome IX (FIG. 3).

Rpi-oka2

A total of 72 AFLP primer combinations were used to screen the Soka013 resistant and sensitive pools to obtain fragments linked to Rpi-oka1. AFLP primer combination PstI+AA/MseI+CAT produced a linked fragment which was converted into PCR based allele specific marker of approximately 200 by (Soka13M5.17). This marker mapped a distance of about 6.5 cM from Rpi-oka2 (FIG. 3).

Additionally, 3 further AFLP markers (P12M44_103, P13M42_228 and P17M33_472) were placed on the Rpi-oka2 linkage map (FIG. 3).

As Rpi-oka1 and Rpi-oka3 were shown to be closely linked to the chromosome IX markers TG551 and TG35, these markers were also investigated for linkage to Rpi-oka1. In the Soka013 population, TG551 and TG35 mapped 0.7 cM centromeric of Rpi-oka2 on chromosome IX (FIG. 3), flanked by marker T1421.

Mapping Rpi genes in S. neorossii
Rpi-nrs1

Figure 3:
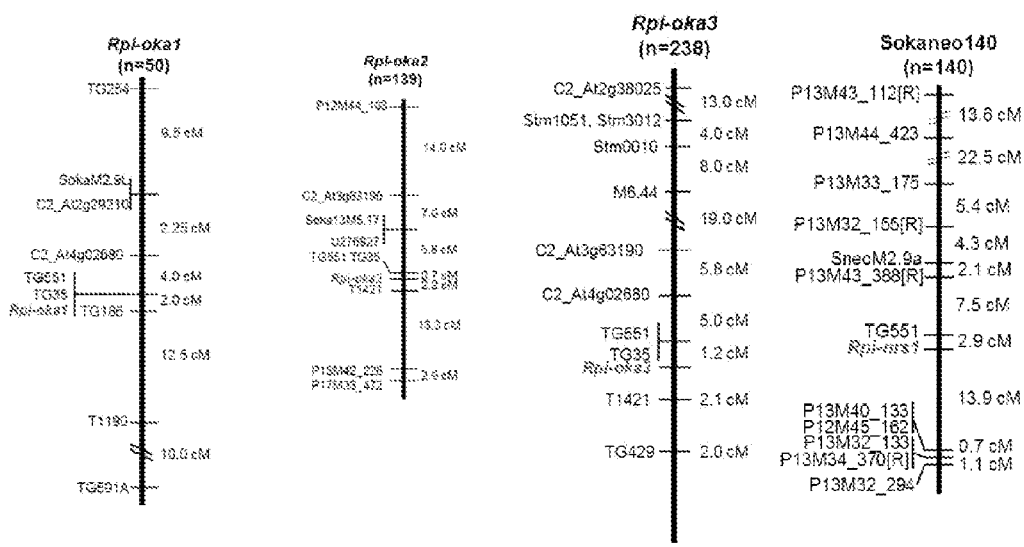

A total of 11 AFLP markers were placed on the Rpi-nrs1 linkage map (FIG. 3). Attempts were made to convert these markers into SCAR markers to investigate polymorphisms that could be used to place these markers on the Le/Lp introgression lines (Eshed and Zamir 1994). However, none of these markers were informative and thus a chromosomal location for Rpi-nrs1 could not be confirmed using these markers. Marker TG551 did show tight linkage to Rpi-nrs1 and thus we concluded that Rpi-nrs1 is also situated on chromosome IX, probably at the same locus as Rpi-oka1-3.

Use of an NBS Marker Closely Linked to Rpi-oka1, 2, 3 and Rpi-nrs1 for Mapping

The NBS marker NBS3B (see Example 3) was converted to a PCR-based SCAR marker which could be amplified using the primers okaNBSHae-F and okaNBSHae-R (Table 2). These primers amplified a 555 by fragment (marker okaNBSHae) from resistant plants containing Rpi-oka1, Rpi-oka2 and Rpi-nrs1. In each population, this marker was shown to co-segregate with the resistance gene (FIG. 3). For Rpi-oka3, a PCR product was amplified from both resistant and susceptible plants. However, the marker was converted into a CAPS marker by digestion with MaeIII. This CAPS marker was shown to co-segregate with Rpi-oka3 in the Soka040 population (FIG. 3).

BAC Library Screening and Contig Construction

We used nine PCR markers linked to Rpi-oka1, Rpi-oka2 and Rpi-mcq1 for screening the BAC libraries. As shown in Table 1a, TG551, TG35 and TG186 are linked to Rpi-oka1. TG551 is also linked to Rpi-oka2. The marker okaNBSHae is linked to both Rpi-oka1 and Rpi-oka2. Although TG551 is linked to both genes from S. okadae, the alleles of this marker from the Rpi-oka1 and Rpi-oka2 haplotypes can be distinguished by restriction digestion as indicated in Table 1a. U282757, U296361, TG591 and U279465 are all linked to Rpi-mcq1. The number of BAC pools shown to be positive for these markers varied from 11 to 17 for the K39 library and from 9 to 14 for the K182 library (Table 1a).

Figure 4:
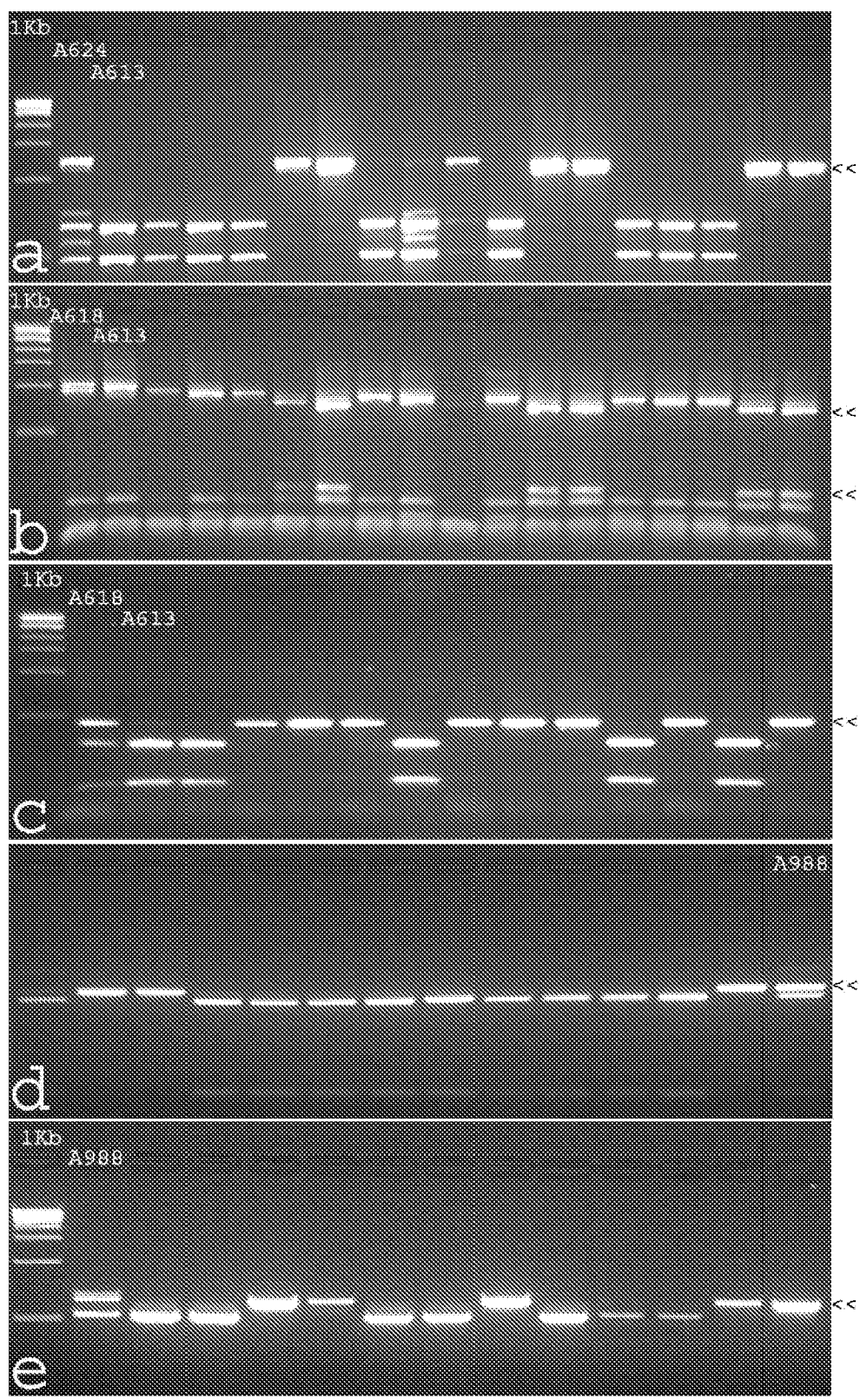
FIG. 4 Pictures of SCAR markers used to screen two BAC libraries. TG551 digested with TaqI (a) is linked to Rpi-oka1, TG551 digested with MwoI (b) and TG35 (c) are linked to Rpi-oka1, and U296361 (d) and TG591 (e) are linked to Rpi-mcq1. The 1 Kb size ladder and parental genotypes (A624, A613, A618 and A988) are indicated and the rests are BAC pools positive to certain markers identified by PCR followed by digestion with restriction enzyme. The resistant allele is indicated by '<<' on the right of each picture.

In the K39 library, the TG186 marker was amplified from 17 pools. It was not possible to determine from which haplotype (Rpi-oka1 or Rpi-oka2) this marker was amplified. TG186, despite being a CAPS marker, is linked to Rpi-oka1 in repulsion, and the allele present in the Rpi-oka1 haplotype is indistinguishable from that in the Rpi-oka2 haplotype. The marker okaNBSHae was amplified from 18 pools. As this marker is not polymorphic between the Rpi-oka1 and Rpi-oka2 haplotypes, it was not possible to assign haplotype to these BACs based on this marker. TG551 was amplified by PCR from 16 pools and restriction enzyme digestion showed there to be six pools positive for the Rpi-oka1 haplotype and seven for the Rpi-oka2 haplotype. TG35 was amplified by PCR from 11 pools, eight of which were shown to be from the Rpi-oka1 haplotype by restriction digestion, suggesting that the remaining three were from the Rpi-oka2 haplotype. Gel images showing the PCR-based markers and their restriction patterns (where relevant) are shown in FIG. 4a-4c.

Figure 5:
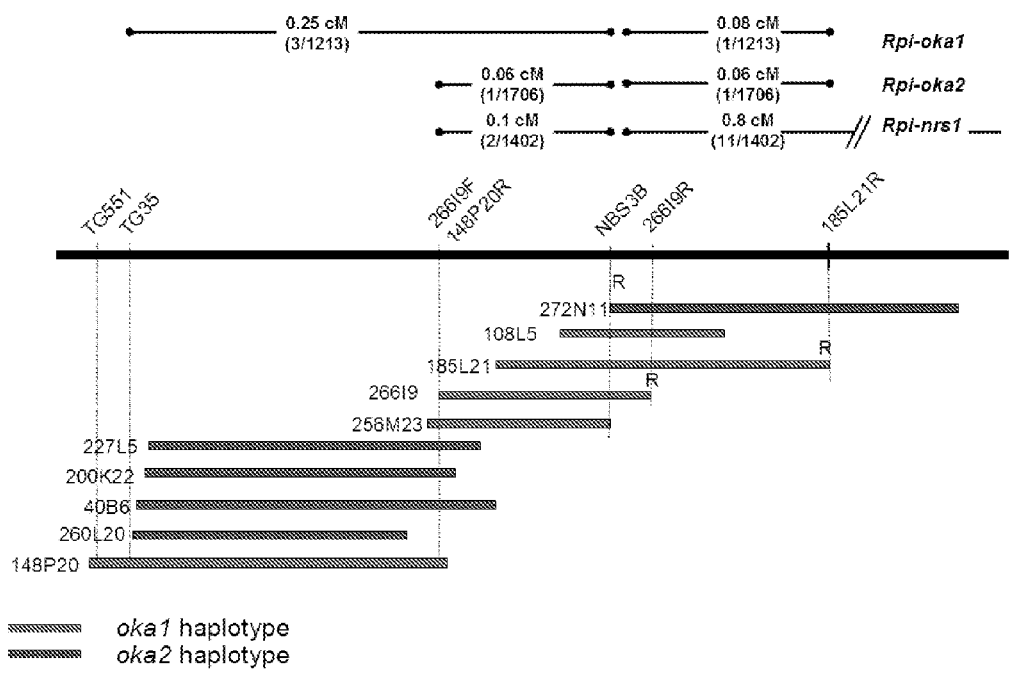
FIG. 5 Contig of BAC clones identified from the K39 BAC library and covering the genomic region containing Rpi-oka1 and Rpi-oka2.

From hybridisation of the okaNBSHae probe to the pooled BAC DNA, a total of 67 pools were identified as containing BAC clones with homologus sequences. From screening high density double-spotted membranes containing each individual BAC clone from the pools identified, a total of 85 BAC clones were identified, DNA isolated and subjected to BAC SNaPshot fingerprinting, along with an additional 10 selected clones which were positive for the TG551 and/or TG35 markers. From the contigs generated, one contig contained BAC clones identified by a) PCR based screening using the linked markers TG551, TG35 and the co-segregating marker okaNBSHae and b) by hybridisation using the okaNBSHae marker as a probe. This BAC contig is shown in FIG. 5.

TABLE 1a

Screening of BAC pools with PCR-based markers linked to late blight resistance loci

| Marker | Linked gene | Hits by PCR[a] | RE[b] | Hits after Digestion[c] |
|---|---|---|---|---|
| TG551 | Rpi-oka2 | 16 | TaqI | 7 |
| TG551 | Rpi-oka1 | 16 | MwoI | 6 |
| okaNBSHae | Rpi-oka1 & Rpi-oka2 | 18 | n.a.[d] | n.a. |
| TG186 | Rpi-oka1 | 17 | n.a.[d] | n.a. |
| TG35 | Rpi-oka1 | 11 | HhaI | 8 |
| U282757 | Rpi-mcq1 | 14 | XhoI | 6 |
| U296361 | Rpi-mcq1 | 13 | HincII | 3 |
| TG591 | Rpi-mcq1 | 14 | HaeIII | 7 |
| U279465 | Rpi-mcq1 | 9 | n.a. | n.a. |

[a]The number of positive pools to the marker by PCR
[b]Restriction enzyme causing polymorphic between resistant and susceptible alleles
[c]The number of pools positive to the marker after digestion with a certain enzyme
[d]not applicable because the marker is linked in repulsion or not polymorphic between resistant and susceptible alleles Pools from the K39 library which were positive to either TG551, TG35 or okaNBSHae, markers which are closely linked to or, in the case of okaNBSHae, co-segregate with Rpi-oka1 or Rpi-oka2, were randomly chosen. The original 384-well plates for each of the BAC libraries were replicated onto solid LB medium. Colonies from each plate were scraped by rows and columns and screened for the presence of the relevant marker. Single clones from 384-well plates were selected.

Following selection of single clones, BAC DNA was isolated and BAC-ends were sequenced. BLAST homology searches (http://www.ncbi.nlm.nih.gov/BLAST/) showed that two of the clones from the K39 library (K39__272N11 and K39__256M23) had BAC-end sequences which were highly similar to each other and to the tomato mosaic virus R gene Tm-2[2] (Lanfermeijer et al. 2003).

Figure 6:
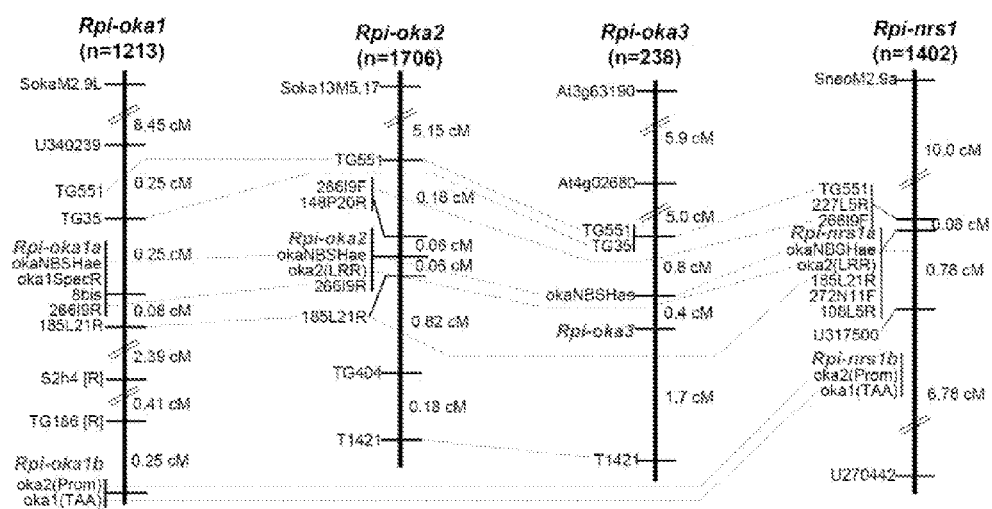
FIG. 6 High resolution and fine scale mapping of Rpi genes derived from *Solanum okadae* and *S. neorossii*.

PCR Primers were designed from each of the BAC end sequences obtained and used to amplify products from the parental genotypes of Rpi-oka1 and Rpi-oka2. PCR products were sequenced and analysed for the presence of SNPs that allowed use of the PCR products as markers in the respective populations. Successfully converted markers were placed on a higher resolution genetic map for Rpi-oka1 (1213 individuals) and Rpi-oka2 (1706 individuals). The position of these markers in relation to Rpi-oka1 and Rpi-oka2 is shown in FIG. 6.

High Resolution Mapping and Cloning of Rpi-oka1

The Rpi-oka1 population Soka014 consisting of 1214 individuals was screened for recombinants between the markers SokaM2.9L and TG186. A total of 169 recombinants were identified, covering a genetic interval of 14 cM. Initial screening of these recombinants for disease phenotype indicated that the resistance locus was located south of marker TG35. Hence, a subset of 53 recombinants between the markers TG35 and TG186 were selected from the larger subset of recombinants. These recombinants were screened for resistance or susceptibility to P. infestans and with markers developed from the BAC end sequences. The results indicated that Rpi-oka1 was located within a genetic interval of 0.33 cM delimited by the markers TG35 and 185L21R (BAC end marker) (FIG. 5, 6). By reference to the physical map constructed from PCR and fingerprinting analysis of BAC clones from the K39 library (FIG. 5) Rpi-oka1 was predicted to be present on a physical region covered by the two BAC clones K39_148P20 and K39_26619. These two BAC clones were sequenced and one candidate ORF was identified for Rpi-oka1.

High Resolution Mapping and Cloning of Rpi-oka2

To construct a high resolution map, we used two flanking PCR based markers (TG551 and T1421; FIG. 1a) to screen an expanded population for selecting recombinants around the resistance locus. 46 recombinants from the expanded population of 1706 genotypes were selected representing an interval of 2.9 cM between the two PCR markers. These recombinants were phenotyped for late blight resistance and genotyped using the BAC end markers from the BAC contig. The results indicated that Rpi-oka2 was located within a genetic interval of 0.12 cM delimited by the BAC-end markers 26619F and 185L21R (FIG. 5, 6). By reference to the physical map constructed from PCR and fingerprinting analysis of BAC clones from the K39 library Rpi-oka2 was therefore predicted to be present on the same physical region as that identified for Rpi-oka1. However, other than the BAC clone K39_272N11 (for which one end contained a partial Tm2$^2$ homologue) clones which covered the same physical region as Rpi-oka1 could not be identified within the library (FIG. 5). As an alternative approach, primers were designed to amplify the complete Rpi-oka1 ORF were used in a PCR reaction with DNA from the parent plant of the Rpi-oka2 population. The resulting PCR product was cloned into pGEM-T Easy and 4 clones were sequenced to obtain a consenus sequence for the Rpi-oka2 candidate.

High Resolution Mapping of Rpi-nrs1

To construct a high resolution map, we used three flanking PCR based markers (SneoM2.9a, TG551 and TP25; FIG. 3) to screen an expanded population and select recombinants around the Rpi-nrs1 resistance locus. TP25 was converted from an AFLP marker, P13M34_370[R]. Initially 323 recombinants from the expanded population of 1402 genotypes were selected resulting in an interval of 23 cM genetic distance between SneoM2.9a and TP25. At the same time, closer PCR markers to Rpi-nrs1 were developed (U317500 and U270442). Consequently 40 recombinants were selected and these recombinants were phenotyped for late blight resistance. The RGA marker designated okaNBSHae mapped to the same genetic location as that of Rpi-nrs1 and several BAC-end sequence based PCR markers were developed from the Rpi-oka1/2 contig from the K39 BAC library allowing construction of a fine scale genetic map around Rpi-nrs1 (FIG. 6). Additionally the recombinants were tested for resistance using three different isolates and the phenotypes were differently segregated indicating that there are multiple genes in the population. The second gene designated Rpi-nrs1b is expected to be located to the south of Rpi-nrs1a (FIG. 6).

Analysis of Rpi-oka1, Rpi-oka2 and Rpi-oka3

The Rpi-oka1 ORF is 2673 by long and translates into a protein sequence of 891 amino acids with a calculated molecular weight of 102 kDa and a pI of 8.05. The Rpi-oka2 ORF comprises 2715 by and translates into a protein sequence of 905 amino acids with a calculated molecular weight of 103.6 kDa and a pI of 8.16. The sequence of the PCR product amplified from material containing Rpi-oka3 was identical to that of Rpi-oka2. The Rpi-oka1 protein contained all the features characteristic of the coiled coil-nucleotide binding region-leucine rich repeat (CC-NB-LRR)-class of resistance proteins. Within the first 215 amino acids of the N-terminal part of the protein were 4 regions each with 3 predicted heptad repeat motifs typical of coiled coil domains (FIG. 7). All NB-ARC domains (van der Biezen and Jones 1998) were present in the amino acid sequence from 216-505. Following the NB-ARC domain was a region comprising of a series of 15 irregular LRR motifs that could be aligned according to the consensus sequence LxxLxxLxxLxLxxC/N/Sx(x)LxxLPxx (where L can be L, I, M, V, Y or F and x is any amino acid) (McHale et al. 2006).

The sequence of Rpi-oka2 differs from Rpi-oka1 by an insertion of 42 nucleotides in the 5' end of the gene (FIG. 7). The resulting additional 14 amino acids present in the corresponding region of Rpi-oka2 do not affect any of the predicted coiled coil domains. There are also 3 single nucleotide polymorphisms (SNPs) between Rpi-oka1 and Rpi-oka2; A1501T, T1767C and G2117A (FIG. 7). These nucleotide differences result in two amino acid differences between Rpi-oka1 and Rpi-oka2 (FIG. 7). The difference at position 501 is at the end of the NB-ARC domain, just prior to the LRR region and results in the change of an asparagine in Rpi-oka1 to a tyrosine in Rpi-oka2. This amino acid change does not affect any of the characterised NB-ARC domains. At position 706, within the 9$^{th}$ LRR, an arginine in Rpi-oka1 becomes a lysine in Rpi-oka2; both of these residues are positively charged polar amino acids and hence this can be considered a synonymous change.

Rpi-oka1 and Rpi-oka2 share 80.9% and 79.7%, identity, respectively, with Tm-2$^2$ at the nucleic acid level. At the amino acid level, this translates to 72.1% and 71.1% identity, respectively, at the amino acid level. As expected, given its role in recognition specificity, the percentage of similarity was lowest in the LRR domain where Rpi-oka1/2 and Tm-2$^2$ share only 57.5% similarity. In contrast, the sequence similarity across the coiled-coil and NB-ARC domains of Rpi-oka1/2 and Tm-2$^2$ was 81.8% and 79.7%; within the conserved domains of the NB-ARC region, Tm-2$^2$ and Rpi-oka1 differ by only 1 amino acid.

The primers oka1 long-F and oka1long-R (Table 2) were used to amplify Rpi-oka1 homologous sequences from the parental material containing Rpi-oka3. Resulting PCR products were cloned into pGEM-T and sequenced. The sequences obtained were identical to Rpi-oka2.

It was not possible to amplify full-length Rpi-oka1 paralogues from the susceptible S. okadae parent A613. This observation, together with the fact that the okaNBSHae marker could only be amplified from resistant genotypes suggests that the susceptible phenotype is caused by an absence of Rpi-oka1 rather than a non-functional copy.

Rpi-oka1 is also Present in Resistant S. neorossii Genotypes and is the Orthologue of Rpi-phu1.

Mapping of an Rpi gene in a segregating population derived from a resistant individual of S. neorossii accession CGN1800 also showed close linkage between the identified gene (Rpi-nrs1) and marker TG551, indicating that this gene was located in the same region as Rpi-oka1. Similarly, Rpi-phu1 from S. phureja was also reported to map to this region (Sliwka et al. 2006). The Rpi-oka1 marker okaNBSHae-F/R co-segregated with resistance in a population of 149 S. tuberosum plants segregating for Rpi-phu1. Full-length Rpi-oka1 paralogues were amplified from DNA of 3 resistant genotypes containing Rpi-phu1. A single product was obtained and sequencing showed this to be identical to Rpi-oka1. Similarly, amplification from resistant S. neorossii material showed that Rpi-oka2 was present in this material and the presence of this gene correlated with resistance in 40 pre-selected recombinants. Resistant plant material containing Rpi-nrs1 or Rpi-phu1 was also shown to be resistant to each of the P. infestans isolates used in this study, with the exception of EC1. Thus we conclude that Rpi-oka1=Rpi-phu1 and Rpi-oka2=Rpi-oka3=Rpi-nrs1.

TABLE 1b

Reaction to *Phytophthora infestans* of twelve
*Solanum okadae* and four *S. neorossii* accessions

| Accession[a] | Wild species | Reference data Phenotype | Source | Fine screening[b] R | MR | MS | S |
|---|---|---|---|---|---|---|---|
| CGN17998 | S. okadae | Very resistant | CGN | 2 | | | 7 |
| CGN17999 | S. okadae | Resistant | CGN | 3 | | | 7 |
| CGN18108 | S. okadae | Very resistant | CGN | 8 | | 3 | |
| CGN18109 | S. okadae | Very resistant | CGN | | | | 10 |
| CGN18129 | S. okadae | Susceptible | CGN | | 2 | 2 | 6 |
| CGN18157 | S. okadae | Moderately resistant | CGN | | | | 10 |
| CGN18269 | S. okadae | Susceptible | CGN | | | | 10 |
| CGN18279 | S. okadae | Very resistant | CGN | 4 | | | 5 |
| CGN20599 | S. okadae | Susceptible | CGN | | | | 10 |
| CGN22703 | S. okadae | Very susceptible | CGN | 4 | 1 | | 4 |
| CGN22709 | S. okadae | Very susceptible | CGN | | | | 8 |
| BGRC27158 | S. okadae | Moderately resistant | CGN | | | | 1 |
| CGN17599 | S. neorossii | Susceptible | CGN | | | | 10 |
| CGN18000 | S. neorossii | Very resistant | CGN | 11 | | | |
| CGN18051 | S. neorossii | Susceptible | CGN | | | | 6 |
| CGN18280 | S. neorossii | Very susceptible | CGN | | | | 10 |

[a]CGN, Centre for Genetic Resources in the Netherlands (http://www.cgn.wageningen-ur.nl); BGRC, Braunschweig Genetic Resources Center.
[b]Number of plants showing resistant (R) or susceptible (S) phenotypes

TABLE 2

PCR based markers used for mapping of Rpi-oka1, Rpi-oka2, Rpi-oka3 and Rpi-nrs1

| Marker | Primer sequence (5'-3') | SEQ ID NO: | Tm (° C.) | Type of marker[a] Rpi-oka1 | Rpi-oka2 | Rpi-oka3 | Rpi-nrs1 |
|---|---|---|---|---|---|---|---|
| TG254 | F: AGTGCACCAAGGGTGTGAC | 17 | 60 | | | | |
| | R: AAGTGCATGCCTGTAATGGC | 18 | | | | | |
| At2g38025 | F: ATGGGCGCTGCATGTTTCGTG | 19 | 55 | | | Tsp509I [R] | |
| | R: ACACCTTTGTTGAAAGCCATCCC | 20 | | | | | |
| Stm1051 | F: TCCCCTTGGCATTTTCTTCTCC | 21 | 55 | | | SSR | |
| | R: TTTAGGGTGGGGTGAGGTTGG | 22 | | | | | |
| Stm3012 | F: CAACTCAAACCAGAAGGCAAA | 23 | 55 | | | SSR | |
| | R: GAGAAATGGGCACAAAAAACA | 24 | | | | | |
| Stm0010 | F: TCCTTATATGGAGCAAGCA | 25 | 50 | | | SSR [R] | |
| | R: CCAGTAGATAAGTCATCCCA | 26 | | | | | |
| M6.44 | F: ATTGAAAGAATACACAAACATC | 27 | 55 | | | DdeI | |
| | R: ATTCATGTTCAGATCGTTTAC | 28 | | | | | |
| At3g63190 | F: TTGGTGCAGCCGTATGACAAATCC | 29 | 55 | | EcoRI | Tsp509I | |
| | R: TCCATCATTATTTGGCGTCATACC | 30 | | | | | |
| SneoM2.9a | F: TAGATCTATACTACACTTGGCAC | 31 | 50 | | | | as |
| | R: TAATCTCTTCCATCTTCCC | 32 | | | | | |
| SokaM2.9L | F: ACAAACCTATGTTAGCCTCCCACAC | 33 | 60 | DdeI | | | |
| | R: GGCATCAAGCCAATGTCGTAAAG | 34 | | | | | |
| At2g29210 | F: AGCAGGACACTCGATTCTCTAATAAGC | 35 | 55 | NcoI | | | |
| | R: TGCACTAAGTAGTAATGCCCAAAGCTC | 36 | | | | | |
| Soka13M5.17 | F: CTGAGGTGCAGCCAATAAC | 37 | 55 | as | | | |
| | R: CCAGTGAGAAACAGCTTCTC | 38 | | | | | |
| U276927 | F: GATGGGCAACGATGTTGTTG | 39 | 60 | Hpy188I | | | |
| | R: GCATTAGTACAGCGTCTTGGC | 40 | | | | | |
| At4g02680 | F: GTGAAGAAGGTCTACAGAAAGCAG | 41 | 55 | MseI | | NheI | |
| | R: GGGCATTAATGTAGCAATCAGC | 42 | | | | | |

TABLE 2-continued

PCR based markers used for mapping of Rpi-oka1,
Rpi-oka2, Rpi-oka3 and Rpi-nrs1

| Marker | Primer sequence (5'-3') | SEQ ID NO: | Tm (° C.) | Type of marker[a] | | | |
|---|---|---|---|---|---|---|---|
| | | | | Rpi-oka1 | Rpi-oka2 | Rpi-oka3 | Rpi-nrs1 |
| TG551 | F: CATATCCTGGAGGTGTTATGAATGC<br>R: CATATCCTGGAGGTGTTATGAATGC | 43<br>44 | 60 | MwoI | TaqI | TaqI | TaqI |
| TG35 | F: CACGGAGACTAAGATTCAGG<br>R: TAAAGGTGATGCTGATGGGG | 45<br>46 | 55 | HhaI | AluI | Tsp509I | |
| T1421 | F: CATCAATTGATGCCTTTGGACC<br>R: CTGCATCAGCTTCTTCCTCTGC | 47<br>48 | 60 | | BslI | RsaI | |
| TG186 | F: AATCGTGCAGTTTCAGCATAAGCG<br>R: TGCTTCCAGTTCCGTGGGATTC | 49<br>50 | 60 | DraI [R] | | | |
| TG429 | F: CATATGGTGACGCCTACAG<br>R: GGAGACATTGTCACAAGG | 51<br>52 | 55 | | | MseI | |
| T1190 | F: GTTCGCGTTCTCGTTACTGG<br>R: GTTGCATGGTTGACATCAGG | 53<br>54 | 55 | as | | | |
| TG591A | F: CTGCAAATCTAGTCGTGCAAG<br>R: CTCGTGGATTGAGAAATCCC | 55<br>56 | 60 | as | | | |
| okaNBSHae | F: CTTACTTTCCCTTCCTCATCCTCAC<br>R: TGAAGTCATCATCCAGACCGATG | 57<br>58 | 60 | as | as | MaeIII | as |
| oka1long | F: AGTTATACACCCTACATTCTACTCG<br>R: CTTTGAAAAGAGGCTTCATACTCCC | 59<br>60 | 60 | as | as | as | as |
| 26619F | F: GTATGTTTGAGTTAGTCTTCC<br>R: TATAATAGGTGTTCTTGGGG | 61<br>62 | 55 | | HinfI | | |
| 26619R | F: AAGGTGTTGGGAGTTTTTAG<br>R: TATCTTCCTCATTTTGGTGC | 63<br>64 | 55 | HindIII | HindIII | | |
| 185L21R | F: GATTGAGACAATGCTAGTCC<br>R: AGAAGCAGTCAATAGTGATTG | 65<br>66 | 55 | BslI | RsaI | | |
| 148P20R | F: AAGATTCTTTTTCCTCCTTAG<br>R: AAAGATGAAGTAGAGTTTTGG | 67<br>68 | 58 | HpyCH4IV | | | |

[a]Restriction enzymes indicate that marker is a CAPS marker, as indicates allele-specific markers, [R] indicates that marker is linked in repulsion phase, SSR indicates that marker is a simple sequence repeat marker, blank indicates that the marker was either not polymorphic or not tested for that Rpi gene.

TABLE 3

Crosses within S. okadae and late blight resistant (R) and sensitive (S) segregants in their progenies

| Population identifier | Population parents[a] | | Segregating progeny[b] | |
|---|---|---|---|---|
| | Female | Male | R | S |
| Soka014 | A618, CGN18108, R | A613, CGN18108, S | 26 | 24 |
| Soka012 | A622, CGN18279, S | A618, CGN18108, R | 18 | 23 |
| Soka013 | A624, CGN18279, R | A613, CGN18108, S | 59 | 80 |
| Soka040 | A606, CGN17998, R | A628, CGN18279, S | 25 | 23 |
| Soka241 | D986, BGRC08237, R | B419, Soka012, S | 24 | 26 |
| Soka184 | D403, CGN17999, R | D401, CGN17999, S | 24 | 21 |
| Sokaneo140 | A613, CGN18108, S | A795, CGN18000, R | 67 | 73 |

[a]Plant identifier number followed by its accession number and reaction to *P. infestans* inoculation: CGN Centre for Genetic Resources in the Netherlands; BGRC, Braunschweig Genetic Resources Center.
[b]Number of plants showing resistant (R) or sensitive (S) phenotypes Example 3

Mapping and cloning Rpi-oka1 and Rpi-nrs1 using a Candidate Gene/Allele Mining Approach To date, cloning of R genes is typically done through a positional cloning strategy. Once a functional gene is cloned from a specific R locus, one can try to clone functional alleles from the same or different species in order to determine allele frequency and allelic variation at a given locus. Here we demonstrate that NBS profiling (Linden et al., 2004) when combined with bulked segregant analysis (BSA) (Michelmore et al., 1991) is a powerful tool to generate candidate gene markers which can predict the position of the R locus under study and in doing so form a starting point for the cloning of the gene through a functional allele mining strategy.

Plant Material

Accessions of *Solanum okadae* and *Solanum* neorossii were requested from the Centre of Genetic Resources (CGN) in Wageningen, The Netherlands. Following screening with *Phytophthora infestans*, resistant genotypes from specific accessions were used to make inter- or intra-specific mapping populations. The Rpi-oka1 mapping population 7698 was made by crossing OKA7014-9 (resistant F1 plant derived from a cross between OKA367-1 and OKA366-8, both derived from accession CGN18108) with the susceptible plant NRS735-2 (CGN18280). All S. okadae genotypes were derived from accession CGN18108. The Rpi-nrs1 mapping population 7663 was generated by crossing the resistant plant NRS365-1 (CGN18000) with NRS735-2.

Disease Assays

Detached leaf assays (DLA) on the Solanum species were carried out as described by Vleeshouwers et al. (1999). Leaves were inoculated with 10 µl droplets of inoculum ($5 \times 10^4$ zoospores/ml) on the abaxial side and incubated at 15° C. for 6 days in a climate chamber with a photoperiod of 16 h/8 h day/night. At 6 days post inoculation, leaves showing sporulation were scored as susceptible whereas leaves showing no symptoms or necrotic lesions were scored as resistant.

Marker Development

Markers from appropriate chromosomal positions were selected from the Solanaceae Genomics Network (SGN) database and subsequently developed into polymorphic markers in each of the relevant mapping populations. Additional candidate gene markers were developed through NBS profiling as described by van der Linden et al. (2004). Templates were generated by restriction digestion of genomic DNA using the restriction enzymes MseI, HaeII, AluI, RsaI or TaqI. Adapters were ligated to restriction fragments. PCR fragments were generated by radioactive-labeled primers (nbs1, nbs2, nbs3, nbs5a6 or nbs9) designed on conserved domains of the NBS domain (P-loop, Kinase-2 and GLPL motifs (Calenge, 2005; Syed, 2006).

PCR Amplification of Candidate R Genes

Long range PCR with Taq-polymerase or Pfu Turbo polymerase 50 µl reaction-mixture was prepared containing 50 ng of gDNA, 1 µl of the forward primer (10 µM), 1 µl of the reverse primer (10 µM), 0.8p(dNTPs (5 mM each), 5 µl×10× buffer, 5 units of Taq-polymerase (Perkin Elmer) or 1 µl of pfu Turbo (Invitrogen). The following PCR program was used: 94° C. for 3 mins, 94° C. for 30 sec, 55° C. for 30 sec, 72° C. for 4 mins, 72° C. for 5 mins during 29 cycles.

Genome Walking

Marker sequences were extended by cloning flanking DNA fragments with the ClonTech Genome Walker kit according to the manufacturer's instructions using a blunt adapter comprising the complementary sequences: 5-GTAATACGACT-CACTATAGGGCACGCGTGGTCGACGGC-CCGGGCTGGA-3 (SEQ ID NO:69) and 5'-PO₄TCCAGCCC SEQ ID NO:70) and the adapter specific primers AP1 (5'-TAATACGACTCACTATAGGGC) and AP2 (5'-ACTATAGGGCACGCGTGGT) SEQ ID NO:71). A simultaneous restriction-ligation was performed followed by two rounds of PCR. A 50 µl restriction-ligation (RL) mixture was prepared containing 250 ng of genomic DNA, 5 units of blunt cutting enzyme (Bsh1236I, AluI, DpnI, HaeIII, RsaI, HincII, DraI, ScaI, HpaI or SspI), 1 µl genome walker adapter (25 µM), 10 mM ATP, 10 µl of 5X RL buffer, 1 unit of T4 DNA ligase (Invitrogen 1U/µl). The digestion mix was incubated at 37° C. for 3 hours. Samples were diluted 50 times prior to PCR. For the first PCR round, a 20 µl reaction-mixture was prepared containing 5 µl of diluted RL DNA, 0.6 µl specific forward primer 1 (10 µM), 0.6 µl AP1 (10 µM), 0.8 µl dNTPs (5 mM each), 2 µl 10X buffer (Perkin Elmer), 5 units Taq-polymerase (Perkin Elmer). The first PCR was performed using the following cycle program: 30-sec at 94° C. as denaturation step, 30-sec at 56° C. as annealing step and 60-sec at 72° C. as extension step. 35 cycles were performed. A second PCR using the same conditions as the first one was performed using specific primer 2 and AP2 and 5 µl of 50 times diluted product from the first PCR. 5 µl of the second PCR product was checked on gel (1% agarose) and the largest amplicons were cloned into the pGEM®-T Easy Vector from Promega and sequenced.

Gateway® Cloning of Candidate R Genes into a Binary Expression Vector

The Gateway® cloning technique was used according to the manufacturer's instructions to efficiently clone candidate genes together with appropriate promoter and terminator sequences into the binary Gateway® vector pKGW-MGW. In plasmid pKGW the gateway cassette was exchanged against a multiple gateway cassette amplified from pDESTr4r3 resulting in pKGW-MGW. In this study we used the promoter and terminator of Rpi-blb3 (Lokossou et al., in preparation) which were cloned into the Gateway® pDONR vectors pDONRP4P1R and pDONRP2RP3, respectively, generating pENTR-B1b3P and pENTR-BIb3T. PCR amplicons generated with Pfu Turbo polymerase were cloned into pDONR221 generating pENTR-RGH clones, and subsequently cloned together with the Rpi-blb3 promoter and terminator fragments into pKGW-MGW using the multiple Gateway® cloning kit (Invitrogen). The pENTR clones were made by carrying out a BP-Reaction II overnight (http.// www.untergassercom/lab/protocols/bp_gateway_reactio-n_ii_v1_0.shtml). DH5α competent cells (Invitrogen) were transformed by heat shock with 5 µl of the BP Reaction II mixture. Cells were selected on LB medium containing 50 mg/ml of Kanamycine. Colonies were checked for the presence of the relevant inserts by colony PCR. DNA of appropriate pENTR clones was extracted from E. coli and used to perform a multiple Gateway® LR cloning reaction to generate the final binary expression clones (http://www.untergas-ser.com/lab/protocols/lr_multiple_gateway_reaction_v1_0.shtml) . . . DH5α competent cells (Invitrogen) were transformed by heat shock with 5 µl of the LR reaction mixture. Cells were selected on LB medium containing 100 mg/ml of spectinomycine. Colonies were checked by PCR for the presence of the correct inserts. Positive colonies were grown overnight in LB medium supplemented with 100 mg/ml of spectinomycine to extract the final expression vector. The final expression vector was transferred to *Agrobacterium tumefaciens* strain COR308 through electropration. Colonies were selected on LB medium supplemented with 100 mg/ml of spectinomycine and 12.5 mg/ml of tetracycline overnight at 30° C.

Sequencing

Cloned fragments or PCR products generated either with Taq-polymerase (Perkin Elmer) or Pfu Turbo polymerase (Invitrogen) were sequenced as follows: 10 µl sequencing reaction mixtures were made using 5 µl of PCR product or 5 ng of plasmid, 3 µl of buffer, 1 µl of DETT (Amersham) and 1 µl of forward or reverse primer. The PCR program used was 25 cycles of 94° C. for 20 sec, 50° C. for 15 sec, 60° C. for 1 min. The sequences were generated on ABI 3730XL sequencers.

Results

Genetic Basis and Spectrum of Late Blight Resistance in Accessions of S. okadae and S. neorossii.

To determine the genetic basis of late blight resistance in S. okadae and S. neorossii, 14 and 5 accessions, respectively, were screened in detached leaf assays (DLA) with the complex *P. infestans* isolate IPO-C. Resistant genotypes selected from the oka accession CGN18108 and the nrs accession CGN18000 were used to generate the S. okadae and S. neorossii mapping populations 7698[oka7014-9 (oka367-1× oka366-8)×nrs735-2) and 7663 (nrs365-1×nrs735-2), respectively. Following DLA's with 50 F1 progeny plants of population 7698, 30 were scored as resistant and 22 as susceptible, suggesting the presence of a single dominant R-gene, which we named Rpi-oka1. Of the 60 F1 progeny plants screened from population 7663, 24 were scored as resistant and 36 as susceptible, suggesting that also nrs365-1 contained a single dominant R gene, which we named Rpi-nrs1.

The resistance spectrum of both genes was analyzed by challenging them with several isolates of different complexity and aggressiveness (Table 4). Rpi-oka1 and Rpi-nrs1 appear to have the same specificity. Strain EC1 was the only one able to overcome both R genes.

Mapping of Rpi-oka1 and Rpi-nrs1 to Chromosome IX

Figure 9:
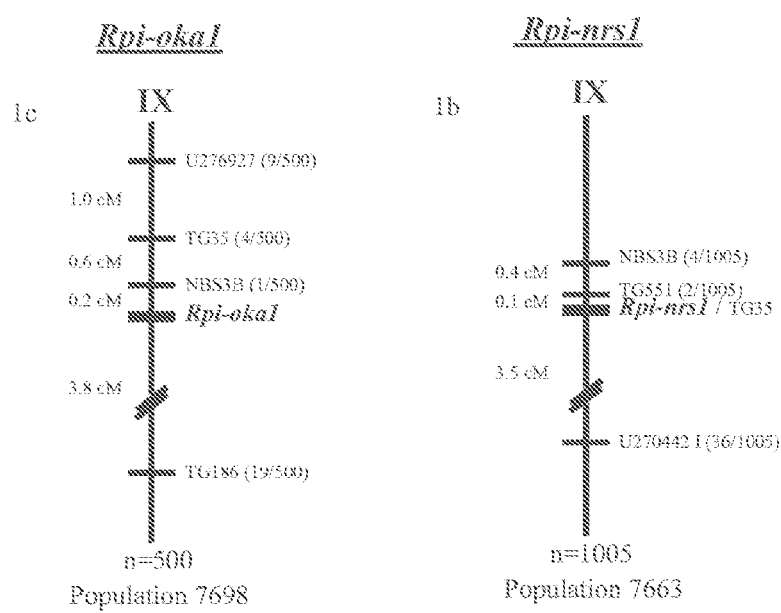
FIG. 9. Genetic linkage maps on chromosome IX of the Rpi-oka1 (a) and Rpi-nrs1 (b) loci mapped in the populations 7698 and 7663 respectively. Numbers on the left side indicate genetic distances (cM). Relative positions of mapped loci are indicated by horizontal lines. The letter n represents the size of each population.

To determine whether the Rpi-oka1 gene segregating in population 7698 was on chromosome IX, we tried to develop and map the chromosome IX specific markers TG35, TG551, TG186, CT183 and T1421 in the initial 50 F1 progeny plants of population 7698. Only TG35 and TG186 were found to be polymorphic between the parental genotypes and were indeed linked to Rpi-oka1 (FIG. 9). In an attempt to develop additional markers for Rpi-oka1, and also markers for Rpi-nrs1, we carried out a bulked segregant analysis (BSA) in combination with NBS profiling in both mapping populations. This led to the identification of 9 bulk specific markers for Rpi-oka1 in 7698 and 8 for Rpi-nrs1 in 7663. Finally, only two resistant bulk specific fragments, one generated with the NBS2/RsaI primer-enzyme combination and the other with NBS3/HaeIII, cosegregated with resistance in the initial 7698 and 7663 populations of 50 and 60 F1 progeny plants, respectively. These fragments were therefore cloned and sequenced. When subjected to a BLAST analysis, both sequences turned out to be highly similar to the Tm-2$^2$ gene on chromosome IX of tomato (Lanfermeijer et al., 2003; 2005). The cloned NBS2/RsaI and NBS3/HaeIII fragments were 350 and 115 by in size and shared 88.3% and 80.3% DNA sequence identity with Tm-2$^2$. These findings suggested that Rpi-nrs1 could be located at the same region on chromosome IX as Rpi-oka1. In an attempt to verify this, specific primers were designed for each fragment and used to develop SCAR markers in both the Rpi-oka1 and Rpi-nrs1 mapping populations. In this way the two NBS-profiling derived markers NBS3A and NBS3B were developed for population 7663 and 7698, respectively. Subsequently, the positions of these markers relative to Rpi-nrs1 and the chromosome IX specific markers TG35 and TG551 were determined in the Rpi-nrs1 mapping 7698. Cosgregation of TG35, TG551 and NBS3B with Rpi-nrs1 in the initial F1 population of 60 individuals, confirmed that Rpi-nrs1 was indeed located on chromosome IX, in the same region as Rpi-oka1 (FIG. 9).

In order to develop flanking markers for a recombinant analysis markers linked to TG35 or TG551 were selected from SGN and screened in both populations. Despite low levels of polymorphism, EST based markers U276927 and U270442 I were developed and mapped in populations 7698 and 7663, respectively (Table 4 and FIG. 9). U276927 was mapped 2 cM north of Rpi-oka1 whereas U270442 I was mapped 3.5 cM south of Rpi-nrs1. Subsequently, a recombinant analysis was performed in 500 offspring of population 7698 and 1005 offspring of population 7663, using the flanking markers U276927/TG186 and NBS3B/U270442, respectively. This resulted in the mapping of Rpi-oka1 and Rpi-nrs1 to genetic intervals of 4 cM and 3.6 cM, respectively (FIG. 9).

Tm-2$^2$ Based Allele Mining in S. okadae and S. neorossi

The present inventors adopted a homology based allele mining strategy to clone Rpi-oka1 and Rpi-nrs1.

The first step was to design degenerated primers incorporating the putative start and stop codons of candidate Tm-2 gene homologs (Tm2GH) at the Rpi-oka1 and Rpi-nrs1 loci. Based on an alignment of all the available potato and tomato derived Tm-2$^2$-like sequences in public sequence databases, we designed primers ATG-Tm2-F and TGA-Tm2-R (Table 5). However, no amplicons of the expected size were generated when this primer set was tested on the parental genotypes of both mapping populations. As the ATG-Tm2-F primer sequence was present in the cosegregating NBS profiling derived marker sequence, three new reverse primers (REV-A, -B and -C) were designed 100 bp upstream of the initial TGA-Tm2-R primer site, in a region that was conserved in all the aligned Tm-2$^2$-like sequences. When combined with either ATG-Tm2-F or NBS3B-F, a single amplicon of approximately 2.5 kb was specifically amplified only from the resistant parental genotypes, i.e., oka7014-9 and nrs365-1. These fragments were cloned into the pGEM®-T Easy vector and approximately 96 individual clones from each genotype were sequenced using a primer walk strategy. All the obtained sequences shared 75-80% similarity to Tm-2$^2$. A total of 5 different classes could be distinguished within the oka7014-9 derived sequences whereas the nrs365-1 sequences fell into only 3 different classes. These different classes were subsequently named NBS3B-like or non-NBS3B-like based on the degree of homology to the NBS3B sequence (Table 6).

In an attempt to retrieve the missing C-terminal part of the amplified Tm2GH' s we embarked on a 3'-genome walk using primers GSP1-1, GSP1-2 and GSP2 (Table 5), which were designed approximately 100 bp upstream of the REV-A, -B and -C primers, in order to generate an overlap of 100 bp between the cloned NBS3B-like sequences and clones generated with the genome walk. Three amplicons of ~200 bp were obtained from oka7014-9 and a single one of ~1 kb from nrs365-1. Following cloning, sequencing and alignment to the cloned Tm2GH's, all four clones seemed to fit to clone Tm2 GH-nrs8bis, as the overlapping 100 bp were an exact match. To be able to subsequently amplify full-length Tm2 GH's from the Rpi-oka1 and Rpi-nrs1 loci we designed a novel reverse primer (TAA-8bis-R) (Table 5) based on the alignment of the full-length Tm2GH-nrs8bis sequence with the Tm2$^2$ sequence from tomato (FIG. 2). As the original TGA stop codon was not present in the Tm2 GH-nrs8bis sequence we included the next in-frame stop-codon (TAA) which was situated 12 bp downstream.

Full-length amplification of Tm2 GH's from oka7014-9 and nrs365-1 was subsequently pursued with high fidelity Pfu Turbo polymerase using primers ATG-Tm2-F and TAA-8bis-R. Amplicons of ~2.6 kb were cloned into the pGEM®-T Easy Vector and sequenced. Three different types of clones were obtained from OKA7014-9, one of which harbored an ORF of the expected size (Tm2GH-oka1 bis). All the clones obtained from NRS365-1 were identical to each other and also contained the expected ORF. Clone Tm2GH-nrs1.9 was chosen together with Tm2GH-oka1 bis for further genetic analysis.

Before targeting Tm2GH-oka1 bis and Tm2GH-nrs1.9 for complementation analysis, we needed to confirm that the selected Tm2GH's indeed mapped to the Rpi-oka1 and Rpi-nrs1 loci. When tested as SCAR markers in the initial mapping populations, both markers cosegregated with resistance. Upon amplification of ATG-Tm2-F and TAA-8bis-R in the set of recombinants which defined the Rpi-oka1 and Rpi-nrs1 loci, amplicons of the expected size were indeed only generated from late blight resistant recombinants, confirming that both Tm2GA's were indeed good candidates for Rpi-oka1 and Rpi-nrs1. However, there were resistant recombinants, 2 in the Rpi-oka1 mapping population and 1 in the Rpi-nrs1 mapping population, which did not give the expected PCR product, suggesting that both loci could in fact harbor a tandem of two functional R genes.

Analysis of the Rpi-oka1 and Rpi-nrs1 ORFs

Gene Structure of Rpi-oka1 and Rpi-nrs1

The 5'-terminal structure of Rpi-oka1 and Rpi-nrs1 was determined by comparing the amplicon sequences with cDNA fragments generated by 5' rapid amplification of cDNA ends (RACE). RACE identified 5' Rpi-oka1 and Rpi-nrs1 specific cDNA fragments comprising 5'-untranslated regions of 83 nucleotides (nt) for Rpi-oka1 and 5 nt for Rpi-nrs1. Both genes are intron free. The open reading frames of Rpi-oka1 and Rpi-nrs1 encode predicted peptides of 891 and 905 amino acids, respectively. In addition to the 14 amino acid insertion in the N-terminal region of Rpi-nrs1, only two other amino acids differ between Rpi-oka1 and Rpi-nrs1. At position 548 and 753, Rpi-oka1 harbours an asparagine and arginine residue whereas the corresponding residues in Rpi-nrs1 are tyrosine and lysine, respectively (FIG. 8). However, the substituted residues have the same characteristics. Asparagine and tyrosine belong to the group of hydrophobic residues whereas arginine and lysine are positively charged residues. The protein sequences of both genes harbor several conserved motifs of the CC-NBS-LRR class of R proteins (FIG. 8). A coiled-coil (CC) domain is located in the N-terminal parts of the proteins between amino acids 1 and 183 for Rpi-oka1 and between 1 and 198 for Rpi-nrs1. In the first 183 or 198 residues 4 pairs of putative heptad motifs composed of hydrophobic residues could be recognized in Rpi-oka1 and Rpi-nrs1 sequences respectively. A NB-ARC (nucleotide-binding site, apoptosis, R gene products, CED-4) domain could be recognized in the amino acid stretch between residues 183 or 198 and 472 or 486 respectively (Ploop, Kinase-2, GLPL) (Van der Bierzen and Jones 1998). The C terminal half of Rpi-oka1 and Rpi-nrs1 comprises a series of 15 LRR motifs of irregular size that can be aligned according to the consensus sequence LxxLxxLxxLxLxxC/N/Sx(x) LxxLPxx (where x is any amino acid) (McHale et al. 2006). A PROSITE analysis (Hofmann et al. 1999) identified 4 N-glycosylation sites, 7 Casein kinase II phosphorylation sites, 10 protein kinase C phosphorylation sites, 6 N-myristoylation sites and 1 Camp- and Cgmp-dependent protein kinase phosphorylation site.

At the protein level, Rpi-oka1 and Rpi-nrs1 share 75% amino acid identity with the Tm-$2^2$ protein sequence. Interestingly, the lowest homology was found in the LRR domain where the Tm-$2^2$ shares only 62% identity with Rpi-oka1 and Rpi-nrs1. In contrast, the coiled-coil and NB-ARC domains of Rpi-oka1 andf Rpi-nrs1 share 87% amino acid sequence identity with the same regions of Tm-22.

TABLE 4

Characteristics of *Phytophthora infestans* isolates used to determine the specificity of Rpi-oka1 and Rpi-nrs1

| Isolate ID | Country of origin | Isolation year | Host | Mating type | RACE | Phenotype |
|---|---|---|---|---|---|---|
| 90128 | Geldrop, The Netherlands | 1990 | Potato | A1 | 1.3.4.7.(8) | Resistant |
| H30P04 | The Netherlands | | Potato | | 7 | Resistant |
| IPO-C | Belgium | 1982 | Potato | | 1.2.3.4.6.7.10.11 | Resistant |
| USA618 | Toluca, Valley, Mexico | unknown | Potato | A2 | 1.2.3.6.7.11 | Resistant |
| VK98014 | Veenkolonién, The Netherlands | 1998 | Potato | A1 | 1.2.4.11 | Resistant |
| IPO-428-2 | The Netherlands | 1992 | Potato | | 1.3.4.7.8.10.11 | Resistant |
| NL00228 | The Netherlands | 2000 | Potato | | 1.2.4 | Resistant |
| Katshaar | Katshaar, The Netherlands | | Potato | | 1.3.4.7.10.11 | Resistant |
| F95573 | Flevoland, The Netherlands | 1995 | Potato | A1 | 1.3.4.7.10.11 | Resistant |
| 89148-09 | The Netherlands | 1989 | Potato | | 0 | Resistant |
| EC1 | Ecuador | | Potato | | 3.4.7.11 | Susceptible |

TABLE 5A

Overview of markers used to map Rpi-oka1 and Rpi-nrs1

| Marker | Primer orientation | Primer sequence | SEQ ID NO. | annealing temperature | Enzyme |
|---|---|---|---|---|---|
| NBS3A | F | GAAGTTGGAGGCGATTCAAGG | 72 | 56 | cfr131 (c) |
| | R | GGCTTGTAGTGTATTGAAGTC | 73 | | |
| NBS3B | F | CCTTCCTCATCCTCACATTTAG | 74 | 65 | a.s. |
| | R | GCATGCCAACTATTGAAACAAC | 75 | | |
| TG35 | F | CACGGAGACTAAGATTCAGG | 76 | 60 | HhaI$^a$/XapI$^b$ (c) |
| | R | TAAAGGTGATGCTGATGGGG | 77 | | |
| TG551 | F | CCAGACCACCAAGTGGTTCTC | 78 | 56 | TaqI (c) |
| | R | AACTTTCAGATATGCTCTGCAG | 79 | | |
| TG186 | F | AACGGTGTACGAGATTTTAC | 80 | 58 | HphI (c) |
| | R | ACCTACATAGATGAACCTCC | 81 | | |
| U270442 I | F | GGATATTATCTTGCAACATCTCG | 82 | 55 | XapI (r) |
| | R | CTTCTGATGGTATGCATGAGAAC | 83 | | |

TABLE 5A-continued

Overview of markers used to map Rpi-oka1 and Rpi-nrs1

| Marker | Primer orientation | Primer sequence | SEQ ID NO. | annealing temperature | Enzyme |
|---|---|---|---|---|---|
| U276927 | F | GCATTAGCGCAATTGGAATCCC | 84 | 58 | HphI (c) |
|  | R | GGAGAGCATTAGTACAGCGTC | 82 |  |  | a.s.: allele specific
(c): coupling phase
(r): repulsing phase

TABLE 5b

Overview of primers used for genome walking based on NBS3B-like sequences, primers targeting the start and stop codons of Rpi-oka1 and Rpi-nrs1 and 5' RACE primers.

| Primer pair | Primer orientation | Primer sequence | SEQ ID NO. | Annealing temperature |
|---|---|---|---|---|
| NBS-GSP1-1 | F | tccaaatattgtcgagttggg | 86 | / |
| NBS-GSP2 | F | gctttggtgcagacatgatgc | 87 | / |
| REV-A | R | ggttgtctgaagtaacgtgcac | 88 | 55 |
| REV-B | R | tgcacggatgatgtcagtatgcc | 89 | 55 |
| REV-C | R | caacttgaagttttgcatattc | 90 | 55 |
| ATG-Tm2F | F | atggctgaaattcttctcacagc | 91 | 55 |
| TAA-8bisR | R | ttatagtacctgtgatattctcaac | 92 | 55 |
| ATG2-Tm2F | F | atgaattattgtgtttacaagacttg | 93 | 55 |
| TGA-Tm2R | R | tgatattctcaactttgcaagc | 94 | 55 |
| GSP1-5 race | R | gaacactcaaattgatgacagacatgcc | 95 | 67 |
| GSP2-5 race | R | cccaaaccgggcatgccaactattg | 96 | 67 |

TABLE 6

Classification of Tm2 homologs, amplified from the resistant parents of S. neorossii (1a) and S. okadae (1b), according to a restriction pattern and NBS3B homology (marker closely linked to both R loci).

| Digestion pattern groups | Clone | NBS3B groups |
|---|---|---|
| *1a S. neorossii* | | |
| 1 | 24 | non-NBS3B-like |
| 2 | 22 |  |
|  | 23 |  |
| 3 | 25 | NBS3B-like |
|  | 27 |  |
|  | 28 |  |
|  | 29 |  |
|  | 30 |  |
|  | 31 |  |
|  | 8bis |  |
| *1b S. okadae* | | |
| 1 | 7 | NBS3B-like |
|  | 8 |  |
|  | 9 |  |
|  | 10 |  |
|  | 11 |  |
|  | 12 |  |
|  | 13 |  |
|  | 14 |  |
|  | 16 |  |
|  | 17 |  |
|  | 20 |  |
|  | 21 |  |
|  | 1bis |  |
|  | 6bis |  |
|  | 7bis |  |
| 2 | 2 | non-NBS3B-like |
|  | 3 |  |
|  | 4 |  |
|  | 3bis |  |
|  | 4bis |  |
| 3 | 1 |  |
|  | 5 |  |
|  | 6 |  |
|  | 5bis |  |
| 4 | 19 |  |
| 5 | 18 |  |

Example 4A

Transient Complementation in *Nicotiana benthamiana*

Depending on the resolution of relevant genetic mapping studies and the size of the candidate gene family, an allele mining approach can generate many candidate genes which need to be functionally analyzed. To date functional analyses of candidate R gene homologues (RGH) typically require stable transformation of a susceptible genotype for complementation purposes. This is a time consuming and inefficient approach as it takes several months at the least to generate transgenic plants that can functionally be analyzed. In the current study, we have exploited the finding that *Nicotiana benthamiana* is susceptible to *P. infestans*, despite previous reports (reference Kamoun et al., 1998), to develop a *Agrobacterium* transient complementation assay (ATCA) for R genes that confer resistance against *P. infestans*.

*Agrobacterium* Transient Transformation Assays (ATTA)

*Agrobacterium* transient transformation assays (ATTA) were performed in *Nicotiana benthamiana* followed by detached leaf assays's using appropriate *P. infestans* isolates. Four week old plants were infiltrated with a solution of *Agrobacterium tumefaciens* strain COR308 (Hamilton et al., 1996), harboring putative R gene candidates. Two days before infiltration, *A. tumefaciens* was grown over night at 30° C. in LB medium with tetracycline (12.5 mg/ml) and spectinomycine or kanamycine (100 mg/ml and 50 mg/ml respectively). After 16 h growth, the $OD_1$ was measured and 50 ml of YEB medium was inoculated with x µl of LB culture and grown overnight at 30° C. in order to reach an $OD_2$ of 0.8 the next day [x=z/OD1 with z=80000 (2power (delta t/2)]. The following day, 45 ml of YEB culture was centrifuged for 8 mins at 4000 rpm. The pellet was resuspended with y ml of MMA containing 1 ml/L of acetosyringone. $Y=22 \times OD_2$ enabled the standardization of the different cultures at an $OD_3$ of 2.0. Every resuspended pellet was incubated for an hour at room temperature. Then the lower side of the leaf was infiltrated with MMA culture at an $OD_4$ of 0.1 using a 2 ml syringe. Two days post infiltration, a DLA was performed as mentioned above. Infection phenotypes (resistant or susceptible) were assessed from 4 to 7 days post inoculation. Detached leaf assays were carried out as described by Vleeshouwers et al., (1999) using two *P. infestans* isolates, IPO-complex which is not virulent on Rpi-oka1, 2 or Rpi-nrs1 and isolate EC1 which is virulent on all three genes. Leaves were inoculated with 10 µl droplets of *Phytophthora infestans* inoculum ($5 \times 10^4$ zoospores/ml) on the abaxial side and incubated at 15° C. for 6 days in a climate chamber with a photoperiod of 16 h/8 h day/night. At 6 days post inoculation, leaves showing sporulation were scored as susceptible whereas leaves showing no symptoms or necrotic lesions were scored as resistant. Three independent transient complementation assays were carried out in triplicate with both isolates. For each replicate, leaf numbers 4, 5 and 6 when counting from the bottom of the plant, were agro-infiltrated and subsequently challenged with *P. infestans*. Five days post inoculation with IPO—C, 60-70% of the leaves transiently expressing the candidate Rpi-oka1 or Rpi-nrs1 genes displayed a typical HR reponse, as did the positive control plants transiently expressing the functional Rpi-sto1 gene (Vleeshouwers et al, 2008), although in the latter case complementation efficiency was significantly higher (80-90% of the challenged leaves showed an HR). In contrast, leaves expressing abptGH-a, a non-functional paralogue of Rpi-abpt (Lokossou et al., in preparation) were fully susceptible. In the case of EC1, all agro-infiltrated leaves were susceptible except for those infiltrated with Rpi-sto1, which confers resistance to EC1. These data matched with the resistance spectrum of Rpi-oka1 and Rpi-nrs1 and therefore suggested that the candidate genes represented Rpi-oka1 and Rpi-nrs1.

Example 4B

Complementation Analysis through Stable Transformation of cv. Desiree

To confirm the results obtained with the transient complementation assays in *N. benthamiana*, the binary Gateway constructs harbouring Tm2GH-oka1b and Tm2GH-oka1.9 were transferred to the susceptible potato cultivar Desiree through

*Agrobacterium* mediated transformation. As a control we also transformed cv. Desiree with construct pSLJ21152, a binary construct harbouring a 4.3 kb fragment carrying the putative Rpi-oka1 promoter, ORF and terminator sequence (see Example 6). Primary transformants harbouring the transgenes of interest were tested for resistance to *P. infestans* in detached leaf assays. Surprisingly, only the genetic construct harbouring the 4.3 kb Rpi-oka1 fragment was able to complement the susceptible phenotype; 8 out of 9 primary transformants were resistant. All 22 Tm2GH-oka1b and 17 Tm2GH-oka1.9 containing primary transformants were susceptible to *P. infestans*.

Alignment of the Tm2GH-oka1 b and Tm2 GH-oka1.9 sequences to the 4.4 kb Rpi-oka1 fragment revealed the presence of an additional in-frame ATG start codon 99 nt upstream from the start codon that was initially used as basis for the allele mining experiments. This finding, together with the negative complementation results obtained with the Tm2GH-oka1b and Tm2 GH-oka1.9 and the positive complementation result with 4.3 kb Rpi-oka1 fragment suggested that the 5' most start codon represents the actual start of the functional Rpi-oka1 and Rpi-nrs1 ORFs.

Transient Complementation Assays Using 5' Extended Allele Mining Products

In an attempt to mine the putatively full-length Rpi-oka1 and Rpi-nrs1 genes from oka7014-9 nrs365-1, respectively, genomic DNA of both genotypes was subjected to long range PCR using the primers ATG2-Tm2F and TAA-8bR (Table 2). Amplicons of the expected size were cloned into the pGEM®-T Easy vector and sequenced. Clones obtained from oka7014-9 were all the same and identical to the corresponding sequence in pSLJ21152 (see Example 6). Clones obtained from nrs365-1 were also all identical but contained an insertion of 42 nt in the 5' extended region compared to those obtained from oka7014-9. Both sequences were subsequently inserted into the Gateway® binary expression vector in between the regulatory elements of the Rpi-bib3 gene (Lokossou et al., in preparation) and targeted for transient complementation analysis in *N. benthamiana*, together with the original Tm2GH-oka1b and Tm2GH-oka1.9 constructs and pSLJ21152. Both full-length genes and the 4.3 kb Rpi-oka1 gene showed comparable resistance levels as the positive control Rpi-sto1 (80-90% of the challenged leaves showed an HR response), whereas the shorter gene constructs again displayed significantly lower levels of resistance (60-70% HR), indicating that the full-length amplicons derived from oka7014-9 and nrs365-1 represent Rpi-oka1 and Rpi-nrs1, respectively.

Example 5

Identification, Mapping and Cloning of Rpi Genes from *S. mochiquense*

Mapping Rpi Genes in *S. mochiquense*
Rpi-mcq1

Figure 10:
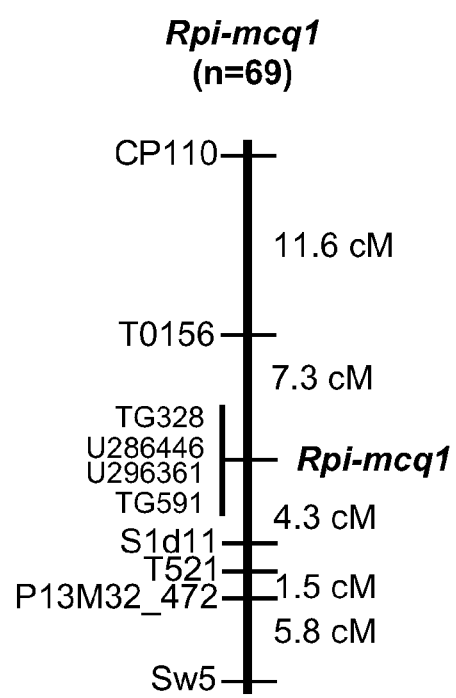
FIG. 10 Map position of the late blight resistance gene Rpi-mcq1 from *S. mochiquense.*

Rpi-mcq1 was previously mapped generally to the bottom of the long arm of chromosome IX (Smilde et al, 2005) although no fine mapping or characterisation was disclosed. Flanking markers that span a distance of 20 cM were developed in addition to a marker (TG328) that co-segregated with Rpi-mcq1 in a population of 68 individuals. To fine map Rpi-mcq1, a total of 72 AFLP primer combinations were used to look for more closely linked markers. One polymorphic band P13M32_472 was identified to map on the southern side of the gene. An additional 5 CAPS markers (Table 7) were developed from released sequence of the tomato BAC clones C09HBa0165P17 and other known RFLP markers from chromosome IX within the SGN database. In this way, Rpi-mcq1 was mapped to a 11.6 cM region, flanked by markers T0156 and S1d11, and co-segregating with CAPS markers TG328, U286446, U296361, and TG591 (FIG. 10).

Figure 11:
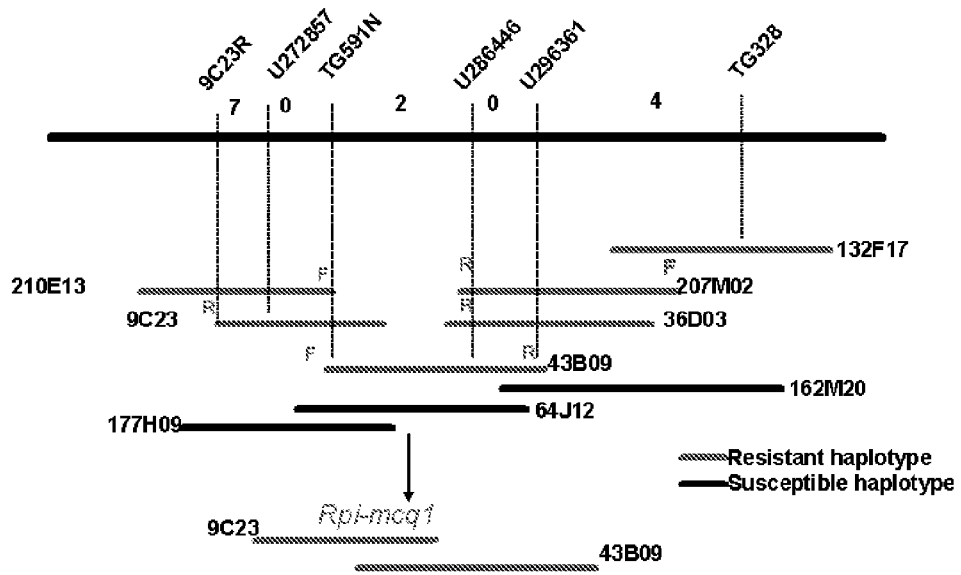
FIG. 11 Contig of BAC clones identified from the K182 BAC library and covering the genomic region containing Rpi-mcq1.

The original 384-well plates for each of the BAC libraries were replicated onto solid LB medium. Colonies from each plate were scraped by rows and columns and screened for the presence of the relevant marker. Single clones from 384-well plates were selected. One of the BAC-end sequences from the clones selected from the K182 library was highly similar to the gene Tm-$2^2$. Additionally two of the BAC-end sequences for the K182 library were similar to several different resistance proteins identified in *Solanum tuberosum, Malus baccata, Populus balsamifera, Populus trichocarpa, Medicago truncatula* and *Lens culinaris*. An expanded population consisting of 2502 individuals was used to identify recombinants between the flanking markers T0156 and S1d11. A total of 163 recombinants were found and used for analysis the co-segregating markers TG328, U286446, U296361, and TG591. As a result, Rpi-mcq1 was mapped to a 0.32 cM region of chromosome IX, flanked by markers U286446 and 9C23R (marker developed from a BAC end sequence), and co-segregating with markers U272857 and TG591 (FIG. 10). Based on the order of the CAPS markers, the corresponding BAC clones were ordered and used to construct a contig which was spanned from 9C23R to TG328 (FIG. 11). The region predicted to contain Rpi-mcq1 was covered by two

TABLE 7

CAPS markers used for mapping of Rpi-mcq1

| Marker | Primer sequence (5'-3') | SEQ ID NO: | Tm (° C.) | Restriction enzymes |
|---|---|---|---|---|
| T0156 | F: AAGGCAGGAACAAGATCAGG | 97 | 55 | RsaI |
|  | R: TTGACAGCAGCTGGAATTG | 98 |  |  |
| TG328 | F: AATTAAATGGAGGGGGTATC | 99 | 50 | AluI |
|  | R: CCTTTGAATGTCTAGTACCAG | 100 |  |  |
| U296361 | F: CAGAAGCAGCTGACTCCAAA | 101 | 55 | HincII |
|  | R: TTCAACAGTGAGAGAGCCACA | 102 |  |  |
| U286446 | F: GCACAAGCACAGTCTGGAAA | 103 | 55 | HaeIII |
|  | R: GCTGCATTAATAGGGCTTGC | 104 |  |  |
| TG591 | F: TACTCGTGCAAGAAGGAACG | 105 | 55 | HaeIII, |
|  | R: CCAACTTGTTTGGCTATGTCA | 106 |  | HpaII |
| U272857 | F: GTGGTCTTTTGAGGCAGAGC | 107 | 55 | XhoI |
|  | R: AGATTCGCCGTCTGTGAAGT | 108 |  |  |
| 9C23R | F: TCTTGCCAAGCAGGTCTTTT | 109 | 55 | HinfI |
|  | R: CAGCCATTAGGCATTTGACA | 110 |  |  |
| S1d11 | F: CTGGTCCTATAGGGTTACCATT | 111 | 55 | ApoI |
|  | R: AGAACCGCACCATCATTTCTTG | 112 |  |  |
| T0521 | F: CCACTTCACCCACCTGGTAT | 113 | 55 | HaeIII |
|  | R: AGCTTTGCAGACATTACATGG | 114 |  |  |

High Resolution Mapping and Cloning of Rpi-mcq1
BAC Library Screening

In the K182 library, the marker U279456 was amplified from nine pools (Table 1a). This marker is allele specific and is linked to the susceptible haplotype in K182. The other three markers (U282757, U296361 and TG591) are CAPS markers and thus restriction digestion was used to assign haplotype to the identified BACs. Analysis of these three markers showed that between three and seven BAC pools contained BAC clones with the marker alleles from the resistant haplotype (Table 1a, FIG. 4d-4e).

High Resolution Mapping and Cloning of Rpi-mcq1

Eight BAC pools from the K182 library which were positive to U282757, U296361, TG591 or U279465, markers which are closely linked to Rpi-mcq1 were randomly chosen.

overlapping BAC clones, 9C23 and 43B09, which were identified from the resistant haplotypes. These two BAC clones were sequenced and subcloned into the binary cosmid vector pCLD04541 by partial digestion using Sau3Al. Analysis of the BAC sequence indicated that it contains 2 complete ORFs and 2 incomplete ORFs which are similar to the Tm$2^2$ resistance gene against ToMV. The 2 complete ORFs were predicted to be the candidates for Rpi-mcq1 and cosmid clones containing these two ORFs (Rpi-mcq1.1 and Rpi-mcq1.2) were identified and introduced into the susceptible potato variety Desiree, tomato cultivar Moneymaker and *N. benthamiana* by Agobacterium-mediated transformation.
Analysis of the Rpi-mcq1 ORFs We sequenced the two candidate BAC clones 9C23 and 43B09. BAC clone K182_43B09 is 103,863 by long and has been completely sequenced. BAC clone K182_9C23 has been sequenced to 3 contigs, K182_9C23_2699 (62,389 bp), K182_9C232732 (22,072 bp), and K182_9C23_2737 (10,119 bp). After alignment between the BAC sequences, K182_43B09 was found to contain all of K182_9C23_2737 and approximately half of K182_9C23_2732 which indicates the overlapping regions of the two BAC clones.

K182_9C23_2699 was found to contain 3 ORFs and K182_9C23_2732 and K182_9C23_2737 each contained 1 ORF longer than 300 bp. The ORFs from K1829C23_2732 and K182_9C23_2737 were identical to the first and second ORFs from K182_43B09. The first ORF of K182_9C23_2699 encoded a putative NAD dependent epimerase (same gene as CAPS marker U272857). The second encoded a complete CC-NBS-LRR type plant resistance gene protein which is highly similar to ToMV resistance gene Tm2$^2$ and thus is a candidate gene for Rpi-mcq1 (Rpi-mcq1.1). The third ORF encoded an incomplete Tm2$^2$-like protein which contained a partial NBS motif and complete LRR motif. Also there are 5 additional ORFs predicted from the sequence of K182_43B09. The first and third ORFs were predicted to encode RNA-directed DNA polymerases and retrotransposon proteins, the fifth ORF encoded the same gene as CAPS marker U296361. These are not considered to be Rpi-mcq1 candidates as such proteins are not associated with a plant resistance gene function. The second and fourth ORFs are similar to the resistance gene Tm2$^2$. The second ORF encoded a complete gene in which can be found all CC, NB and LRR domains; this was regarded as a second candidate for Rpi-mcq1 (Rpi-mcq1.2). The fourth ORF was predicted to encode a truncated protein due to an early stop codon at amino acid 110.

The two candidate genes for Rpi-mcq1 were subcloned into binary cosmid vector pCLD04541. Rpi-mcq1.1 is 2,589 by long and predicted to encode a CC-NB-LRR protein of 862 amino acids with a calculated molecular weight of 98.2 kDa and a pI of 7.75. The coiled-coil (CC) domain is located in the N-terminal part of the protein between amino acids 1 and 173. In the first 173 residues 12 putative heptad motifs composed of hydrophobic residues could be recognized. A NB-ARC domain which contains all the characterized motifs was present in the amino acid sequence from 173 to 478 (van der Biezen & Jones, 1998). The LRR domain was present in the amino acid sequence from 479 to 862 which comprises a series of 15 LRR motifs of irregular size that can be aligned according to the consensus sequence LxxLxxLxxLxLxxC/N/Sx(x) LxxLPxx (where x is any amino acid) (McHale et al., 2006). The NB-ARC motif 5 (amino acid postions 481-485) overlaps with the start of the LRR domain.

Rpi-mcq1.2 is 2,571 by long and predicted to encode a CC-NBS-LRR protein of 856 amino acids with a calculated molecular weight of 98.0 kDa and a pI of 7.81. The coiled-coil (CC) domain is located in the N-terminal part of the protein between amino acids 1 and 170. The NB-ARC domain is present in the amino acid sequence from 171 to 476 and contains all characterized motifs (van der Biezen & Jones, 1998). The LRR domain was present in the amino acid sequence from 477 to 856 which comprises a series of 15 LRR motifs of irregular size that can be aligned according to the consensus sequence LxxLxxLxxLxLxxC/N/Sx(x) LxxLPxx (where x is any amino acid) (McHale et al., 2006). The NB-ARC motif 5 overlaps with the start of the LRR domain.

Rpi-mcq1.1 and Rpi-mcq1.2 are approximately 77% and 75% identical, respectively, to the Tm2$^2$ protein at the amino acid level, and 81% identical to each other.

Example 6

Introduction of Novel Resistance Genes into Potato and Tomato Genotypes Susceptible to *Phyophthora infestans* and into *N. benthamiana*

Binary Vector with the Rpi-oka1 Gene Under the Control of its Own Promoter and Terminator (the Original Gene)

A 4.3 kb fragment (SEQ. ID. No. 1c) carrying the Rpi-oka1 promoter, open reading frame (ORF) and terminator was amplified by PCR using the primers oka1longF (5'-AGTTATACACCCTACATTCTACTCG-3') (SEQ ID NO: 115) and oka1longR (5'-CTTTGAAAAGAGGCTTCATACTCCC-3') (SEQ ID NO:116) from the BAC clone K39_26619. This fragment was cloned into pGEM-T Easy (Promega) and sequenced to confirm no mistakes had been introduced during PCR. The resulting plasmid was digested with EcoRI and the fragment containing the original gene cloned into the EcoRI site of pBin19. The resulting plasmid was named pSLJ21152. Plasmid pSLJ21152 was introduced into *Agrobacterium tumefaciens* strain AGL1.

Binary Vector with the Rpi-mcq1.1 and Rpi-mcq1.2 Genes Under the Control of their Own Promoters and Terminators (the Original Genes)

The BAC clones K182_9C23 and K182_43B09 are subcloned by partial digestion using Sau3Al into the BamHI site of the binary cosmid vector pCLD04541. The recombinant cosmid vector is packaged using GigaPack Gold (Stratagene) and introduced into *E. coli* strain DH5a. Resulting clones are screened by PCR using primers TG591-F and TG591-R to identify clones containing Rpi-mcq1 candidates and positive clones are selected for end-sequencing. Clones carrying the two Rpi mcq1 candidates are identified by reference to the full BAC sequences of BAC clones K182_9C23 and K182_43B09. Clone pSLJ21153 carries the full sequence of Rpi-mcq1.1 including the promoter and terminator sequences (SEQ. ID. No 2c). This clone also contains an additional resistance gene homologue which lacks a coiled-coil domain and part of the NBS domain and is therefore presumend to be non-functional. To confirm this, an additional clone designated D5 which contains this truncated gene in the absence of Rpi-mcq1.1 is also identified. Clone pSLJ21148 carries the full sequence of Rpi-mcq1.2 including the promoter and terminator sequences (SEQ. ID. No 2d). The clones carrying the full-length candidate Rpi-mcq1 genes and the truncated gene are introduced into *Agrobacterium tumefaciens* strains AGL1 and LBA4404. To ensure no rearrangements of the plasmids have occurred, plasmid is isolated from resulting transconjugants, transformed back into *E. coli* strain DH10-β, digested and compared with digests of the original plasmid stocks.

Potato Transformation

*Agrobacterium tumefaciens* culture(s) with the appropriate antibiotic selection regime are set up and grown for 24 hours with shaking at 28° C. Stem internode sections (without nodes) are harvested from 4-6 week old potato cv. Desiree plants grown in aseptic culture on MS medium (2% sucrose). The internodes are sliced into 1 cm sections and placed into 20 ml of LSR broth. 100 ul of overnight *Agrobacterium tumefaciens* culture is added to stem sections and incubated for 20 minutes at 40 rpm in the dark at 24° C. The stem sections are removed from the *Agrobacterium tumefaciens* suspension, blotted dry and incubated under low light conditions at 18 C for 3 days on LSR1 solid media (around 15-20 explants are plated per dish). Co-cultivated stem sections are then transferred to LSR1 medium with selection antibiotics at around 10 explants per dish. Stem explants are subcultured onto fresh LSR1 media every 7-10 days for around 3-6 weeks or until the appearance of the first small calli. Once the calli have sufficiently developed the stem sections are transferred onto LSR2 media with selection antibiotics. Stem sections are subcultured every 7-10 days until shoots start to develop. Shoots appear within 2 months from the start of transformation. Shoots are removed with a sharp scalpel and planted into MS2R solid media with selection antibiotics. Transgenic plants harbouring appropriate antibiotic or herbicide resistance genes start to root normally within 2 weeks and are weaned out of tissue culture into sterile peat blocks before being transplanted to the glasshouse.

Media
MS Medium for Potato Plantlets
1× Murashige and Skoog medium
2% Sucrose
0.6% Agarose
100 mg/L casein acid hydrolysate
pH 5.7
LSR Broth
Murashige and Skoog medium
3% Sucrose
pH 5.7
LSR1Medium
1× Murashige and Skoog medium
3% Sucrose
2.0 mg/L zeatin riboside
0.2 mg/l NAA
0.02 mg/L $GA_3$
0.6% Agarose
pH 5.7
LSR2Medium
1× Murashige and Skoog medium
3% Sucrose
2.0 mg/L zeatin riboside
0.02 mg/l NAA
0.02 mg/L $GA_3$
0.6% Agarose
pH 5.7
MS2R
1× Murashige and Skoog medium
2% Sucrose
100 mg/L myo-inositol
2.0 mg/L glycine
0.2% Gelrite
pH 5.7

| Media | *Agrobacterium tumefaciens* strain | Antibiotics | T-DNA marker | Selection antibiotic/ herbicide |
|---|---|---|---|---|
| LSR1/ LSR2/ MS2R | GV3101/ LBA4404 | Cefotaxime/ Augmentin at 250 mg/L | nptII | Kanamycin at 100 mg/L |
|  | Agl1 | Timentin at 320 mg/L | bar | Phosphinothricin at 2.5 mg/L |

Tomato Transformation

Tomato seeds are surface sterilised for 2 minutes in 70% ethanol to loosen gelatinous seed coat and then rinsed once with sterile water. The seeds are then sterilised in 10% domestic bleach (e.g. DomestosNortex) solution for 3 hours with shaking and washed 4 times in sterile water. Seeds are put into tubs (20-30 seeds/tub) containing germination medium and incubated at 25° C. in a culture room (16 hour photoperiod, supplemented with Gro-Lux or incandescent light). The seedlings are grown for 7-10 days and used at a stage when cotyledons are young and still expanding and no true leaf formation is visible. Ten milliliters of minimal A medium containing the appropriate antibiotics is inoculated with *A. tumefaciens* strain LBA4404 and grown with shaking at 28C. One milliliter of fine tobacco suspension culture is placed onto plates containing the cell suspension medium solidified with 0.6% agarose or MS medium amended with 0.5 mg/L 2,4-D and 0.6% agarose. Cells are spread around to give an even layer and plates are placed unsealed and stacked in the culture room at 25° C. in low light until the following day. A piece of Whatman no. 1 filter paper is placed on top of the feeder plates, taking care to exclude any air bubbles and ensuring that the paper is completely wetted. Cotyledons are used for transformation as hypocotyls give rise to a high number of tetraploids. In a petri dish, the tips are cut off cotyledons and then two more transverse cuts are made to give two explants of about 0.5 cm long. Explants are transferred to a new petri dish of water to prevent any damage during further cutting. Once a number of explants are collected in the pool, they are blotted dry on sterile filter paper and placed about 30-40 on a feeder plate, abaxil surface uppermost (upside down). Petri-dishes are placed unsealed and stacked at 25° C. under low light intensity for 8 hours. The *Agrobacterium* culture is spun down and resuspended in MS medium containing 3% sucrose to an $OD_{600}$ of 0.4-0.5. The bacterial suspension is transferred to a petri dish and the explants from one feeder plate are immersed in the suspension. These are then removed and blotted on sterile filter paper before returning them to the original feeder plate, again taking care not to damage the tissue. No particular period of time is required in the bacteria, just enough time to ensure that the pieces have been completely immersed. Plates are returned to the same conditions as used in the pre-incubation phase (25° C. under low light intensity and co-cultivated for 40 hours. The explants from the feeder layers are placed (12 explants per Petri dish) onto tomato regeneration plates containing Augmentin or carbenicillin at 500 ug/ml and kanamycin at 100 ug/ml select for the T-DNA transformation marker. The cotyledons are placed right side upwards so that they curl into the medium ensuring good contact between the cut edges of the leaf and the nutrients and antibiotics in the medium. Agargel is used as the setting agent as it produces a soft medium into which the pieces can be pushed gently. Plates are left unsealed and returned to the previous culture conditions (25° C. under low light intensity). Explants are transferred to fresh medium every 2-3 weeks. Once regenerating material is too large for petri dishes it is put into larger screw capped glass jars. Shoots are cut from the explants and put into rooting medium with Augmentin at 200 ug/ml and kanamycin at 50 ug/ml. To transfer to soil, as much of the medium as possible is removed by washing the roots gently under running water. Plant are transferred carefully to hydrated, autoclaved Jiffy pots (peat pots) and kept enclosed to maintain high humidity while in the growth room. Humidity is gradually decreased. Once roots can be seen growing through the Jiffy-pots the plants are transferred to the glasshouse.

| REGENERATION | |
|---|---|
|  | /Litre |
| MS salts | 1x |
| myo-inositol | 100 mg |
| Nitsch's vitamins | 1 ml of 1000X stock |
| Sucrose | 20 g |

REGENERATION

| | /Litre |
|---|---|
| Agargel | 4 g |
| pH 6.0 (KOH) | |
| Autoclave | |
| Zeatin Riboside (trans isomer) | 2 mg |

(Filter sterilise and add after autoclaving)

Nitsch's Vitamins

| | mg/l | Final conc. 1000x stock (mg/100 ml) |
|---|---|---|
| Thiamine | 0.5 | 50 |
| Glycine | 2.0 | 200 |
| Nicotinic acid | 5.0 | 500 |
| Pyridoxine HCl | 0.5 | 50 |
| Folic acid | 0.5 | 50 |
| Biotin | 0.05 | 5 |

At 1000× not all vitamins go into solution. Keep at 4° C. and shake before using.

Rooting

| | /Litre |
|---|---|
| MS medium | 0.5X |
| Sucrose | 5 g |
| Gelrite | 2.25 g |
| pH 6.0 (KOH) | |

Media

Seed Germination

| | /Litre |
|---|---|
| MS medium | 1x |
| Glucose | 10 g |
| Agarose | 6 g |
| pH 5.8 | |

Pour into round Sigma 'margarine' tubs.

Minimal A

| | /Litre |
|---|---|
| $K_2HPO_4$ | 10.5 g |
| $KH_2PO_4$ | 4.5 g |
| $(NH_4)_2SO_4$ | 1.0 g |
| Na citrate•$2H_2O$ | 0.5 g |
| Autoclave in 990 ml | |
| Before use add; | 1.0 ml of 1M $MgSO_4$•$H_2O$ |
| | 10 ml of 20% Glucose |

For plates;
Make the above in 500 ml and autoclave.
Separately autoclave 15 g Bactoagar in 490 ml $H_2O$
Add $MgSO_4$ and glucose and combine.

*Nicotiana benthamiana* Transformation

*N. benthamiana* plants are grown until they are 10-20 cm high, but before they start to flower. *Agrobacterium tumefaciens* cultures are initiated with the appropriate antibiotic selection regime and grown for 24 hours with shaking at 28° C. The following day, the *A. tumefaciens* cultures are spun down and resuspended in Murashige and Skoog medium containing 3% sucrose. Young *N. benthamiana* leaves (up to 10 cm in diameter) are harvested and surface sterilised in 1% fresh sodium hypochlorite containing a few drops of Tween 20 to act as a surfactant for 20 minutes. The leaves are then washed well in sterile water, cut into 1-2 cm squares with a sharp scalpel and immersed into the *Agrobacterium tumefaciens* suspension. Ensuring that all the leaves have been fully wetted, they are then briefly blotted dry and placed onto co-cultivation medium for 3 days. Following this, co-cultivated leaf pieces are transferred onto selection medium with appropriate antibiotics at around 10 explants per dish. Explants are subcultured onto fresh media every 7-10 days for around 1-2 months until the appearance of the first shoots. Shoots are removed with a sharp scalpel and planted into rooting media with selection antibiotics. Transgenic plants harbouring appropriate antibiotic or herbicide resistance genes start to root normally within 2 weeks and can be weaned out of tissue culture into sterile peat blocks before being transplanted to the glasshouse.

MS Broth
1× Murashige and Skoog medium
3% Sucrose
pH 5.7

Co-Cultivation Medium
1× Murashige and Skoog basal salt mixture
1× Gamborg's B5 vitamins
3% Sucrose
0.59 g/L MES
1.0 mg/L BAP
0.1 mg/l NAA
0.6% Agarose
pH 5.7

Selection Medium
1× Murashige and Skoog basal salt mixture
1× Gamborg's B5 vitamins
3% Sucrose
0.59 g/L MES
1.0 mg/L BAP
0.1 mg/l NAA
0.4% Agargel
pH 5.7

Rooting Medium
½ strength Murashige and Skoog medium
0.5% Sucrose
0.25% Gelrite
pH 5.8

| Media | *Agrobacterium tumefaciens* strain | Antibiotics | T-DNA marker | Selection antibiotic/ herbicide |
|---|---|---|---|---|
| Selection Medium/ Rooting Medium | GV3101/ LBA4404 | Cefotaxime/ Augmentin at 500 mg/L | nptII | Kanamycin at 100 mg/L |
| | Agl1 | Timentin at 320 mg/L | bar | Phosphinothricin at 2.0 mg/L |
| | | | hgh | Hygromycin at 10 mg/L |

Complementation Analysis (Rpi-oka1).

A total of 37 S. tuberosum cv. Desiree plants capable of growth on kanamycin were selected as putative Rpi-oka1 transformants. Following transfer to the glasshouse, leaves were excised and used in a detached leaf assay with P. infestans isolates 90128 and 'Superblight' to determine whether the transgene conferred blight resistance. Of the 37 transformants, 31 were confirmed as being resistant and did not show any signs of blight infection. Some plants exhibited signs of a hypersensitive response localised to the inoculation site. The remaining 6 plants were susceptible to both isolates, as was the control (non-transformed Desiree). The phenotype of the transgenic plants correlated exactly with amplification of the Rpi-oka1 ORF by PCR, all plants from which the Rpi-oka1 could be amplified were confirmed as resistant. The Rpi-oka1 transgene also conferred resistance to a range of P. infestans isolates as detailed in Table 6.1. All transgenic plants tested were susceptible to isolate EC1, showing that the specificity of Rpi-oka1 was retained in the transgenic plants and that the resistance phenotype was not due to constitutive activation of defence pathways by the transgene.

Transgenic tomato cv. Moneymaker plants carrying Rpi-oka1 were also shown to be resistant to P. infestans isolate 90128. A total of 21 S. lycopersicum cv. Moneymaker plants capable of growth on kanamycin were selected as putative Rpi-oka1 transformants. Following transfer to the glasshouse, leaves were excised and used in a detached leaf assay with P. infestans isolate 90128 to determine whether the transgene conferred blight resistance. Of the 21 transformants, 13 were confirmed as being resistant and did not show any signs of blight infection. Some plants exhibited signs of a hypersensitive response localised to the inoculation site. The remaining 8 plants were susceptible isolates 90128, as was the control (non-transformed Moneymaker). The phenotype of the transgenic plants was generally correlated with amplification of the Rpi-oka1 ORF by PCR, most plants from which the Rpi-oka1 could be amplified were confirmed as resistant. However, two plants contained Rpi-oka1 as determined by PCR, yet were susceptible indicating that the transgene had either been silenced or was inserted into a transcriptionally inactive region of the recipient tomato genome. All plants from which Rpi-oka1 could not be amplified were susceptible to P. infestans.

Spectrum of P. infestans Isolates Against which Rpi-Oka1 Confers Resistance

Detached leaves of transgenic potato cv. Desiree carrying Rpi-oka1 were inoculated with a range of P. infestans isolates (Table 6.1) to determine the range of isolates against which Rpi-oka1 confers resistance. Of the 11 isolates tested, only isolate EC1 from Ecuador was able to overcome Rpi-oka1 and cause disease on the inoculated plants.

Complementation Analysis (Rpi-mcq1.1 and Rpi-mcq1.2).

A total of 22 and 20 putative transgenic lines of S. tuberosum cv Desiree were obtained following transformation with, pSLJ21153 (Rpi-mcq1.1) and pSLJ21148 (Rpi-mcq1.2), respectively. Following transfer to the glasshouse, detached leaf assays were done using P. infestans isolates 90128, EC1, Hica and IPO-complex. For construct pSLJ21153, 12 transgenic lines were shown to be resistant to isolates 90128 and EC1, but susceptible to Hica and IPO-complex. For construct pSLJ21148, transgenic lines showed enhanced resistance to Hica when inoculated at low concentrations ($1\times10^4$ zoospores ml$^{-1}$), but were susceptible to 90128, EC1 and IPO-complex. Rpi-mcq1.2 present in this construct also conferred partial resistant to the isolates 'Superblight' and MP618 (Table 6). Transgenic potato lines transformed with cosmid D5 which contained the truncated resistance gene honolog also present on pSLJ21153 were shown to be susceptible to all P. infestans isolates tested.

The two constructs (pSLJ21153 and pSLJ21148) carrying Rpi-mcq1.1 and Rpi-mcq1.2, respectively were transformed into tomato cv. Moneymaker. Two lines positive for Rpi-mcq1.1 and 11 lines positive for Rpi-mcq1.2 were identified by PCR using gene specific primers. The two transgenic lines carrying Rpi-mcq1.1 conferred resistant to 90128 and EC1. Transgenic Moneymaker lines carrying Rpi-mcq1.2 or the truncated R gene homolog which is also present on construct pSLJ21153 with Rpi-mcq1.1 (cosmid D5) were susceptible to 90128 and EC1.

Spectrum of P. Infestans Isolates Against which Rpi-mcq1.1 and Rpi-mcq1.2 Confer Resistance A wider range of P. infestans isolates were tested to determine their virulence/avirulence on Rpi-mcq1.1 and Rpi-mcq1.2 (Table 6.1). Of 12 isolates tested, Rpi-mcq1.1 conferred resistance to 6 isolates, and Rpi-mcq1.2 conferred partial resistance to 3 isolates (Table 6.1).

TABLE 6.1

Response of Rpi-oka1 and Rpi-mcq1 transgenic potato plants against a range of P. infestans isolates

| Isolate | Country of Origin | Race (if known) | Rpi-oka1 phenotype | Rpi-mcq1.1 phenotype | Rpi-mcq1.2 phenotype |
|---|---|---|---|---|---|
| 90128 | The Netherlands | 1.3.4.7.8.9.10.11 | Resistant | Resistant | Susceptible |
| IPO-0 | | | Resistant | Resistant | Susceptible |
| IPO-Complex | Belgium | 1.2.3.4.6.7.10.11 | Resistant | Susceptible | Susceptible |
| 'Superblight' | United Kingdom | | Resistant | Susceptible | Partially resistant |
| Hica | United Kingdom | | Resistant | Susceptible | Partially resistant |
| MP717 | Poland | 1.2.3.4.5.6.7.9.10.11 | Resistant | Resistant | Susceptible |
| MP778 | Poland | 1.3.4.5.6.7.9.10.11 | Resistant | Resistant | Susceptible |
| MP674 | Poland | 1.2.3.4.5.6.7.10.11 | Resistant | Susceptible | Susceptible |
| MP622 | Poland | 1.3.4.7.8.10.11 | Resistant | Susceptible | Susceptible |
| MP618 | Poland | 1.2.3.4.6.7.11 | No data | Susceptible | Partially resistant |
| MP650 | Poland | 1.2.3.4.5.7.8.10.11 | Resistant | Resistant | Susceptible |
| EC1 | Ecuador | 2.4.10.11 | Susceptible | Resistant | Susceptible |

Example 7

Methods and Compositions to Avoid Development of Resistance to Novel Genes

Resistance genes in wild populations are usually highly polymorphic (Jones 2001, Dangl and Jones 2001, Bergelson et al, 2001) and this heterogeneity is probably critical for their effectiveness, because they are subject to frequency-dependent selection (if any one R gene predominates, selection is intensified for pathogen races that can overcome it). In agriculture, monocultures are the norm, which facilitates an epidemic of any pathogen that can grow and rapidly reproduce on a particular crop variety. We propose that if enough R genes could be identified and deployed in mixtures, in genetic backgrounds that are otherwise uniform for agronomic and consumer traits, then durable resistance might be achieved in crops (Pink and Puddephat 1999, Jones 2001). For this strategy to work and to address questions related to overcoming R gene based resistance and evolution, it is essential to isolate as many new Rpi genes as possible.

This is achieved according to the present invention by isolating multiple Rpi genes from wild relatives of potato, introducing those genes separately into one variety, and the resulting lines mixed and planted. This strategy circumvents the problem that varietal monocultures become completely susceptible to any race of blight that can overcome the specific Rpi gene in that variety, and the resulting race then dominates the parasite population. Using 3 Rpi genes in a mixture, any blight race that overcomes one of these Rpi genes could only grow on 33% of the plants in the field. An alternate strategy according to this invention comprises using the same variety, but carrying a different Rpi gene, each year. In this scenario, pathogen races that are successful one year are not successful or as successful the next year, resulting in reduced losses. We propose that specifically:

1. Epidemics are slower

If a strain of the *P. infestans* that is virulent on one of the R genes enters the crop then the spread of that strain is limited to the plants which carry that R gene, other plants harbouring different R genes will remain resistant, thus limiting the spread of the pathogen and the overall losses. It is more difficult for the pathogen to develop virulence against multiple R genes and thus the development of strains able to cause disease on more than one R gene will be minimised. As the plants with different R genes will be mixed there will be a spatial separation between plants with the same R gene that will limit the rate of spread within the field.

2. Virulence on More than 1. Rpi Gene Leads to Reduced Fitness Compared with Those that are Virulent on Only 1 Gene Plant R genes function by recognising molecules produced by particular strains of plant pathogens. The currently accepted hypothesis is that a pathogen gains virulence by loss of a gene that encodes an effector molecule that is normally required by the pathogen for overcoming host defence responses and is normally recognised by a plant R gene. Thus to become virulent on more than one R gene involves the loss by the pathogen of more than one effector molecule. Such a strain of the pathogen would be inherently less fit when competing with strains that had lost none or a single effector when growing on hosts that contain different R gene complements.

3. Incompatible Races Trigger Systemic Acquired Resistance

In addition to R gene-mediated resistance responses, plants possess the ability to mount a non-specific defense response known as systemic acquired resistance (SAR). Following the recognition of a pathogen, the plant can initiate defence responses that are active against a wide range of pathogens and is not limited to the pathogen strain that was recognised by the R gene. Thus the recognition of a particular pathogen strain by an introduced R gene will also aid in defence against other strains that may not necessarily be recognised by any introduced R genes.

4. There Will be Weak Selection for Virulence on a Rare Rpi Gene

An Rpi gene that is deployed infrequently within a population will exert less selection pressure on the pathogen to overcome this resistance. Such a strategy could be used to protect valuable R genes and ensure that their longevity is maximised by deploying them in a rational manner so that the pathogen population is not exposed to large amount of crop with the particular R gene. Such rational deployment will be aided by knowledge about the frequency of the corresponding virulence allele within the pathogen population.

REFERENCES

Allouis S, Moore G, Bellec A, Sharp R, Faivre Rampant P, Mortimer K, Pateyron S, Foote T N, Griffiths S, Caboche M, Chalhoub B (2003) Construction and characterisation of a hexaploid wheat (*Triticum aestivum* L.) BAC library from the reference germplasm ‘Chinese Spring’. Cereal Res Commun 31:331-338

Arumuganathan K, Earle E D (1991) Nuclear DNA content of some important plant species. Plant Mol Biol Rep 9:208-218

Balivora A, Ercolano M R, WeiβJ, Meksem K, Bormann C A, Oberhagemann P, Salamini F, Gebhardt C (2002) The R1 gene for potato resistance to late blight (*Phytophthora infestans*) belongs to the leucine zipper/NBS/LRR class of plant resistance genes. Plant J 30:361-371

Black W, Mastenbroek C, Mills W R, Peterson L C (1953) A proposal for an international nomenclature of races of *Phytophthora infestans* and of genes controlling immunity in *Solanum demissum* derivatives. Euphytica 2:173-240

Bouzidi M F, Franchel J, Tao Q, Stormo K, Mraz A, Nicolas P, Mouzeyar S (2006) A sunflower BAC library suitable for PCR screening and physical mapping of targeted genomic regions. Theor Appl Genet. 113:81-89

Bradshaw J E, Bryan G J, Lees A K, McLean K, Solomon-Blackburn R M (2006) Mapping the R10 and R11 genes for resistance to late blight (*Phytophthora infestans*) present in the potato (*Solanum tuberosum*) R-gene differentials of Black. Theor Appl Genet. 112:744-751

Chalhoub B, Belcram H, Caboche M (2004) Efficient cloning of plant genomes into bacterial artificial chromosome (BAC) libraries with larger and more uniform insert size. Plant Biotechnol J 2:181-188

Chang Y-L, Tao Q, Scheuring C, Ding K, Meksem K, Zhang H-B (2001) An integrated map of *Arabidopsis thaliana* for functional analysis of its genome sequence. Genetics 159: 1231-1242

Chen Q, Sun S, Ye Q, McCuine S, Huff E, Zhang H H (2004) Construction of two BAC libraries from the wild Mexican diploid potato *Solanum pinnatisectum*, and the identification of clones near the late blight and Colorado potato beetle resistance loci. Theor Appl Genet. 108:1002-1009

Costanzo S, Simko I, Christ B J, Haynes K G (2005) QTL analysis of late blight resistance in a diploid potato family of *Solanum phureja*×*S. stenotomum*. Theor Appl Genet. 111:609-617

Danesh D, Penuela S, Mudge J, Denny R L, Nordstrom H, Martinez J P, Young N D (1998) A bacterial artificial chromosome library for soybean and identification of clones near a major cyst nematode resistance gene. Theor Appl Genet. 96:196-202

De Wit, P. J. G. M. (1997) Pathogen avirulence and plant resistance: a key role for recognition. *Trends In Plant Science*. 2, 452-458.

El-Kharbotly A, Leonards-Schippers C, Huigen D J, Jacobsen E, Pereira A, Stiekema W J, Salamini F, Gebhardt C (1994) Segregation analysis and RFLP mapping of the R1 and R3 alleles conferring race-specific resistance to *Phytophthora infestans* in progeny of dihaploid potato parents. Mol Gen Genet. 242:749-754

El-Kharbotly A, Palomino-Sanchez C, Salamini F, Jacobsen E, Gebhardt C (1996) R6 and R7 alleles of potato conferring race-specific resistance to *Phytophthora infestans* (Mont.) de Bary identified genetic loci clustering with the R3 locus on chromosome XI. Theor Appl Genet. 92:880-884

Eshed Y, Zamir D (1994) A genomic library of *Lycopersicon pennellii* in *Lycopersicon esculentum*: a tool for fine mapping of genes. Euphytica 79:175-179

Ewing E E, Simko I, Smart C D, Bonierbale M W, Mizubuti E S G, May G D, Fry W E (2000) Genetic mapping from field of qualitative and quantitative resistance to *Phytophthora infestans* in a population derived from *Solanum tuberosum* and *Solanum berthaultii*. Mol Breeding 6:25-36

Feng J, Vick B A, Lee M K, Zhang H B, Jan C C (2006) Construction of BAC and BIBAC libraries from sunflower and identification of linkage group-specific clones by overgo hybridization. Theor Appl Genet. 113:23-32

Flor, H. H. (1971) Current status of the gene-for-gene concept. *Annual Review of Phytopathology* 78, 275-298

Frijters A C J, Zhang Z, van Damme M, Wang G L, Ronald P C, Michelmore R W (1997) Construction of a bacterial artificial chromosome library containing large EcoRI and Hindi) genomic fragments of lettuce. Theor Appl Genet. 94:390-399

Gebhardt, C. and Valkonen, J. P. (2001) Organization of genes controlling disease resistance in the potato genome. *Annu Rev Phytopathol* 39, 79-102

Georgi L L, Wang Y, Yvergniaux D, Ormsbee T, Iñigo M, Reighard G, Abbott A G (2002) Construction of a BAC library and its application to the identification of simple sequence repeats in peach [*Prunus persica* (L.) Batsch]. Theor Appl Genet. 105:1151-1158

Ghislain M, Trognitz B, Herrera MaDeIR, Solis J, Casallo G, Vasquez C, Hurtade O, Castillo R, Portal L, Orrillo M (2001) Genetic loci associated with field resistance to late blight in offspring of *Solanum phureja* and *S. tubersosum* grown under short-day conditions. Theor Appl Genet. 103: 433-442

Grube, R. C., Radwanski, E. R. and Jahn, M. (2000) Comparative genetics of disease resistance within Solanaceae. *Genetics* 155, 873-887

Helgeson J P, Pohlman J D, Austin S, Haberlach G T, Wielgus S M, Ronis D, Zambolim L, Tooley P, McGrath J M, James R V, Stevenson W R (1998) Somatic hybrids between *Solanum bulbocastanum* and potato: a new source of resistance to late blight. Theor Appl Genet. 96:738-742

Hofmann, K., Bucher, P., Falquet, L. and Bairoch, A. (1999) The PROSITE database, its status in 1999. *Nucl. Acids Res.* 27, 215-219.

Huang S, Vleeshouwers V G A A, Werij J S, Hutten R C B, van Eck H J, Visser R G F, Jacobsen E (2004) The R3 resistance to *Phytophthora infestans* in potato is conferred by two closely linked R genes with distinct specificities. Mol Plant Microb Interact 17:428-435

Huang S, van der Vossen E A G, Kuang H, Vleeshouwers VGAA, Zhang N, Borm T J A, van Eck H J, Baker B, Jacobsen E, Visser R G F (2005) Comparative genomics enabled the isolation of the R3a late blight resistance gene in potato. Plant J 42:251-261

Huang, S. (2005) Discovery and characterization of the major late blight resistance complex in potato: genomic structure, functional diversity, and implications. PhD thesis.

Jansky S (2000) Breeding for disease resistance in potato. Plant Breeding Rev 19:69-155

Jiang J, Gill B S, Wang G L, Ronald P C, Ward D C (1995) Metaphase and interphase fluorescence in situ hybridization mapping of the rice genome with bacterial artificial chromosomes. Proc Natl Acad Sci USA 92:4487-4491

Kamoun S, van West P, Vleeshouwers VGAA, de Groot K E, Govers F (1998) Resistance of *Nicotiana benthamiana* to *Phytophthora infestans* is mediated by the recognition of the elicitor protein INF1. Plant Cell 10:1413-1425

Klein P E, Klein R R, Cartinhour S W, Ulanch P E, Dong J, Obert J A, Morishige D T, Schlueter S D, Childs K L, Ale M, Mullet J E (2000) A high-throughput AFLP-based method for constructing integrated genetic and physical maps: progress toward a sorghum genome map. Genome Res 10:789-807

Kuhl J C, Hanneman Jr R E, Havey M J (2001) Characterization and mapping of Rpi1, a late-blight resistance locus from diploid (1 EBN) Mexican *Solanum pinnatisectum*. Mol Genet Genomics 265:977-985

Lanfermeijer F C, Dijkhuis J, Sturre M J G, de Haan P, Hille J (2003) Cloning and characterization of the durable tomato mosaic virus resistance gene $Tm-2^2$ from *Lycopersicon esculentum*. Plant Mol Biol 52:1037-1049

Lanfermeijer, F. C., Warmink, J. and Hille, J. (2005) The products of the broken Tm-2 and the durable Tm-2(2) resistance genes from tomato differ in four amino acids. *J Exp Bot* 56, 2925-2933

Lee H-R, Eom E-M, Urn Y-P, Bang J-W, Lee D-H (2003) Construction of a garlic BAC libaray and chromosomal assignment of BAC clones using the FISH technique. Genome 46:514-520

Leonards-Schippers C, Gieffers W, Salamini F, Gebhardt C (1992) The R1 gene conferring race-specific resistance to *Phytophthora infestans* in potato is located on potato chromosome V. Mol Gen Genet. 233:278-283

Linden, C. C. G. v. d., Wouters, D. D. C. A. E., Mihalka, V. V., Kochieva, E. E. Z., Smulders, M. M. J. M. and Vosman, B. B. (2004) Efficient targeting of plant disease resistance loci using NBS profiling. *Theoretical and applied genetics* 109, 384-393.

Liu Y G and Whittier R F (1994) Rapid preparation of megabase plant DNA from nuclei in agarose plugs and microbeads. Nucleic Acids Res 22:2168-2169

Li X, van Eck H J, Rouppe van der Voort J N A M, Huigen D J, Stam P, Jacobsen E (1998) Autotetraploids and genetic mapping using common AFLP markers: the R2 allele conferring resistance to *Phytophthora infestans* mapped on potato chromosome 4. Theor Appl Genet. 96:1121-1128

Malcolmson J F, Black W (1966) New R genes in *Solanum demissum* Lindl. and their complementary races of *Phytophthora infestans* (Mont.) de Bary. Euphytica 15:199-203

Mastenbroek C (1953) Experiments on the inheritance of blight immunity in potatoes derived from *Solanum demissum* Lindl. Euphytica 2:197-206

McGrath J M, Shaw R S, de los Reyes B G, Weiland J J (2004) Construction of a sugar beet BAC library from a hybrid with diverse traits. Plant Mol Biol Reporter 22:23-28

McHale, L., Tan, X., Koehl, P. and Michelmore, R. W. (2006) Plant NBS-LRR proteins: adaptable guards. *Genome Biol* 7, 212

Meksem K, Zobrist K, Ruben E, Hyten D, Quanzhou T, Zhang H-B, Lightfoot D (2000) Two large-insert soybean genomic libraries constructed in a binary vector: applications in chromosome walking and genome wide physical mapping. Theor Appl Genet. 101:747-755

Michelmore, R. W., Paran, I. and Kesseli, R. V. (1991) Identification of markers linked to disease-resistance genes by bulked segregant analysis: a rapid method to detect markers in specific genomic regions by using segregating populations. *Proc Natl Acad Sci USA* 88, 9828-9832.

Milbourne D, Meyer R C, Collins A J, Ramsay L D, Gebhardt C, Waugh R (1998) Isolation, characterisation and mapping of simple sequence repeat loci in potato. Molecular and General Genetics 259:233-245

Naess S K, Bradeen J M, Wielgus S M, Haberlach G T, McGrath J M, Helgeson J P (2000) Resistance to late blight in *Solanum bulbocastanum* is mapped to chromosome 8. Theor Appl Genet. 101:697-704

Nilmalgoda S D, Cloutier S, Walichnowski A Z (2003) Construction and characterization of a bacterial artificial chromosome (BAC) library of hexaploid wheat (*Triticum aestivum* L.) and validation of genome coverage using locus-specific primers. Genome 46:870-878

Osoegawa, K, Woon P Y, Zhao B, Frengen E, Tateno M, Catanese J J, de Jong P J (1998) An improved approach for construction of bacterial artificial chromosome libraries. Genomics 52:1-8

Ozdemir N, Horn R, Friedt W (2004) Construction and characterization of a BAC library for sunflower (*Helianthus annuus* L.). Euphytica 138:177-183

Pan, Q., Liu, Y.-S., Budai-Hadrian, O., Sela, M., Carmel-Goren, L., Zamir, D. and Fluhr, R. (2001) Comparative Genetics of Nucleotide Binding Site-Leucine Rich Repeat Resistance Gene Homologues in the Genomes of Two Dicotyledons: Tomato and *Arabidopsis. Genetics* 159, 1867c-.

Park T-H, Vleeshouwers V G A A, Hutten R C B, van Eck H J, van der Vossen E, Jacobsen E, Visser R G F (2005a) High-resolution mapping and analysis of the resistance locus Rpi-abpt against *Phytophthora infestans* in potato. Mol Breeding 16:33-43

Park T-H, Gros A, Sikkema A, Vleeshouwers VGAA, Muskens M, Allefs S, Jacobsen E, Visser R G F, van der Vossen E A G (2005b) The late blight resistance locus Rpi-blb3 from *Solanum bulbocastanum* belongs to a major late blight R gene cluster on chromosome 4 of potato. Mol Plant Microb Interact 18:722-729

Park T H, Vleeshouwers V G, Huigen D J, van der Vossen E A, van Eck H J, Visser R G (2005c) Characterization and high-resolution mapping of a late blight resistance locus similar to R2 in potato. Theor Appl Genet. 111:591-597

Rauscher, G. M., Smart, C. D., Simko, I., Bonierbale, M., Mayton, H., Greenland, A. and Fry, W. E. (2006) Characterization and mapping of RPi-ber, a novel potato late blight resistance gene from *Solanum berthaultii. Theoretical and applied genetics* 112, 674-687

Sandbrink J M, Colon L T, Wolters P J C C, Stiekema W J (2000) Two related genotypes of *Solanum microdontum* carry different segregating alleles for field resistance to *Phytophthora infestans*. Molecular Breeding 6:215-225

Śliwka J, Jakuczun H, Lebecka R, Marczewski W, Gebhardt C, Zimnoch-Guzowska E (2006) The novel, major locus Rpi-phu1 for late blight resistance maps to potato chromosome IX and is not correlated with long vegetation period. Theor Appl Genet. 113:685-695

Smilde W D, Brigneti G, Jagger L, Perkins S, Jones J D (2005) *Solanum mochiquense* chromosome IX carries a novel late blight resistance gene Rpi-moc1. Theor Appl Genet. 110:252-258

Song J, Bradeen J M, Naess S K, Raasch J A, Wielgus S M, Haberlach G T, Liu J, Kuang H, Austin-Phillips S, Buell C R, Helgeson J P, Jiang J (2003) Gene R B cloned from *Solanum bulbocastanum* confers broad spectrum resistance to potato late blight. Proc Natl Acad Sci USA 100:9128-9133

Tao Q, Wang A, Zhang H B (2002) One large-insert plant-transformation-competent BIBAC library and three BAC libraries of Japonica rice for genome research in rice and other grasses. Theor Appl Genet. 105:1058-1066

Thomas C M, Vos P, Zabeau M, Jones D A, Norcott K A, Chadwick B P, Jones J D (1995) Identification of amplified restriction fragment polymorphism (AFLP) markers tightly linked to the tomato Cf-9 gene for resistance to *Cladosporium fulvum*. Plant J 8:785-794 van der Vossen E, Sikkema A, Hekkert B L, Gros J, Stevens P, Muskens M, Wouters D, Pereira A, Stiekema W, Allefs S (2003) An ancient R gene from the wild potato species *Solanum bulbocastanum* confers broad-spectrum resistance to *Phytophthora infestans* in cultivated potato and tomato. Plant J 36:867-882 van der Vossen E A G, Gros J, Sikkema A, Muskens M, Wouters D, Wolters P, Pereira A, Allefs S (2005) The Rpi-blb2 gene from *Solanum bulbocastanum* is an Mi-1 gene homolog conferring broad-spectrum late blight resistance in potato. Plant J 44:208-222

Vilarinhos A D, Piffanelli P, Lagoda P, Thibivilliers S, Sabau X, Carreel F, Hont A D (2003) Construction and characterization of a bacterial artificial chromosome library of banana (*Musa acuminate* Colla). Theor Appl Genet. 106:1102-1106

Vleeshouwers VGAA, van Dooijeweert W, Keizer L C P, Sijpkes L, Govers F, Colon L T (1999) A laboratory assay for *Phytophthora infestans* resistance in various *Solanum* species reflects the field situation. European Journal of Plant Pathology 105:241-250

Vos P, Hogers R, Bleeker M, Reijans M, Vandelee T, Homes M, Frijters A, Pot J, Peleman J, Kuiper M, Zabeau M (1995) AFLP: A new technique for DNA fingerprinting. Nucleic Acids Research 23:4407-4414

Wang G L, Holsten T E, Song W Y, Wang H P, Ronald P C (1995) Construction of a rice bacterial artificial chromosome library and identification of clones linked to the Xa-21 disease resistance locus. Plant J 7:525-533

Wastie R L (1991) Breeding for resistance. In: Ingram D S, William P H (eds) Advances in plant pathology Vol. 7. Academic press, London, pp 193-224

Woo S-S, Jiang J, Gill B S, Paterson A H, Wing R A (1994) Construction and charaterization of a bacterial artificial chromosome library of *Sorghum bicolor*. Nucleic Acids Res 22:4922-4931

Wu C C, Nimmakayala P, Santos F A, Springman R, Scheuring C, Meksem K, Lightfoot D A, Zhang H-B (2004) Construction and characterization of a soybean bacterial artificial chromosome library and use of multiple complementary libraries for genome physical mapping. Theor Appl Genet. 109:1041-1050

Yüksel B, Paterson A H (2005) Construction and characterization of a peanut HindIII BAC library. Theor Appl Genet. 111:630-639

The invention claimed is:

1. An isolated Rpi resistance gene having a sequence which is at least 94% homologous to the nucleic acid sequence of SEQ ID NO: 1, wherein the gene encodes a protein which is capable of mediating a response against *Phytophthora infestans*.

2. The isolated Rpi resistance gene as claimed in claim 1 having a sequence which is at least 95% homologous to the nucleic acid sequence of SEQ ID NO: 1.

3. The isolated Rpi resistance gene as claimed in claim 2 which comprises the nucleic acid sequence of SEQ ID NO: 1 or 7.

4. The isolated Rpi resistance gene as claimed in claim 3 which comprises the nucleic acid sequence of SEQ ID NO: 8.

5. An isolated gene encoding a protein having an amino acid sequence which is at least 94% homologous to the amino acid sequence of SEQ ID NO: 4 and which is capable of mediating a response against *Phytophthora infestans*.

6. A plant transformed with an isolated gene selected from the group consisting of: (i) a gene having a sequence which is at least 94% homologous to the nucleic acid sequence of SEQ ID NO: 1, wherein the gene encodes a protein which is capable of mediating a response against *Phytophthora infestans*; and (ii) a gene encoding a protein having an amino acid sequence which is at least 94% homologous to the amino acid sequence of SEQ ID NO: 4, and which is capable of mediating a response against *Phytophthora infestans*.

7. The plant according to claim 6 which is a potato.

8. A progeny of the plant according to claim 7, wherein the progeny comprises the gene.

9. A method of making a transgenic plant having enhanced late blight resistance which comprises introducing into a cell of said plant or into a portion of said plant, the gene according to claim 1 and generating a whole plant from said cell or from said portion of said plant.

10. A composition comprising the gene according to claim 1 and appropriate regulatory sequences operatively linked to said gene to achieve expression thereof when placed into an appropriate in vitro or in vivo system.

11. A method for providing durable disease resistance in potato which comprises isolating multiple Rpi genes from relatives of potato, introducing said genes into a commercial line or variety of potato, and mixing and planting the resulting mixture of lines thus produced; wherein the Rpi genes comprise the gene of claim 1.

12. A method for providing durable disease resistance in potato which comprises isolating multiple Rpi genes from wild relatives of potato, introducing said genes separately into a commercial line or variety of potato, and each year, planting a variety carrying a different Rpi gene; wherein the Rpi genes comprise the gene of claim 1.

* * * * *

UNITED STATES PATENT AND TRADEMARK OFFICE
CERTIFICATE OF CORRECTION

PATENT NO. : 8,367,893 B2
APPLICATION NO. : 12/669871
DATED : February 5, 2013
INVENTOR(S) : Jonathan Jones et al.

Page 1 of 1

It is certified that error appears in the above-identified patent and that said Letters Patent is hereby corrected as shown below:

On the title page under item (73), add the following Assignee:

Wageningen University
P.O. Box 386
Wageningen, Netherlands 6700 AJ

Signed and Sealed this
Twenty-ninth Day of October, 2013

Teresa Stanek Rea
*Deputy Director of the United States Patent and Trademark Office*

SEQUENCE LISTING

<160> NUMBER OF SEQ ID NOS: 116

<210> SEQ ID NO 1
<211> LENGTH: 2676
<212> TYPE: DNA
<213> ORGANISM: Solanum okadae

<400> SEQUENCE: 1

| | | | | | |
|---|---|---|---|---|---|
| atgaattatt | gtgtttacaa | gacttgggcc | gttgactctt | actttcccct | cctcatcctc | 60 |
| acatttagaa | aaagaaatt | taacgaaaaa | ttaaaggaga | tggctgaaat | tcttctcaca | 120 |
| gcagtcatca | ataaatcaat | agaaatagct | ggaaatgtac | tctttcaaga | aggtacgcgt | 180 |
| ttatattggt | tgaaagagga | catcgattgg | ctccagagag | aaatgagaca | cattcgatca | 240 |
| tatgtagaca | atgcaaaggc | aaaggaagtt | ggaggcgatt | caagggtgaa | aaacttatta | 300 |
| aaagatattc | aacaactggc | aggtgatgtg | gaggatctat | tagatgagtt | tcttccaaaa | 360 |
| attcaacaat | ccataagtt | catttgttgc | cttaagacgg | tttcttttgc | cgatgagttt | 420 |
| gctatggaga | ttgagaagat | aaaaagaaga | gttgctgata | ttgaccgtgt | aaggacaact | 480 |
| tacagcatca | cagatacaag | taacaataat | gatgattgca | ttccattgga | ccggagaaga | 540 |
| ttgttccttc | atgctgatga | acagaggtc | atcggtctgg | aagatgactt | caatacacta | 600 |
| caagccaaat | tacttgatca | tgatttgcct | tatggagttg | tttcaatagt | tggcatgccc | 660 |
| ggtttgggaa | aaacaactct | tgccaagaaa | ctttataggc | atgtctgtca | tcaatttgag | 720 |
| tgttcgggac | tggtctatgt | ttcacaacag | ccaagggcgg | gagaaatctt | acatgacata | 780 |
| gccaaacaag | ttggactgac | ggaagaggaa | aggaaagaaa | acttggagaa | caacctacga | 840 |
| tcactcttga | aaataaaaag | gtatgttatt | ctcttagatg | acatttggga | tgttgaaatt | 900 |
| tgggatgatc | taaaacttgt | ccttcctgaa | tgtgattcaa | aaattggcag | taggataatt | 960 |
| ataacctctc | gaaatagtaa | tgtaggcaga | tacataggag | gggatttctc | aatccacgtg | 1020 |
| ttgcaacccc | tagattcaga | gaaaagcttt | gaactcttta | ccaagaaaat | ctttaatttt | 1080 |
| gttaatgata | attgggccaa | tgcttccacca | gacttggtaa | atattggtag | atgtatagtt | 1140 |
| gagagatgtg | gaggtatacc | gctagcaatt | gtggtgactg | caggcatgtt | aagggcaaga | 1200 |
| ggaagaacag | aacatgcatg | gaacagagta | cttgagagta | tggctcataa | aattcaagat | 1260 |
| ggatgtggta | aggtattggc | tctgagttac | aatgatttgc | ccattgcatt | aaggccatgt | 1320 |
| ttcttgtact | ttggtctta | ccccgaggac | catgaaattc | gtgcttttga | tttgacaaat | 1380 |
| atgtggattg | ctgagaagct | gatagttgta | aatactggca | atgggcgaga | ggctgaaagt | 1440 |
| ttggcggatg | atgtcctaaa | tgatttggtt | tcaagaaact | tgattcaagt | tgccaaaagg | 1500 |
| acatatgatg | aagaatttc | aagttgtcgc | atacatgact | tgttacatag | tttgtgtgtg | 1560 |
| gacttggcta | aggaaagtaa | cttctttcac | acggagcaca | atgcatttgg | tgatcctagc | 1620 |
| aatgttgcta | gggtgcgaag | gattacattc | tactctgatg | ataatgccat | gaatgagttc | 1680 |
| ttccatttaa | atcctaagcc | tatgaagctt | cgttcacttt | tctgtttcac | aaaagaccgt | 1740 |
| tgcatatttt | ctcaaatggc | tcatcttaac | ttcaaattat | tgcaagtgtt | ggttgtagtc | 1800 |
| atgtctcaaa | agggttatca | gcatgttact | ttccccaaaa | aaattgggaa | catgagttgc | 1860 |
| ctacgttatg | tgcgattgga | ggggcaatt | agagtaaaat | tgccaaatag | tattgtcaag | 1920 |
| ctcaaatgtc | tagagaccct | ggatatattt | catagctcta | gtaaacttcc | ttttggtgtt | 1980 |
| tgggagtcta | aaatattgag | acatctttgt | tacacagaag | aatgttactg | tgtctctttt | 2040 |

-continued

```
gcaagtccat tttgccgaat catgcctcct aataatctac aaactttgat gtgggtggat    2100
gataaatttt gtgaaccaag attgttgcac cgattgataa atttaagaac attgtgtata    2160
atggatgtat ccggttctac cattaagata ttatcagcat tgagccctgt gcctagagcg    2220
ttggaggttc tgaagctcag atttttcaag aacacgagtg agcaaataaa cttgtcgtcc    2280
catccaaata ttgtcgagtt gggtttggtt ggtttctcag caatgctctt gaacattgaa    2340
gcattccctc caaatcttgt caagcttaat cttgtcggct tgatggtaga cggtcatcta    2400
ttggcagtgc ttaagaaatt gcccaaatta aggatactta tattgctttg gtgcagacat    2460
gatgcagaaa aaatggatct ctctggtgat agctttccgc aacttgaagt tttgtatatt    2520
gaggatgcac aagggttgtc tgaagtaacg tgcatggatg atatgagtat gcctaaattg    2580
aaaaagctat ttcttgtaca aggcccaaac atttccccaa ttagtctcag ggtctcggaa    2640
cggcttgcaa agttgagaat atcacaggta ctataa                             2676
```

<210> SEQ ID NO 2
<211> LENGTH: 2589
<212> TYPE: DNA
<213> ORGANISM: Solanum mochiquense

<400> SEQUENCE: 2

```
atggctgaaa ttcttcttac agcagtcatc aataaatctg tagaaatagc tggaaatgta      60
ctctttcaag aaggtacgcg tttatattgg ttgaaggagg atatagattg gctccaaaga     120
gaaatgagac acattcgatc atatgtagac aatgcaaagg ccaaggaagt tggaggtgat     180
tcaagggtga aaaacttatt aaaagatatt caacaactcg caggtgatgt ggaggatctc     240
ctagatgagt ttcttccaaa aattcaacaa tccagtaagt tcaaaggcgc aatttgttgc     300
cttaagaccg tttcttttgc ggatgagttt gctatggaga ttgagaagat aaaaagaagg     360
gttgtggaca ttgatcgtgt aaggacaact tacaacatca tggatacaaa taacaacaat     420
gattgcattc cattggacca gagaagattg ttccttcatg ttgatgaaac agaggtcatc     480
ggtttggatg atgacttcaa tacactacaa gccaaattac ttgaccaaga tttgccttat     540
ggagttgttt caatagttgg catgcccggt ctaggaaaaa caactcttgc caagaaactt     600
tataggcatg tccgtcataa atttgagtgt tcgggactgg tctatgtttc acaacagcca     660
agggcgggag aaatcttaat cgacatagcc aaacaagttg gactgacgga agacgaaagg     720
aaagaaaact tggagaacaa cctacggtca ctcttgaaaa gaaaaaggta tgttattctc     780
ttagatgaca tttgggatgt tgaaatttgg gatgatctaa aacttgtcct tcctgaatgt     840
gattcaaaaa ttggcagtag gataattata acctctcgaa atagtaatgt aggcagatac     900
ataggagggg atttctcaat tcacgtgttg caacctctaa attcggagaa cagttttgaa     960
ctctttacca gaaaatcttt tatttttgat aacaataata attggaccaa tgcttcacca    1020
aacttggtag atattggtag aagtatagtt ggtagatgtg tggtatacc  actagccatt    1080 gtggtgactg caggcatgtt aagggcaaga gaaagaacag aacgtgcatg gaacaggtta    1140
cttgagagta tgagccataa agttcaagat ggatgtgcta aggtattggc tctgagttac    1200
aatgatttgc caattgcatt aaggccatgt ttcttgtatt ttggcctttta ccccgaggat    1260 catgaaattc gtgcttttga tttgacaaat atgtggattg ctgagaagtt gatagttgta    1320
aatagtggca atgggcgaga ggctgaaagt ttggcggatg atgtcctaaa tgatttggtt    1380
tcaagaaaca tgattcaagt tgccaaaagg acatatgatg aagaatttc  aagttgtcgc    1440 atacatgact tgttacatag tttgtgtgtt gacttggcta aggaaagcaa cttctttcac    1500
```

-continued

```
accgagcaca atgcattggg tgatcccgga aatgttgcta ggctgcgaag gattacattc    1560
tactctgata taatgccat gaatgagttc ttccgttcaa atcctaagct tgagaagctt    1620
cgtgcacttt tctgttttac agaagaccct tgcatatttt ctcaactggc tcatcttgat    1680
ttcaaattat tgcaagtgtt ggttgtagtc atctttgttg atgatatttg tggtgtcagt    1740
atcccaaaca catttgggaa catgaggtgc ttacgttatc tgcgattcca ggggcatttt    1800
tatgggaaac tgccaaattg tatggtgaag ctcaaacgtc tagagaccct cgatattggt    1860
tatagcttaa ttaaatttcc tactggtgtt tggaagtcta cacaattgaa acatcttcgt    1920
tatggaggtt ttaatcaagc atctaacagt tgcttttcta taagcccatt tttcccaaac    1980
ttgtactcat tgcctcataa taatgtacaa actttgatgt ggctggatga taaattttt    2040 gaggcgggat tgttgcaccg attgatcaat ttaagaaaac tgggtatagc aggagtatct    2100
gattctacag ttaagatatt atcagcattg agccctgtgc aacggcgct ggaggttctg    2160 aagctcaaaa tttacaggga catgagtgag caaataaact tgtcgtccta tccaaatatt    2220
gttaagttgc gtttgaatgt ttgcggaaga atgcgcttga actgtgaagc atttcctcca    2280
aatcttgtca agcttactct tgtcggcgat gaggtagacg gtcatgtagt ggcagagctt    2340
aagaaattgc ccaaattaag gatacttaaa atgtttgggt gcagtcataa tgaagaaaag    2400
atggatctct ctggtgatgg tgatagcttt ccgcaacttg aagttctgca tattgatgaa    2460
ccagatgggt tgtctgaagt aacgtgtagg gatgatgtca gtatgcctaa attgaaaaag    2520
ttgttacttg tacaacgccg ccccttctcca attagtctct cagaacgtct tgcaagctc    2580 agaatatga                                                            2589
```

<210> SEQ ID NO 3
<211> LENGTH: 2718
<212> TYPE: DNA
<213> ORGANISM: Solanum neorossii

<400> SEQUENCE: 3

```
atgaattatt tgtttacaa gacttgggcc gttgactcta acactaaagc aaatagtaca      60
tctttcttat ccttttctc ttactttccc ttcctcatcc tcacatttag aaaaaagaaa     120
tttaacgaaa aattaaagga gatggctgaa attcttctca cagcagtcat caataaatca     180
atagaaatag ctggaaatgt actctttcaa gaaggtacgc gtttatattg gttgaaagag     240
gacatcgatt ggctccagag agaaatgaga cacattcgat catatgtaga caatgcaaag     300 gcaaggaag ttggaggcga ttcaagggtg aaaaacttat aaaagatat caacaactg     360 gcaggtgatg tggaggatct attagatgag tttcttccaa aaattcaaca atccaataag     420
ttcatttgtt gccttaagac ggtttctttt gccgatgagt ttgctatgga gattgagaag     480
ataaaaagaa gagttgctga tattgaccgt gtaaggacaa cttacagcat cacagataca     540
agtaacaata atgatgattg cattccattg gaccggagaa gattgttcct tcatgctgat     600
gaaacagagg tcatcggtct ggaagatgac ttcaatacac tacaagccaa attacttgat     660
catgatttgc cttatggagt tgtttcaata gttggcatgc ccggtttggg aaaaacaact     720
cttgccaaga aactttatag gcatgtctgt catcaatttg agtgttcggg actggtctat     780
gtttcacaac agccaaggc gggagaaatc ttacatgaca tagccaaaca agttggactg     840
acggaagagg aaaggaaaga aaacttggag aacaacctac gatcactctt gaaaataaaa     900
aggtatgtta ttctcttaga tgacatttgg gatgttgaaa tttgggatga tctaaaactt     960
gtccttcctg aatgtgattc aaaaattggc agtaggataa ttataacctc tcgaaatagt    1020
```

-continued

```
aatgtaggca gatacatagg aggggatttc tcaatccacg tgttgcaacc cctagattca    1080
gagaaaagct ttgaactctt taccaagaaa atctttaatt ttgttaatga taattgggcc    1140
aatgcttcac cagacttggt aaatattggt agatgtatag ttgagagatg tggaggtata    1200
ccgctagcaa ttgtggtgac tgcaggcatg ttaaggcaa gaggaagaac agaacatgca     1260
tggaacagag tacttgagag tatggctcat aaaattcaag atggatgtgg taaggtattg    1320
gctctgagtt acaatgattt gcccattgca ttaaggccat gtttcttgta ctttggtctt    1380
taccccgagg accatgaaat tcgtgctttt gatttgacaa atatgtggat tgctgagaag    1440
ctgatagttg taaatactgg caatgggcga gaggctgaaa gtttggcgga tgatgtccta    1500
aatgatttgg tttcaagaaa cttgattcaa gttgccaaaa ggacatatga tggaagaatt    1560
tcaagttgtc gcatacatga cttgttacat agtttgtgtg tggacttggc taaggaaagt    1620
aacttctttc acacggagca ctatgcattt ggtgatccta gcaatgttgc tagggtgcga    1680
aggattacat tctactctga tgataatgcc atgaatgagt tcttccattt aaatcctaag    1740
cctatgaagc ttcgttcact tttctgtttc acaaaagacc gttgcatatt ttctcaaatg    1800
gctcatctta acttcaaatt attgcaagtg ttggttgtag tcatgtctca aagggttat    1860 cagcatgtta ctttccccaa aaaaattggg aacatgagtt gcctacgcta tgtgcgattg    1920
gagggggcaa ttagagtaaa attgccaaat agtattgtca agctcaaatg tctagagacc    1980
ctggatatat ttcatagctc tagtaaactt ccttttggtg tttgggagtc taaaatattg    2040
agacatcttt gttacacaga agaatgttac tgtgtctctt ttgcaagtcc attttgccga    2100
atcatgcctc ctaataatct acaaactttg atgtgggtgg atgataaatt ttgtgaacca    2160
agattgttgc accgattgat aaatttaaga acattgtgta aatgatgt atccggttct     2220 accattaaga tattatcagc attgagcct gtgcctaaag cgttggaggt tctgaagctc     2280
agatttttca gaacacgag tgagcaaata aacttgtcgt cccatccaaa tattgtcgag     2340 ttgggttttgg ttggtttctc agcaatgctc ttgaacattg aagcattccc tccaaatctt   2400
gtcaagctta atcttgtcgg cttgatggta gacggtcatc tattggcagt gcttaagaaa    2460
ttgcccaaat taaggatact tatattgctt tggtgcagac atgatgcaga aaaatggat    2520 ctctctggtg atagctttcc gcaacttgaa gttttgtata ttgaggatgc acaagggttg    2580
tctgaagtaa cgtgcatgga tgatatgagt atgcctaaat tgaaaaagct attctcttgta   2640 caaggcccaa acatttcccc aattagtctc agggtctcgg aacggcttgc aaagttgaga    2700
atatcacagg tactataa                                                  2718
```

<210> SEQ ID NO 4
<211> LENGTH: 891
<212> TYPE: PRT
<213> ORGANISM: Solanum okadae

<400> SEQUENCE: 4

Met Asn Tyr Cys Val Tyr Lys Thr Trp Ala Val Asp Ser Tyr Phe Pro
1               5                   10                  15

Phe Leu Ile Leu Thr Phe Arg Lys Lys Lys Phe Asn Glu Lys Leu Lys
            20                  25                  30

Glu Met Ala Glu Ile Leu Leu Thr Ala Val Ile Asn Lys Ser Ile Glu
        35                  40                  45

Ile Ala Gly Asn Val Leu Phe Gln Glu Gly Thr Arg Leu Tyr Trp Leu
    50                  55                  60

Lys Glu Asp Ile Asp Trp Leu Gln Arg Glu Met Arg His Ile Arg Ser
65                  70                  75                  80

```
Tyr Val Asp Asn Ala Lys Ala Lys Glu Val Gly Gly Asp Ser Arg Val
                 85                  90                  95

Lys Asn Leu Leu Lys Asp Ile Gln Gln Leu Ala Gly Asp Val Glu Asp
            100                 105                 110

Leu Leu Asp Glu Phe Leu Pro Lys Ile Gln Gln Ser Asn Lys Phe Ile
            115                 120                 125

Cys Cys Leu Lys Thr Val Ser Phe Ala Asp Glu Phe Ala Met Glu Ile
        130                 135                 140

Glu Lys Ile Lys Arg Arg Val Ala Asp Ile Asp Arg Val Arg Thr Thr
145                 150                 155                 160

Tyr Ser Ile Thr Asp Thr Ser Asn Asn Asn Asp Cys Ile Pro Leu
                165                 170                 175

Asp Arg Arg Arg Leu Phe Leu His Ala Asp Glu Thr Glu Val Ile Gly
                180                 185                 190

Leu Glu Asp Asp Phe Asn Thr Leu Gln Ala Lys Leu Leu Asp His Asp
            195                 200                 205

Leu Pro Tyr Gly Val Val Ser Ile Val Gly Met Pro Gly Leu Gly Lys
            210                 215                 220

Thr Thr Leu Ala Lys Lys Leu Tyr Arg His Val Cys His Gln Phe Glu
225                 230                 235                 240

Cys Ser Gly Leu Val Tyr Val Ser Gln Gln Pro Arg Ala Gly Glu Ile
                245                 250                 255

Leu His Asp Ile Ala Lys Gln Val Gly Leu Thr Glu Glu Arg Lys
            260                 265                 270

Glu Asn Leu Glu Asn Asn Leu Arg Ser Leu Leu Lys Ile Lys Arg Tyr
            275                 280                 285

Val Ile Leu Leu Asp Asp Ile Trp Asp Val Glu Ile Trp Asp Leu
            290                 295                 300

Lys Leu Val Leu Pro Glu Cys Asp Ser Lys Ile Gly Ser Arg Ile Ile
305                 310                 315                 320

Ile Thr Ser Arg Asn Ser Asn Val Gly Arg Tyr Ile Gly Gly Asp Phe
                325                 330                 335

Ser Ile His Val Leu Gln Pro Leu Asp Ser Glu Lys Ser Phe Glu Leu
            340                 345                 350

Phe Thr Lys Lys Ile Phe Asn Phe Val Asn Asp Asn Trp Ala Asn Ala
        355                 360                 365

Ser Pro Asp Leu Val Asn Ile Gly Arg Cys Ile Val Glu Arg Cys Gly
    370                 375                 380

Gly Ile Pro Leu Ala Ile Val Val Thr Ala Gly Met Leu Arg Ala Arg
385                 390                 395                 400

Gly Arg Thr Glu His Ala Trp Asn Arg Val Leu Glu Ser Met Ala His
                405                 410                 415

Lys Ile Gln Asp Gly Cys Gly Lys Val Leu Ala Leu Ser Tyr Asn Asp
            420                 425                 430

Leu Pro Ile Ala Leu Arg Pro Cys Phe Leu Tyr Phe Gly Leu Tyr Pro
        435                 440                 445

Glu Asp His Glu Ile Arg Ala Phe Asp Leu Thr Asn Met Trp Ile Ala
    450                 455                 460

Glu Lys Leu Ile Val Val Asn Thr Gly Asn Gly Arg Glu Ala Glu Ser
465                 470                 475                 480

Leu Ala Asp Asp Val Leu Asn Asp Leu Val Ser Arg Asn Leu Ile Gln
                485                 490                 495

Val Ala Lys Arg Thr Tyr Asp Gly Arg Ile Ser Ser Cys Arg Ile His
```

```
                    500             505              510
Asp Leu Leu His Ser Leu Cys Val Asp Leu Ala Lys Glu Ser Asn Phe
            515                 520                 525
Phe His Thr Glu His Asn Ala Phe Gly Asp Pro Ser Asn Val Ala Arg
        530                 535                 540
Val Arg Arg Ile Thr Phe Tyr Ser Asp Asp Asn Ala Met Asn Glu Phe
545                 550                 555                 560
Phe His Leu Asn Pro Lys Pro Met Lys Leu Arg Ser Leu Phe Cys Phe
                565                 570                 575
Thr Lys Asp Arg Cys Ile Phe Ser Gln Met Ala His Leu Asn Phe Lys
            580                 585                 590
Leu Leu Gln Val Leu Val Val Met Ser Gln Lys Gly Tyr Gln His
        595                 600                 605
Val Thr Phe Pro Lys Lys Ile Gly Asn Met Ser Cys Leu Arg Tyr Val
        610                 615                 620
Arg Leu Glu Gly Ala Ile Arg Val Lys Leu Pro Asn Ser Ile Val Lys
625                 630                 635                 640
Leu Lys Cys Leu Glu Thr Leu Asp Ile Phe His Ser Ser Ser Lys Leu
                645                 650                 655
Pro Phe Gly Val Trp Glu Ser Lys Ile Leu Arg His Leu Cys Tyr Thr
            660                 665                 670
Glu Glu Cys Tyr Cys Val Ser Phe Ala Ser Pro Phe Cys Arg Ile Met
            675                 680                 685
Pro Pro Asn Asn Leu Gln Thr Leu Met Trp Val Asp Asp Lys Phe Cys
        690                 695                 700
Glu Pro Arg Leu Leu His Arg Leu Ile Asn Leu Arg Thr Leu Cys Ile
705                 710                 715                 720
Met Asp Val Ser Gly Ser Thr Ile Lys Ile Leu Ser Ala Leu Ser Pro
                725                 730                 735
Val Pro Arg Ala Leu Glu Val Leu Lys Leu Arg Phe Phe Lys Asn Thr
            740                 745                 750
Ser Glu Gln Ile Asn Leu Ser Ser His Pro Asn Ile Val Glu Leu Gly
        755                 760                 765
Leu Val Gly Phe Ser Ala Met Leu Leu Asn Ile Glu Ala Phe Pro Pro
    770                 775                 780
Asn Leu Val Lys Leu Asn Leu Val Gly Leu Met Val Asp Gly His Leu
785                 790                 795                 800
Leu Ala Val Leu Lys Lys Leu Pro Lys Leu Arg Ile Leu Ile Leu Leu
                805                 810                 815
Trp Cys Arg His Asp Ala Glu Lys Met Asp Leu Ser Gly Asp Ser Phe
            820                 825                 830
Pro Gln Leu Glu Val Leu Tyr Ile Glu Asp Ala Gln Gly Leu Ser Glu
        835                 840                 845
Val Thr Cys Met Asp Asp Met Ser Met Pro Lys Leu Lys Leu Phe
        850                 855                 860
Leu Val Gln Gly Pro Asn Ile Ser Pro Ile Ser Leu Arg Val Ser Glu
865                 870                 875                 880
Arg Leu Ala Lys Leu Arg Ile Ser Gln Val Leu
                885                 890

<210> SEQ ID NO 5
<211> LENGTH: 862
<212> TYPE: PRT
<213> ORGANISM: Solanum mochiquense
```

```
<400> SEQUENCE: 5

Met Ala Glu Ile Leu Leu Thr Ala Val Ile Asn Lys Ser Val Glu Ile
1               5                   10                  15

Ala Gly Asn Val Leu Phe Gln Glu Gly Thr Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Val Gly Gly Asp Ser Arg Val Lys
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Ser Lys Phe Lys Gly
                85                  90                  95

Ala Ile Cys Cys Leu Lys Thr Val Ser Phe Ala Asp Glu Phe Ala Met
            100                 105                 110

Glu Ile Glu Lys Ile Lys Arg Arg Val Val Asp Ile Asp Arg Val Arg
            115                 120                 125

Thr Thr Tyr Asn Ile Met Asp Thr Asn Asn Asn Asp Cys Ile Pro
130                 135                 140

Leu Asp Gln Arg Arg Leu Phe Leu His Val Asp Glu Thr Glu Val Ile
145                 150                 155                 160

Gly Leu Asp Asp Asp Phe Asn Thr Leu Gln Ala Lys Leu Leu Asp Gln
                165                 170                 175

Asp Leu Pro Tyr Gly Val Val Ser Ile Val Gly Met Pro Gly Leu Gly
            180                 185                 190

Lys Thr Thr Leu Ala Lys Lys Leu Tyr Arg His Val Arg His Lys Phe
            195                 200                 205

Glu Cys Ser Gly Leu Val Tyr Val Ser Gln Gln Pro Arg Ala Gly Glu
210                 215                 220

Ile Leu Ile Asp Ile Ala Lys Gln Val Gly Leu Thr Glu Asp Glu Arg
225                 230                 235                 240

Lys Glu Asn Leu Glu Asn Asn Leu Arg Ser Leu Leu Lys Arg Lys Arg
                245                 250                 255

Tyr Val Ile Leu Leu Asp Asp Ile Trp Asp Val Glu Ile Trp Asp Asp
            260                 265                 270

Leu Lys Leu Val Leu Pro Glu Cys Asp Ser Lys Ile Gly Ser Arg Ile
            275                 280                 285

Ile Ile Thr Ser Arg Asn Ser Asn Val Gly Arg Tyr Ile Gly Gly Asp
290                 295                 300

Phe Ser Ile His Val Leu Gln Pro Leu Asn Ser Glu Asn Ser Phe Glu
305                 310                 315                 320

Leu Phe Thr Lys Lys Ile Phe Ile Phe Asp Asn Asn Asn Trp Thr
                325                 330                 335

Asn Ala Ser Pro Asn Leu Val Asp Ile Gly Arg Ser Ile Val Gly Arg
            340                 345                 350

Cys Gly Gly Ile Pro Leu Ala Ile Val Val Thr Ala Gly Met Leu Arg
            355                 360                 365

Ala Arg Glu Arg Thr Glu Arg Ala Trp Asn Arg Leu Leu Glu Ser Met
            370                 375                 380

Ser His Lys Val Gln Asp Gly Cys Ala Lys Val Leu Ala Leu Ser Tyr
385                 390                 395                 400

Asn Asp Leu Pro Ile Ala Leu Arg Pro Cys Phe Leu Tyr Phe Gly Leu
                405                 410                 415
```

-continued

```
Tyr Pro Glu Asp His Glu Ile Arg Ala Phe Asp Leu Thr Asn Met Trp
            420                 425                 430

Ile Ala Glu Lys Leu Ile Val Val Asn Ser Gly Asn Gly Arg Glu Ala
            435                 440                 445

Glu Ser Leu Ala Asp Asp Val Leu Asn Asp Leu Val Ser Arg Asn Met
            450                 455                 460

Ile Gln Val Ala Lys Arg Thr Tyr Asp Gly Arg Ile Ser Ser Cys Arg
465                 470                 475                 480

Ile His Asp Leu Leu His Ser Leu Cys Val Asp Leu Ala Lys Glu Ser
                    485                 490                 495

Asn Phe Phe His Thr Glu His Asn Ala Leu Gly Asp Pro Gly Asn Val
                500                 505                 510

Ala Arg Leu Arg Arg Ile Thr Phe Tyr Ser Asp Asn Asn Ala Met Asn
            515                 520                 525

Glu Phe Phe Arg Ser Asn Pro Lys Leu Glu Lys Leu Arg Ala Leu Phe
            530                 535                 540

Cys Phe Thr Glu Asp Pro Cys Ile Phe Ser Gln Leu Ala His Leu Asp
545                 550                 555                 560

Phe Lys Leu Leu Gln Val Leu Val Val Ile Phe Val Asp Asp Ile
                    565                 570                 575

Cys Gly Val Ser Ile Pro Asn Thr Phe Gly Asn Met Arg Cys Leu Arg
                580                 585                 590

Tyr Leu Arg Phe Gln Gly His Phe Tyr Gly Lys Leu Pro Asn Cys Met
            595                 600                 605

Val Lys Leu Lys Arg Leu Glu Thr Leu Asp Ile Gly Tyr Ser Leu Ile
610                 615                 620

Lys Phe Pro Thr Gly Val Trp Lys Ser Thr Gln Leu Lys His Leu Arg
625                 630                 635                 640

Tyr Gly Gly Phe Asn Gln Ala Ser Asn Ser Cys Phe Ser Ile Ser Pro
                    645                 650                 655

Phe Phe Pro Asn Leu Tyr Ser Leu Pro His Asn Asn Val Gln Thr Leu
                660                 665                 670

Met Trp Leu Asp Asp Lys Phe Phe Glu Ala Gly Leu Leu His Arg Leu
            675                 680                 685

Ile Asn Leu Arg Lys Leu Gly Ile Ala Gly Val Ser Asp Ser Thr Val
            690                 695                 700

Lys Ile Leu Ser Ala Leu Ser Pro Val Pro Thr Ala Leu Glu Val Leu
705                 710                 715                 720

Lys Leu Lys Ile Tyr Arg Asp Met Ser Glu Gln Ile Asn Leu Ser Ser
                    725                 730                 735

Tyr Pro Asn Ile Val Lys Leu Arg Leu Asn Val Cys Gly Arg Met Arg
                740                 745                 750

Leu Asn Cys Glu Ala Phe Pro Pro Asn Leu Val Lys Leu Thr Leu Val
            755                 760                 765

Gly Asp Glu Val Asp Gly His Val Val Ala Glu Leu Lys Lys Leu Pro
            770                 775                 780

Lys Leu Arg Ile Leu Lys Met Phe Gly Cys Ser His Asn Glu Glu Lys
785                 790                 795                 800

Met Asp Leu Ser Gly Asp Gly Asp Ser Phe Pro Gln Leu Glu Val Leu
                    805                 810                 815

His Ile Asp Glu Pro Asp Gly Leu Ser Glu Val Thr Cys Arg Asp Asp
                820                 825                 830

Val Ser Met Pro Lys Leu Lys Lys Leu Leu Leu Val Gln Arg Arg Pro
            835                 840                 845
```

-continued

Ser Pro Ile Ser Leu Ser Glu Arg Leu Ala Lys Leu Arg Ile
    850                 855                 860

<210> SEQ ID NO 6
<211> LENGTH: 905
<212> TYPE: PRT
<213> ORGANISM: Solanum neorossii

<400> SEQUENCE: 6

Met Asn Tyr Cys Val Tyr Lys Thr Trp Ala Val Asp Ser Asn Thr Lys
1               5                   10                  15

Ala Asn Ser Thr Ser Phe Leu Ser Phe Ser Tyr Phe Pro Phe Leu
            20                  25                  30

Ile Leu Thr Phe Arg Lys Lys Lys Phe Asn Glu Lys Leu Lys Glu Met
            35                  40                  45

Ala Glu Ile Leu Leu Thr Ala Val Ile Asn Lys Ser Ile Glu Ile Ala
        50                  55                  60

Gly Asn Val Leu Phe Gln Glu Gly Thr Arg Leu Tyr Trp Leu Lys Glu
65                  70                  75                  80

Asp Ile Asp Trp Leu Gln Arg Glu Met Arg His Ile Arg Ser Tyr Val
                85                  90                  95

Asp Asn Ala Lys Ala Lys Glu Val Gly Gly Asp Ser Arg Val Lys Asn
            100                 105                 110

Leu Leu Lys Asp Ile Gln Gln Leu Ala Gly Asp Val Glu Asp Leu Leu
        115                 120                 125

Asp Glu Phe Leu Pro Lys Ile Gln Gln Ser Asn Lys Phe Ile Cys Cys
    130                 135                 140

Leu Lys Thr Val Ser Phe Ala Asp Glu Phe Ala Met Glu Ile Glu Lys
145                 150                 155                 160

Ile Lys Arg Arg Val Ala Asp Ile Asp Arg Val Arg Thr Thr Tyr Ser
                165                 170                 175

Ile Thr Asp Thr Ser Asn Asn Asn Asp Asp Cys Ile Pro Leu Asp Arg
            180                 185                 190

Arg Arg Leu Phe Leu His Ala Asp Glu Thr Glu Val Ile Gly Leu Glu
        195                 200                 205

Asp Asp Phe Asn Thr Leu Gln Ala Lys Leu Leu Asp His Asp Leu Pro
    210                 215                 220

Tyr Gly Val Val Ser Ile Val Gly Met Pro Gly Leu Gly Lys Thr Thr
225                 230                 235                 240

Leu Ala Lys Lys Leu Tyr Arg His Val Cys His Gln Phe Glu Cys Ser
                245                 250                 255

Gly Leu Val Tyr Val Ser Gln Gln Pro Arg Ala Gly Glu Ile Leu His
            260                 265                 270

Asp Ile Ala Lys Gln Val Gly Leu Thr Glu Glu Arg Lys Glu Asn
        275                 280                 285

Leu Glu Asn Asn Leu Arg Ser Leu Leu Lys Ile Lys Arg Tyr Val Ile
    290                 295                 300

Leu Leu Asp Asp Ile Trp Asp Val Glu Ile Trp Asp Asp Leu Lys Leu
305                 310                 315                 320

Val Leu Pro Glu Cys Asp Ser Lys Ile Gly Ser Arg Ile Ile Thr
                325                 330                 335

Ser Arg Asn Ser Asn Val Gly Arg Tyr Ile Gly Gly Asp Phe Ser Ile
            340                 345                 350

His Val Leu Gln Pro Leu Asp Ser Glu Lys Ser Phe Glu Leu Phe Thr
        355                 360                 365

```
Lys Lys Ile Phe Asn Phe Val Asn Asp Asn Trp Ala Asn Ala Ser Pro
    370             375             380

Asp Leu Val Asn Ile Gly Arg Cys Ile Val Glu Arg Cys Gly Gly Ile
385             390             395             400

Pro Leu Ala Ile Val Val Thr Ala Gly Met Leu Arg Ala Arg Gly Arg
            405             410             415

Thr Glu His Ala Trp Asn Arg Val Leu Glu Ser Met Ala His Lys Ile
        420             425             430

Gln Asp Gly Cys Gly Lys Val Leu Ala Leu Ser Tyr Asn Asp Leu Pro
    435             440             445

Ile Ala Leu Arg Pro Cys Phe Leu Tyr Phe Gly Leu Tyr Pro Glu Asp
450             455             460

His Glu Ile Arg Ala Phe Asp Leu Thr Asn Met Trp Ile Ala Glu Lys
465             470             475             480

Leu Ile Val Val Asn Thr Gly Asn Gly Arg Glu Ala Glu Ser Leu Ala
            485             490             495

Asp Asp Val Leu Asn Asp Leu Val Ser Arg Asn Leu Ile Gln Val Ala
        500             505             510

Lys Arg Thr Tyr Asp Gly Arg Ile Ser Ser Cys Arg Ile His Asp Leu
    515             520             525

Leu His Ser Leu Cys Val Asp Leu Ala Lys Glu Ser Asn Phe Phe His
530             535             540

Thr Glu His Tyr Ala Phe Gly Asp Pro Ser Asn Val Ala Arg Val Arg
545             550             555             560

Arg Ile Thr Phe Tyr Ser Asp Asp Asn Ala Met Asn Glu Phe Phe His
            565             570             575

Leu Asn Pro Lys Pro Met Lys Leu Arg Ser Leu Phe Cys Phe Thr Lys
        580             585             590

Asp Arg Cys Ile Phe Ser Gln Met Ala His Leu Asn Phe Lys Leu Leu
    595             600             605

Gln Val Leu Val Val Val Met Ser Gln Lys Gly Tyr Gln His Val Thr
610             615             620

Phe Pro Lys Lys Ile Gly Asn Met Ser Cys Leu Arg Tyr Val Arg Leu
625             630             635             640

Glu Gly Ala Ile Arg Val Lys Leu Pro Asn Ser Ile Val Lys Leu Lys
            645             650             655

Cys Leu Glu Thr Leu Asp Ile Phe His Ser Ser Ser Lys Leu Pro Phe
        660             665             670

Gly Val Trp Glu Ser Lys Ile Leu Arg His Leu Cys Tyr Thr Glu Glu
    675             680             685

Cys Tyr Cys Val Ser Phe Ala Ser Pro Phe Cys Arg Ile Met Pro Pro
690             695             700

Asn Asn Leu Gln Thr Leu Met Trp Val Asp Asp Lys Phe Cys Glu Pro
705             710             715             720

Arg Leu Leu His Arg Leu Ile Asn Leu Arg Thr Leu Cys Ile Met Asp
            725             730             735

Val Ser Gly Ser Thr Ile Lys Ile Leu Ser Ala Leu Ser Pro Val Pro
        740             745             750

Lys Ala Leu Glu Val Leu Lys Leu Arg Phe Phe Lys Asn Thr Ser Glu
    755             760             765

Gln Ile Asn Leu Ser Ser His Pro Asn Ile Val Glu Leu Gly Leu Val
770             775             780

Gly Phe Ser Ala Met Leu Leu Asn Ile Glu Ala Phe Pro Pro Asn Leu
```

```
            785                 790                 795                 800
Val Lys Leu Asn Leu Val Gly Leu Met Val Asp Gly His Leu Leu Ala
                805                 810                 815
Val Leu Lys Lys Leu Pro Lys Leu Arg Ile Leu Ile Leu Leu Trp Cys
                820                 825                 830
Arg His Asp Ala Glu Lys Met Asp Leu Ser Gly Asp Ser Phe Pro Gln
                835                 840                 845
Leu Glu Val Leu Tyr Ile Glu Asp Ala Gln Gly Leu Ser Glu Val Thr
                850                 855                 860
Cys Met Asp Asp Met Ser Met Pro Lys Leu Lys Lys Leu Phe Leu Val
865                 870                 875                 880
Gln Gly Pro Asn Ile Ser Pro Ile Ser Leu Arg Val Ser Glu Arg Leu
                885                 890                 895
Ala Lys Leu Arg Ile Ser Gln Val Leu
                900                 905

<210> SEQ ID NO 7
<211> LENGTH: 2718
<212> TYPE: DNA
<213> ORGANISM: Solanum okadae

<400> SEQUENCE: 7
atgaattatt gtgtttacaa gacttgggcc gttgactcta acactaaagc aaatagtaca      60
tctttcttat ccttttctc ttactttccc ttcctcatcc tcacatttag aaaaaagaaa     120
tttaacgaaa aattaaagga gatggctgaa attcttctca cagcagtcat caataaatca     180
atagaaatag ctggaaatgt actctttcaa gaaggtacgc gtttatattg gttgaaagag     240
gacatcgatt ggctccagag agaaatgaga cacattcgat catatgtaga caatgcaaag     300
gcaaaggaag ttggaggcga ttcaagggtg aaaaacttat taaagatat caacaactg      360 gcaggtgatg tggaggatct attagatgag tttcttccaa aaattcaaca atccaataag     420
ttcatttgtt gccttaagac ggtttctttt gccgatgagt ttgctatgga gattgagaag     480
ataaaaagaa gagttgctga tattgaccgt gtaaggacaa cttacagcat cacagataca     540
agtaacaata tgatgattg cattccattg gaccggagaa gattgttcct tcatgctgat     600
gaaacagagg tcatcggtct ggaagatgac ttcaatacac tacaagccaa attacttgat     660
catgatttgc cttatggagt tgtttcaata gttggcatgc ccggtttggg aaaaacaact     720
cttgccaaga aactttatag gcatgtctgt catcaatttg agtgttcggg actggtctat     780
gtttcacaac agccaagggc gggagaaatc ttacatgaca tagccaaaca agttggactg     840
acggaagagg aaaggaaaga aaacttggag aacaacctac gatcactctt gaaaataaaa     900
aggtatgtta ttctcttaga tgacatttgg gatgttgaaa tttgggatga tctaaaactt     960
gtccttcctg aatgtgattc aaaaattggc agtaggataa ttataacctc tcgaaatagt    1020
aatgtaggca gatacatagg aggggatttc tcaatccacg tgttgcaacc cctagattca    1080
gagaaaagct tgaactcttt taccaagaaa atctttaatt ttgttaatga taattgggcc    1140
aatgcttcac cagactggt aaaatattgg agatgtatag ttgagagatg tggaggtata    1200
ccgctagcaa ttgtggtgac tgcaggcatg ttaagggcaa gaggaagaac agaacatgca    1260
tggaacagag tacttgagag tatggctcat aaaattcaag atggatgtgg taaggtattg    1320
gctctgagtt acaatgattt gcccattgca ttaaggccat gtttcttgta ctttggtctt    1380 tacccccgagg accatgaaat tcgtgctttt gatttgacaa atatgtggat tgctgagaag    1440
ctgatagttg taaatactgg caatgggcga gaggctgaaa gtttggcgga tgatgtccta    1500
```

| aatgatttgg tttcaagaaa cttgattcaa gttgccaaaa ggacatatga tggaagaatt | 1560 |
| tcaagttgtc gcatacatga cttgttacat agtttgtgtg tggacttggc taaggaaagt | 1620 |
| aacttctttc acacggagca ctatgcattt ggtgatccta gcaatgttgc tagggtgcga | 1680 |
| aggattacat tctactctga tgataatgcc atgaatgagt tcttccattt aaatcctaag | 1740 |
| cctatgaagc ttcgttcact tttctgtttc acaaaagacc gttgcatatt ttctcaaatg | 1800 |
| gctcatctta acttcaaatt attgcaagtg ttggttgtag tcatgtctca aaagggttat | 1860 |
| cagcatgtta ctttccccaa aaaaattggg aacatgagtt gcctacgcta tgtgcgattg | 1920 |
| gaggggggcaa ttagagtaaa attgccaaat agtattgtca agctcaaatg tctagagacc | 1980 |
| ctggatatat ttcatagctc tagtaaactt ccttttggtg tttgggagtc taaaatattg | 2040 |
| agacatcttt gttacacaga agaatgttac tgtgtctctt ttgcaagtcc attttgccga | 2100 |
| atcatgcctc ctaataatct acaaactttg atgtgggtgg atgataaatt ttgtgaacca | 2160 |
| agattgttgc accgattgat aaatttaaga acattgtgta taatgatgt atccggttct | 2220 |
| accattaaga tattatcagc attgagcct gtgcctaaag cgttggaggt tctgaagctc | 2280 |
| agattttca agaacacgag tgagcaaata aacttgtcgt cccatccaaa tattgtcgag | 2340 |
| ttgggtttgg ttggtttctc agcaatgctc ttgaacattg aagcattccc tccaaatctt | 2400 |
| gtcaagctta atcttgtcgg cttgatggta gacggtcatc tattggcagt gcttaagaaa | 2460 |
| ttgcccaaat taaggatact tatattgctt tggtgcagac atgatgcaga aaaaatggat | 2520 |
| ctctctggtg atagctttcc gcaacttgaa gttttgtata ttgaggatgc acaagggttg | 2580 |
| tctgaagtaa cgtgcatgga tgatatgagt atgcctaaat tgaaaaagct atttcttgta | 2640 |
| caaggcccaa acatttcccc aattagtctc agggtctcgg aacggcttgc aaagttgaga | 2700 |
| atatcacagg tactataa | 2718 |

<210> SEQ ID NO 8
<211> LENGTH: 4310
<212> TYPE: DNA
<213> ORGANISM: Artificial sequence
<220> FEATURE:
<223> OTHER INFORMATION: Synthetic sequence: Nucleic acid sequence of
    Rpi-oka1 Transgene from PSLJ21152 (includes own promoter and
    terminator)

<400> SEQUENCE: 8

| agttatacac cctacattct actcgagtca ttatgatgat gtctcacgac caaatcaaat | 60 |
| caaagttaaa taaatatcga accgaacgcc cactctgtat gagtatggca aaagattttg | 120 |
| agagaatcaa gttgcataaa agcctaattt tcatggaaca tacaaattga gtctcataat | 180 |
| agcccaaact cacagccatg aacccaaatt gggtaaagtt ttgcaagacg ttcatcaaac | 240 |
| agttaggaaa cataaaatgg cgctagatat ataataaatt ttttttaacat atggtgtgat | 300 |
| tgatagttat atactaaaga tgtttgctta gttacgtaat ttttttcaaaa aaaaaaggta | 360 |
| cattatcaat catcagtcac aaaatattaa aagttactgt tgttttttta aattccatgt | 420 |
| cgaatttaat tgaatgacac ttaaattggg acgaacggtg taattctttt tgactattct | 480 |
| actagtatct atccacagca cgtgttgttc ctttcttctt tcgttttta tttacttgac | 540 |
| attattagga gacttggccc tgaactccaa ctattctaag ctgacctttc ttttccttta | 600 |
| ccaattatct tcttctttct aatttcgttt tacgcgtagt actgcctgaa ttttctgact | 660 |
| ttcaacgttt gttattcatg cttgaaaacg aaataccagc taacaaaaga tgaattattg | 720 |
| tgtttacaag acttgggccg ttgactctta cttttccctt ctcatcctca catttagaaa | 780 |

```
aaagaaattt aacgaaaaat taaaggagat ggctgaaatt cttctcacag cagtcatcaa    840
taaatcaata gaaatagctg gaaatgtact cttttcaagaa ggtacgcgtt tatattggtt    900
gaaagaggac atcgattggc tccagagaga aatgagacac attcgatcat atgtagacaa    960
tgcaaaggca aaggaagttg gaggcgattc aagggtgaaa aacttattaa aagatattca   1020
acaactggca ggtgatgtgg aggatctatt agatgagttt cttccaaaaa ttcaacaatc   1080
caataagttc atttgttgcc ttaagacggt ttcttttgcc gatgagtttg ctatggagat   1140
tgagaagata aaaagaagag ttgctgatat tgaccgtgta aggacaactt acagcatcac   1200
agatacaagt aacaataatg atgattgcat tccattggac cggagaagat tgttccttca   1260
tgctgatgaa acagaggtca tcggtctgga agatgacttc aatacactac aagccaaatt   1320
acttgatcat gatttgcctt atggagttgt ttcaatagtt ggcatgcccg gtttgggaaa   1380
aacaactctt gccaagaaac tttataggca tgtctgtcat caatttgagt gttcgggact   1440
ggtctatgtt tcacaacagc caagggcggg agaaatctta catgacatag ccaaacaagt   1500
tggactgacg gaagaggaaa ggaaagaaaa cttggagaac aacctacgat cactcttgaa   1560
aataaaaagg tatgttattc tcttagatga catttgggat gttgaaattt gggatgatct   1620
aaaacttgtc cttcctgaat gtgattcaaa aattggcagt aggataatta taacctctcg   1680
aaatagtaat gtaggcagat acataggagg ggatttctca atccacgtgt tgcaaccccct  1740
agattcagag aaaagctttg aactctttac caagaaaatc tttaattttg ttaatgataa   1800
ttgggccaat gcttcaccag acttggtaaa tattggtaga tgtatagttg agagatgtgg   1860
aggtataccg ctagcaattg tggtgactgc aggcatgtta agggcaagag gaagaacaga   1920
acatgcatgg aacagagtac ttgagagtat ggctcataaa attcaagatg gatgtggtaa   1980
ggtattggct ctgagttaca atgatttgcc cattgcatta aggccatgtt tcttgtactt   2040
tggtctttac cccgaggacc atgaaaattcg tgcttttgat ttgacaaata tgtggattgc   2100
tgagaagctg atagttgtaa atactggcaa tgggcgagag gctgaaagtt ggcggatga   2160
tgtcctaaat gatttggttt caagaaaactt gattcaagtt gccaaaagga catatgatgg   2220
aagaatttca agttgtcgca tacatgactt gttacatagt ttgtgtgtgg acttggctaa   2280
ggaaagtaac ttccttccaca cggagcacaa tgcatttggt gatcctagca atgttgctag   2340
ggtgcgaagg attacattct actctgatga taatgccatg aatgagttct tccatttaaa   2400
tcctaagcct atgaagcttc gttcacttttt ctgtttcaca aaagaccgtt gcatattttc   2460
tcaaatggct catcttaact tcaaattatt gcaagtgttg gttgtagtca tgtctcaaaa   2520
gggttatcag catgttactt tccccaaaaa aattgggaac atgagttgcc tacgttatgt   2580
gcgattggag ggggcaatta gagtaaaatt gccaaatagt attgtcaagc tcaaatgtct   2640
agagaccctg gatatatttc atagctctag taaacttcct tttggtgttt gggagtctaa   2700
aatattgaga catctttgtt acacagaaga atgttactgt gtctcttttg caagtccatt   2760
ttgccgaatc atgcctccta ataatctaca aactttgatg tgggtggatg ataaattttg   2820
tgaaccaaga ttgttgcacc gattgataaa tttaagaaca ttgtgtataa tggatgtatc   2880
cggttctacc attaagatat tatcagcatt gagccctgtg cctagagcgt ggaggttct   2940
gaagctcaga tttttcaaga acacgagtga gcaaataaac ttgtcgtccc atccaaatat   3000
tgtcgagttg ggtttggttg gtttctcagc aatgctcttg aacattgaag cattccctcc   3060
aaatcttgtc aagcttaatc ttgtcggctt gatggtagac ggtcatctat tggcagtgct   3120
taagaaattg cccaaattaa ggatacttat attgctttgg tgcagacatg atgcagaaaa   3180
```

```
aatggatctc tctggtgata gctttccgca acttgaagtt ttgtatattg aggatgcaca    3240
agggttgtct gaagtaacgt gcatggatga tatgagtatg cctaaattga aaaagctatt    3300
tcttgtacaa ggcccaaaca tttccccaat tagtctcagg gtctcggaac ggcttgcaaa    3360
gttgagaata tcacaggtac tataaataat tatttacgtt taatatccat gattttttta    3420
aatttgtatt tagttcatca actaaatatt ccatgtctaa taaattgcag ggatgccttt    3480
gaaaatgatt ctgtgttgga gagaatcttc tgatgcctgt tggtattata atactaataa    3540
taagagaaaa agtttgatta ctgtttcaag ttaattgctt gtgatttgta aaacaaatt     3600 acttttatat ttctctttgt tttattttat gtttatttat ctttaattaa tggagtaata    3660
aaataaaaat cttattttca atagaaaaaa gtagacctta tttgtggtgc atgtatggta    3720 tcttttttgaa attttttgata tatttgctct ttgattcgaa tttcttgctt atatgatgat    3780
ttgcataaat ataaaatatt atacaaatac ctatgggttg gaaaatatag aaatatgcca    3840
atcaaatgta tacaaaaatc attaatagat agaatcgtaa aagatataca aatgagaaat    3900
gcttgactaa gaagcttcgt gcaacctctc acactgagca caatgcattt ggtgatctcg    3960
gcactattgc tgttacttgt aagactacgt tccccaataa gtctttccaa acggcttgca    4020
aagctgagaa tatgaaaatc tcataggtta gtttgctgcg ttaattattt acatttaata    4080
tgctcgataa ggtgatttta aaaaaatttg tactagttaa ttcatgaact aaatatttca    4140
tttaatactc cataattctg aatatggaaa ataaataata tttaataaca agaataaaat    4200
gataaattat tcattgattt tataaattgg ataaatatta ttaaatattc ttaaataata    4260
taatgaacaa gtgaagatga acggagggag tatgaagcct cttttcaaag               4310
```

<210> SEQ ID NO 9
<211> LENGTH: 2571
<212> TYPE: DNA
<213> ORGANISM: Solanum mochiquense

<400> SEQUENCE: 9

```
atggctgaaa ttcttcttac aacagtcatc aataaatctg taggaatagc tgcaaatgta      60
ctctttcaag aaggaacgcg tttatattgg ttgaaagagg acatagattg gctccacaga     120
gaaatgagac acattcgatc atatgtagac gatgcaaagg ccaaggaagt tggaggcgat     180
tcaagggtca gaaacttatt aaaagatatt caacaactgg caggtgatgt ggaggatcta     240
ttagatgagt ttcttccaaa aattcaacaa tccaataagt tcatttgttg ccttaagaca     300
gtttcttttg ccgatgagtt tgccatggag attgagaaga taaaagaag agttgctgat     360 attacccgtg taaggacaac ttacaacatc acagatacaa gtaacaataa tgatgattgc     420
attccattgg accggagaag attgttcctt catgctgatg aaacagaggt catcggtctg     480
gaagatgact tcaatacact aaaagccaaa ttacttgatc aagatttgcc ttatggagtt     540
gtttcaatag ttggcatgcc cggtctagga aaaacaactc ttgccaagaa actttatagg     600
catgtccgtg atcaatttga gagctcggga ctggtctacg tgtcccaaca gccaagagcg     660
ggagaaatct tacgtgacat agccaaacaa gttggactgc caaaagagga aaggaaagaa     720
aacttggagg gcaacctacg atcactcttg aaaacaaaaa ggtatgttat cctcctagat     780
gacatttggg atgttgaaat tgggatgat ctaaaactcg tccttcctga atgtgattca     840
gaaattggca gtaggataat tataaccttct cgaaatagta atgtaggcag atacatagga     900
ggggatttct caattcacat gttgcaacct ctagattcgg agaacagttt tgaactcttt    960
accaagaaaa tctttacttt tgataacaat aataattggg ccaatgcttc accagacttg   1020
```

-continued

```
gtagatattg gtagaagtat agttggtaga tgcggaggta tacctctagc cattgtggtc   1080
actgcaggca tgttaagggc aagagaaaga acagaacatg catggaacag agtacttgag   1140
agtatgggcc ataaagttca agatggatgt gctaaggtat tggctttgag ttacaatgat   1200
ttgcccattg cattaaggcc atgtttcttg taccttggcc ttttccccga ggaccatgaa   1260
attcgtgcct ttgatttgac aaatatgtgg attgctgaga agctgatagt tgtaaatagt   1320
ggcaatgggc gagaggctga agtttggcg gaggatgttc taaatgattt tgtttctaga    1380
aacttgattc aagtttccca agaaaatgt aatggaagaa tttcaagtta tcgcatacat    1440
gacttgttac atagtttgtg cgtcgaattg ggcaaggaaa gtaacttttt tcacactgaa   1500
cacaatgcat ttggtgatcc agacaatgtt gctagggtgc gaaggattac attctactct   1560
gataataatg ccatgagtaa gttcttccgt tcaaatccta agcctaagaa acttcgtgca   1620
cttttctgtt tcacaaattt agactcttgc atattttctc atttggctca tcatgacttc   1680
aaattattac aagtgttggt tgtagttatc tcttataatt ggttgagtgt cagtatctca   1740
aacaaatttg ggaagatgag ttgcttgcgc tatttgagat tggaggggcc aattgtggga   1800
gaactgtcaa atagtattgt gaagctcaaa cgtgtagaga ccatagatat tgcagggat    1860 aacattaaaa ttccttgtgg tgtttgggag tctaaacaat tgagacatct ccgtaataga   1920
gaagaacgtc gctatttctt ttctgtaagc ccattttgcc taaacatgta cccattgcct   1980
cctaataatc tacaaacttt ggtgtggatg gatgataaat ttttttgaacc gagattgttg   2040 caccgattga tcaatttaag aaaattgggt atatggggca catctgattc tacaattaag   2100
atattatcag cattgagccc tgtgccaaca gcgttggagg ttctgaagct ctactttttg   2160
agggacctga gtgagcaaat aaacttgtca acctatccaa atattgttaa gttgaatttg   2220
caaggattcg taagagtgcg cttgaactct gaagcattcc ctccaaatct tgtcaagctt   2280
attcttgaca aaattgaggt agagggtcat gtagtggcag ttcttaagaa attgcccaca   2340
ttaaggatac ttaaaatgta tgggtgcaaa cataatgaag aaaagatgga tctctctggt   2400
gatggtgatg gtgatagctt tccgcaactt gaagttttgc atattgagag accattcttc   2460 ttgttttgaaa taacgtgcac agatgatgac agtatgccta aattgaaaaa gctattactt   2520
accacttcga acgttaggct ctcggaaaga cttgcaaaac tgagagtatg a             2571
```

<210> SEQ ID NO 10
<211> LENGTH: 5871
<212> TYPE: DNA
<213> ORGANISM: Artificial sequence
<220> FEATURE:
<223> OTHER INFORMATION: Synthetic sequence: Nucleic acid sequence of a
      portion of Rpi-mcq 1.1 Transgene from PSLJ21153 (includes own
      promoter and terminator)

<400> SEQUENCE: 10

```
ggatctgggt tttacccggt cttttattaa atgggtggta gaaaataaat tatatatata     60 tatttttgg agtgaacaca cgcgcaggtg ctgagattac cattgttgtc caaatggtgt    120
atttataatg gttgaaaatt gtttcgtggt gtaatagggac tcccacaaac tttaagtgtc   180
tgcttcaaaa aatggtttaa gtttaatggg gtaactatgt atttcctcta actaaaaatc    240
aaaaaccata gcaaaaaaat aaggtaaaga accataatat aatcaaataa gcataaaccc    300
atctcaaaaa actcattttt tttaacaata aaccaaacat aaaaccaata taccccaaag    360
acttaacaaa gtttcatatt aactaaaaat caaaaaccat agtaaagcaa taacgtaaag    420
aaccataata taatcaaata agcataaacc catctcaaaa actcattttt ttcatcaaac    480
```

```
atcaaaaaac aatgagtaaa agttctacaa caagaaccaa acataaaacc aagagacccc      540
aaagacttaa caaagttcca tattaacaaa aaatcaacaa ccataacaaa acaataaggc      600
aaagaacaat agcataacca aataagcata aacccatctt aaaaaactca tttttatcac      660
caaacattaa aaaactcatt tttttcacca aacatcaaaa aacaatgagt aaaagttcta      720
caacatgaac caaacataaa accaacatac cccaaacact taacaaagct ccatataaac      780
aacaaaacaa caaggcaaag aagcataata tagcaaaata agcataaatc catctcaaac      840
aaattataaa aaaactaacc taatgaagac aagttttcag ggtttaagag gcaagaaaat      900
gagaagcggc taggtcttac tgtgaactgt ggggtttaag aaagggtata tataagtaca      960
ctgcctttcg acttttttcag agtgaaaaaa atactcatat atctgcggcg ttttaaaagg     1020
agctcgaggg taattttact gcttagaggt gttgtacctt gattttttaaa gagagtattt     1080 ttggaattaa tgtacaacat gcattatgcg aactcataat agtttgtaaa tgagcaattg     1140
tcgagattat gaaagctatt ttaggatgtt atgtgaatta tttgtattta tttcgaaata     1200 gttttttcact ttatttcaaa agcagtttga ttgtaaaaat cgtcaatttt tagttgtttt    1260
attctttcat ttgcaagaaa aaaaaattaa gcataaatct atttttcaatt tcaattctat    1320 aaatattacg aaaaatattt gaatttcaca atcaaatgcc catttagttt ttttttttt      1380 aaactttaat acgagacttt tttcatattt tatattttcc tcaaattaga tcctttttt     1440 tcctttcctt gttgtaagtc cttgtgaaaa aacctccaaa tcctaacttg tgttgtgata     1500
ccacaaggat ttaaagatta cacataatga aacaaaaaaa aaaaaaaatc aattcgagct    1560
tcgaaaatga aaaaaattga taaattttttt ttttcttttaa tcactattac gtgatacaaa   1620
tttgaattag tcgaattaat atatttaaaa caaacactc cttatcagaa aagtgaagaa     1680
attctgacca ttccactaga gtcattatgg tgatggaagt ttaataaaat agaaccgaag     1740
aatcgaatgc ccactcaaat tttttttgaga gcccaaactc acagccatga acccaaattg    1800
ggtaaagttt tgcaagacgt tcatctaaca gttaggaaac ttaaaatgcc gtctagatat    1860
ataatttatt tttttaacat atcgtgtgat tgatatatac taaagatgtt tgcttagtta    1920
cgtgattttt ttaaaaaaaa agagagtaca ttatcaatca tcagccacaa aatattaaaa    1980
gtcacagttt gtttcttaaa ttccatatcg aattaaattg aatgacagtt aaattggaat    2040
gaatggtgta atttcctttg actattgtac tagtatctta tccacagcat gtgttgttcc    2100
ttccttcttt cgttttttcat ttacttgaca ttagtaggag acttggcagt ggactccaac   2160
tattctaagc tgacctttct tttcctttac caattatctt ctcttttcta atttctcatt    2220
ctgatcggtt tttgtagcta ctgaaaaaga aagagtgaag aaatggctga aattcttctt    2280
acagcagtca tcaataaatc tgtagaaata gctggaaatg tactctttca agaaggtacg    2340
cgtttatatt ggttgaagga ggatatagat tggctccaaa gagaaatgag acacattcga    2400
tcatatgtag acaatgcaaa ggccaaggaa gttggaggtg attcaagggt gaaaaactta    2460
ttaaaagata ttcaacaact cgcaggtgat gtggaggatc tcctagatga gtttcttcca    2520
aaaattcaac aatccagtaa gttcaaaggc gcaatttgtt gccttaagac cgtttctttt    2580
gcggatgagt ttgctatgga gattgagaag ataaaaagaa gggttgtgga cattgatcgt    2640
gtaaggacaa cttacaacat catggataca aataacaaca atgattgcat tccattggac    2700
cagagaagat tgttccttca tgttgatgaa acagaggtca tcggtttgga tgatgacttc    2760
aatacactac aagccaaatt acttgaccaa gatttgcctt atggagttgt ttcaatagtt    2820
ggcatgcccg gtctaggaaa aacaactctt gccaagaaac tttataggca tgtccgtcat    2880
```

```
aaatttgagt gttcgggact ggtctatgtt tcacaacagc caagggcggg agaaatctta    2940
atcgacatag ccaaacaagt tggactgacg gaagacgaaa ggaaagaaaa cttggagaac    3000
aacctacggt cactcttgaa aagaaaaagg tatgttattc tcttagatga catttgggat    3060
gttgaaattt gggatgatct aaaacttgtc cttcctgaat gtgattcaaa aattggcagt    3120
aggataatta taacctctcg aaatagtaat gtaggcagat acataggagg ggatttctca    3180
attcacgtgt tgcaacctct aaattcggag aacagttttg aactctttac caagaaaatc    3240
tttattttg ataacaataa taattggacc aatgcttcac caaacttggt agatattggt    3300
agaagtatag ttggtagatg tggtggtata ccactagcca ttgtggtgac tgcaggcatg    3360
ttaagggcaa gagaaagaac agaacgtgca tggaacaggt tacttgagag tatgagccat    3420
aaagttcaag atggatgtgc taaggtattg gctctgagtt acaatgattt gccaattgca    3480
ttaaggccat gtttcttgta ttttggcctt taccccgagg atcatgaaat tcgtgctttt    3540
gatttgacaa atatgtggat tgctgagaag ttgatagttg taaatagtgg caatgggcga    3600
gaggctgaaa gtttggcgga tgatgtccta aatgatttgg tttcaagaaa catgattcaa    3660
gttgccaaaa ggacatatga tggaagaatt tcaagttgtc gcatacatga cttgttacat    3720
agtttgtgtg ttgacttggc taaggaaagc aacttctttc acaccgagca caatgcattg    3780
ggtgatcccg gaaatgttgc taggctgcga aggattacta tctactctga taataatgcc    3840
atgaatgagt tcttccgttc aaatcctaag cttgagaagc ttcgtgcact tttctgtttt    3900
acagaagacc cttgcatatt ttctcaactg gctcatcttg atttcaaatt attgcaagtg    3960
ttggttgtag tcatctttgt tgatgatatt tgtggtgtca gtatcccaaa cacatttggg    4020
aacatgaggt gcttacgtta tctgcgattc caggggcatt tttatgggaa actgccaaat    4080
tgtatggtga agctcaaacg tctagagacc ctcgatattg ttatagctt aattaaattt    4140
cctactggtg tttggaagtc tacacaattg aaacatcttc gttatggagg tttttaatcaa    4200
gcatctaaca gttgctttc tataagccca ttttttcccaa acttgtactc attgcctcat    4260
aataatgtac aaactttgat gtggctggat gataaatttt ttgaggcggg attgttgcac    4320
cgattgatca atttaagaaa actgggtata gcaggagtat ctgattctac agttaagata    4380
ttatcagcat tgagccctgt gccaacggcg ctggaggttc tgaagctcaa aatttacagg    4440
gacatgagtg agcaaataaa cttgtcgtcc tatccaaata ttgttaagtt gcgtttgaat    4500
gtttgcggaa gaatgcgctt gaactgtgaa gcatttcctc caaatcttgt caagcttact    4560
cttgtcggcg atgaggtaga cggtcatgta gtggcagagc ttaagaaatt gcccaaatta    4620
aggatactta aaatgtttgg gtgcagtcat aatgaagaaa agatggatct ctctggtgat    4680
ggtgatagct ttccgcaact tgaagttctg catattgatg aaccagatgg gttgtctgaa    4740
gtaacgtgta gggatgatgt cagtatgcct aaattgaaaa agttgttact tgtacaacgc    4800
cgcccttctc caattagtct ctcagaacgt cttgcaaagc tcagaatatg aaattcacaa    4860
tgtgtcaata tataggttag tttgctacgt taatctccca ttatgtctaa tgaattgcgc    4920
gcagatgcat ttgagaatga ttgattgtaa attgtaattg taataaataa ataaatgttt    4980
gattgctttc tgaagttgat gtatttgtgg cttgtgattt gtaaaacata tttatttatt    5040
gtcttatcac ttatgtttat ttaccttgg aattagcagt agctttcgtt tcttctcttc    5100
ttcaataatc aatgctcgca aatataaatt aggggcgtat tttattggtt tggtttatcg    5160
gtttataaat tcgtttaatt aataaccaat tcaattaaat attttttat cggttttggg    5220
tccttagcgg ttcgatattt gatttaacca ataagaaaat acttataaaa caaatatatg    5280
```

| | |
|---|---|
| acttctcaaa caatttagcg tggcaagata ataccgtaac tttacaaata ctcataaaat | 5340 |
| agaaacaaca ataactaaca tgaaaagaat tatacaagtg taacacaaag aaaaactaag | 5400 |
| aggaatatgc ttcttacttt acattttgac gttttgtata atgtgaattt ttgaacttaa | 5460 |
| agtcactgtg aagtgtgatg tgaaggtgaa aggacaaatg cactaactag taaggtattg | 5520 |
| cgattaatat ttaatgttta tgtatgagta aaatagtaaa ttattatagt tttattgggt | 5580 |
| tatcagtata cccaataact caatattaaa aatcaaaatc gaaccggtaa cccaatattt | 5640 |
| ttttctttct ataaaaccat taaaacctca ttgacccaat aacccaataa caataaatca | 5700 |
| atagcacttt tttcatttta atttatcgat cgattagatt tttgcaaccc actaatataa | 5760 |
| attactacct gttatagcaa gtgcaagtag agaattgata tatagctcac attttacaaa | 5820 |
| ttctttctag tgttaatcgt caaaaacatt agcttctcaa taatatatgg c | 5871 |

<210> SEQ ID NO 11
<211> LENGTH: 5567
<212> TYPE: DNA
<213> ORGANISM: Artificial sequence
<220> FEATURE:
<223> OTHER INFORMATION: Synthetic sequence: Nucleic acid sequence of a
      portion of Rpi-mcq1.2 Transgene from PSLJ21148 (includes own
      promoter and terminator)

<400> SEQUENCE: 11

| | |
|---|---|
| aatagggtta aaatggtaaa ctcactacac caatcattgt tttgcatatt gaggaaccgg | 60 |
| acatgttgcc tgaagttatt gtattttcta tatcatttac atatcataca attaggtcca | 120 |
| atcgcgtttc ctttcttttt tggctagaat ccagcaatat gaacaagaaa aataatacaa | 180 |
| acagtaaatg aaaataaaat tatctgataa tatatttagc ttcagaacca agattgctt | 240 |
| gttacaggtg aaaaaaatac tactccaatg caacgcttaa aactcttcga taatcatata | 300 |
| aaaaggctag tctagattgt actcgaatgt tatcacgtac atggccacat atctgactcc | 360 |
| aaagagagag atatctgccc tcaacacctt cctagctgca atcatcagca gaaatttact | 420 |
| tgttcaaaca ggctcgcgct tatatatatt ggttgaaaga ggacaatgac tggagaagtg | 480 |
| aggcacattc gatattatct agctaggaag gacaacttt ggtatcactc atacaagtaa | 540 |
| caacaatgac caatatgact acgttccact agaccgtgga agattattcc ttcatgttga | 600 |
| tgaaacagag gtcattggtt tggggaaaat actatcaaat attcaagttt actggtaatt | 660 |
| aaaactactg atagtttagt ggatttgaat aaaatgtgtt atgtttataa tggtctttag | 720 |
| atattctacc tatattgaaa gtttcaaact attggaagca atcatttctg catatataaa | 780 |
| aacttatttg cacggaatat ttgtcgcttt acgagttctt tctttcttct ttcgtatact | 840 |
| tgacaatagg agacttgttt gtggactaaa agcgaatagt ggaatatcat tatttttccta | 900 |
| ataactttca gattgaaagg aagtccgtag ctctttccaa tatgtatggt ctctatatgt | 960 |
| ttgagcttga caatatcatt ttacagttct ccaggaatat cccctccaat ctcaaatagt | 1020 |
| caatagtgat atcttcataa taatcttgag gcatgactac caccaacatt tgcaataatt | 1080 |
| tgaagtcaaa atgagtcatt tgataaaata tgcaaggctc ttttgtgaaa caaaaagcct | 1140 |
| tttaggttta ggattcaaag aattgaactc attcataaca tcatcagagt agaatgtaat | 1200 |
| ccttcgcagc gtagcaacgt tgtcaggatc accaaatgca tagtgatcag tgtgaaataa | 1260 |
| gttactacta tcaacttctc agcaatccac atatttgtcc aatcaaaacc atgaatttca | 1320 |
| aggtccttgg gggaaaaggc caaagtacaa atttctacta aatcgtccca aaattgagtt | 1380 |
| ccacattcct ttagatttac taaatctatt ccgacaattc ccactcgaaa gaaatttcaa | 1440 |

```
tttcggaacc aaaaagggtt gtgatggagt ggtaaatatt ccttcatcct taaccaaatc  1500
cggatttaat cgggcttcaa attgagtggt ggaaaaactt tcaatgacct tattaatatt  1560
tacttttttt aaaactagaa agcaaattat gagtgatttg ttaactattc tagctactga  1620
tgctacatac taatacaatc aaatctctac aactaaagtt gtttgtcctg tttacgtttt  1680
agttgttata gcataatgtt gatataaaaa acatttgata taatataatg taacataaat  1740
attgtttttt attttcaaa aataacatg ttaattaatg tattactcct ttttcattag   1800
tgtgtagctg cccccacgtt gtctctccct ttcttctgtc ttttgtttaa tttacttgac  1860
attattagga gacttgattg tggactccag cactaaaaag aaaaagcaaa tagcagatgg  1920
aatgagttta agctgatctt tcttttcctaa ttactcgttc tgatctattt tttctagcta  1980
ctgaaaaaga gagaaaaaaa tggctgaaat tcttcttaca acagtcatca ataaatctgt  2040
aggaatagct gcaaatgtac tctttcaaga aggaacgcgt ttatattggt tgaaagagga  2100
catagattgg ctccacagag aaatgagaca cattcgatca tatgtagacg atgcaaaggc  2160
caaggaagtt ggaggcgatt caagggtcag aaacttatta aaagatattc aacaactggc  2220
aggtgatgtg gaggatctat tagatgagtt tcttccaaaa attcaacaat ccaataagtt  2280
catttgttgc cttaagacag tttcttttgc cgatgagttt gccatggaga ttgagaagat  2340
aaaaagaaga gttgctgata ttacccgtgt aaggacaact tacaacatca cagatacaag  2400
taacaataat gatgattgca ttccattgga ccggagaaga ttgttccttc atgctgatga  2460
aacagaggtc atcggtctgg aagatgactt caatacacta aaagccaaat tacttgatca  2520
agatttgcct tatggagttg tttcaatagt tggcatgccc ggtctaggaa aaacaactct  2580
tgccaagaaa ctttataggc atgtccgtga tcaatttgag agctcgggac tggtctacgt  2640
gtcccaacag ccaagagcgg gagaaatctt acgtgacata gccaaacaag ttggactgcc  2700
aaaagaggaa aggaaagaaa acttggaggg caacctacga tcactcttga aaacaaaaag  2760
gtatgttatc ctcctagatg acatttggga tgttgaaatt tgggatgatc taaaactcgt  2820
ccttcctgaa tgtgattcag aaattggcag taggataatt ataacctctc gaaatagtaa  2880
tgtaggcaga tacataggag gggatttctc aattcacatg ttgcaacctc tagattcgga  2940
gaacagtttt gaactctttta ccaagaaaat ctttactttt gataacaata ataattgggc  3000
caatgcttca ccagacttgg tagatattgg tagaagtata gttggtagat gcggaggtat  3060
acctctagcc attgtggtca ctgcaggcat gttaagggca agagaaagaa cagaacatgc  3120
atggaacaga gtacttgaga gtatgggcca taaagttcaa gatggatgtg ctaaggtatt  3180
ggctttgagt tacaatgatt tgcccattgc attaaggcca tgtttcttgt accttggcct  3240
tttccccgag gaccatgaaa ttcgtgcctt tgatttgaca aatatgtgga ttgctgagaa  3300
gctgatagtt gtaaatagtg gcaatgggcg agaggctgaa agtttggcgg aggatgttct  3360
aaatgatttt gtttctagaa acttgattca agtttcccaa agaaaatgta atggaagaat  3420
ttcaagttat cgcatacatg acttgttaca tagtttgtgc gtcgaattgg gcaaggaaag  3480
taactttttt cacactgaac acaatgcatt tggtgatcca gacaatgttg ctagggtgcg  3540
aaggattaca ttctactctg ataataatgc catgagtaag ttcttccgtt caaatcctaa  3600
gcctaagaaa cttcgtgcac ttttctgttt cacaaattta gactcttgca tatttctca   3660
tttggctcat catgacttca aattattaca agtgttggtt gtagttatct cttataattg  3720
gttgagtgtc agtatctcaa acaaatttgg gaagatgagt tgcttgcgct atttgagatt  3780
ggaggggcca attgtgggag aactgtcaaa tagtattgtg aagctcaaac gtgtagagac  3840
```

```
catagatatt gcaggggata acattaaaat tccttgtggt gtttgggagt ctaaacaatt      3900
gagacatctc cgtaatagag aagaacgtcg ctatttcttt tctgtaagcc cattttgcct      3960
aaacatgtac ccattgcctc ctaataatct acaaactttg gtgtggatgg atgataaatt      4020
ttttgaaccg agattgttgc accgattgat caatttaaga aaattgggta tatgggcac      4080 atctgattct acaattaaga tattatcagc attgagccct gtgccaacag cgttggaggt      4140
tctgaagctc tactttttga gggacctgag tgagcaaata aacttgtcaa cctatccaaa      4200
tattgttaag ttgaatttgc aaggattcgt aagagtgcgc ttgaactctg aagcattccc      4260
tccaaatctt gtcaagctta ttcttgacaa aattgaggta gagggtcatg tagtggcagt      4320
tcttaagaaa ttgcccacat taaggatact taaaatgtat gggtgcaaac ataatgaaga      4380
aaagatggat ctctctggtg atggtgatgg tgatagcttt ccgcaacttg aagttttgca      4440
tattgagaga ccattcttct tgtttgaaat aacgtgcaca gatgatgaca gtatgcctaa      4500
attgaaaaag ctattactta ccacttcgaa cgttaggctc tcggaaagac ttgcaaaact      4560
gagagtatga aaatcccaat gtgtcaacag gttagttatt tacttctaat atctcggaat      4620
aagctaattc atatttaatt gatgaactaa atattttatg tctaataaat tgcagatgca      4680
tttcagaatg atttaagtct ttgctggaga gcatcttcta tgcctgtttg tatttgaaat      4740
aaataaataa aatgtttgat tgcttcctga gttgatgta tttgtggctt gtgatttgta      4800
aaacatattt atttattgtc ttatgtatat ttacctttgg atttagcagt agctttagtt      4860
tattttcttc ttcaagaatc aaagttcaca atataagtta tgacttgcat cgatcggttc      4920
gggttgattt tatgtattgt catttcagtt tattggtttt tggttatggt ttatctatca      4980
attggtttaa ccaataagaa aatgcttata aaataaatat ataatttctc taacaattta      5040
acatgacaag ataataacaa aactttacaa atgttcataa aatagaaatt ataataacta      5100
acattgaaag aactatacaa gtgtagcaca aagagaaact aataggaata gtgttcttac      5160
tttatgtttt gacgttttgt ataatgtgaa gttttgaatt taaagtcatt atgaagtttt      5220
gaagttaagg ctaaaggaca gatgcactaa ctagtaaggt attgagatta atatttaata      5280
tttatgtaca tgaaaagtac tatattacta taatcttatt gggttatcgg tatacccaat      5340
aacccaatat aaaaagcgaa aaccaagcca ataatccttt tttttttata aaatcattaa      5400
aaactattaa cccaataacc caatagaaat aaactaatcc cgggataatt tttgagtggc      5460
ctttaattca ttgtttggtt gcaaaggtag ggataactta tcccaggatt aacaattagt      5520
cctgggataa tttatccctc actagggatc atatagtaat cccatga                   5567
```

<210> SEQ ID NO 12
<211> LENGTH: 905
<212> TYPE: PRT
<213> ORGANISM: Solanum okadae

<400> SEQUENCE: 12

Met Asn Tyr Cys Val Tyr Lys Thr Trp Ala Val Asp Ser Asn Thr Lys
1               5                   10                  15

Ala Asn Ser Thr Ser Phe Leu Ser Phe Phe Ser Tyr Phe Pro Phe Leu
            20                  25                  30

Ile Leu Thr Phe Arg Lys Lys Lys Phe Asn Glu Lys Leu Lys Glu Met
        35                  40                  45

Ala Glu Ile Leu Leu Thr Ala Val Ile Asn Lys Ser Ile Glu Ile Ala
    50                  55                  60

Gly Asn Val Leu Phe Gln Glu Gly Thr Arg Leu Tyr Trp Leu Lys Glu

```
            65                  70                  75                  80
Asp Ile Asp Trp Leu Gln Arg Glu Met Arg His Ile Arg Ser Tyr Val
                    85                  90                  95
Asp Asn Ala Lys Ala Lys Glu Val Gly Gly Asp Ser Arg Val Lys Asn
                100                 105                 110
Leu Leu Lys Asp Ile Gln Gln Leu Ala Gly Asp Val Glu Asp Leu Leu
                115                 120                 125
Asp Glu Phe Leu Pro Lys Ile Gln Gln Ser Asn Lys Phe Ile Cys Cys
            130                 135                 140
Leu Lys Thr Val Ser Phe Ala Asp Glu Phe Ala Met Glu Ile Glu Lys
145                 150                 155                 160
Ile Lys Arg Arg Val Ala Asp Ile Asp Arg Val Arg Thr Thr Tyr Ser
                165                 170                 175
Ile Thr Asp Thr Ser Asn Asn Asp Asp Cys Ile Pro Leu Asp Arg
                180                 185                 190
Arg Arg Leu Phe Leu His Ala Asp Glu Thr Glu Val Ile Gly Leu Glu
            195                 200                 205
Asp Asp Phe Asn Thr Leu Gln Ala Lys Leu Leu Asp His Asp Leu Pro
210                 215                 220
Tyr Gly Val Val Ser Ile Val Gly Met Pro Gly Leu Gly Lys Thr Thr
225                 230                 235                 240
Leu Ala Lys Lys Leu Tyr Arg His Val Cys His Gln Phe Glu Cys Ser
                245                 250                 255
Gly Leu Val Tyr Val Ser Gln Gln Pro Arg Ala Gly Glu Ile Leu His
                260                 265                 270
Asp Ile Ala Lys Gln Val Gly Leu Thr Glu Glu Glu Arg Lys Glu Asn
            275                 280                 285
Leu Glu Asn Asn Leu Arg Ser Leu Leu Lys Ile Lys Arg Tyr Val Ile
            290                 295                 300
Leu Leu Asp Asp Ile Trp Asp Val Glu Ile Trp Asp Asp Leu Lys Leu
305                 310                 315                 320
Val Leu Pro Glu Cys Asp Ser Lys Ile Gly Ser Arg Ile Ile Ile Thr
                325                 330                 335
Ser Arg Asn Ser Asn Val Gly Arg Tyr Ile Gly Gly Asp Phe Ser Ile
                340                 345                 350
His Val Leu Gln Pro Leu Asp Ser Glu Lys Ser Phe Glu Leu Phe Thr
            355                 360                 365
Lys Lys Ile Phe Asn Phe Val Asn Asp Asn Trp Ala Asn Ala Ser Pro
            370                 375                 380
Asp Leu Val Asn Ile Gly Arg Cys Ile Val Glu Arg Cys Gly Gly Ile
385                 390                 395                 400
Pro Leu Ala Ile Val Val Thr Ala Gly Met Leu Arg Ala Arg Gly Arg
                405                 410                 415
Thr Glu His Ala Trp Asn Arg Val Leu Glu Ser Met Ala His Lys Ile
                420                 425                 430
Gln Asp Gly Cys Gly Lys Val Leu Ala Leu Ser Tyr Asn Asp Leu Pro
            435                 440                 445
Ile Ala Leu Arg Pro Cys Phe Leu Tyr Phe Gly Leu Tyr Pro Glu Asp
            450                 455                 460
His Glu Ile Arg Ala Phe Asp Leu Thr Asn Met Trp Ile Ala Glu Lys
465                 470                 475                 480
Leu Ile Val Val Asn Thr Gly Asn Gly Arg Glu Ala Glu Ser Leu Ala
                485                 490                 495
```

```
Asp Asp Val Leu Asn Asp Leu Val Ser Arg Asn Leu Ile Gln Val Ala
            500                 505                 510

Lys Arg Thr Tyr Asp Gly Arg Ile Ser Ser Cys Arg Ile His Asp Leu
        515                 520                 525

Leu His Ser Leu Cys Val Asp Leu Ala Lys Glu Ser Asn Phe Phe His
    530                 535                 540

Thr Glu His Tyr Ala Phe Gly Asp Pro Ser Asn Val Ala Arg Val Arg
545                 550                 555                 560

Arg Ile Thr Phe Tyr Ser Asp Asp Asn Ala Met Asn Glu Phe Phe His
                565                 570                 575

Leu Asn Pro Lys Pro Met Lys Leu Arg Ser Leu Phe Cys Phe Thr Lys
            580                 585                 590

Asp Arg Cys Ile Phe Ser Gln Met Ala His Leu Asn Phe Lys Leu Leu
        595                 600                 605

Gln Val Leu Val Val Val Met Ser Gln Lys Gly Tyr Gln His Val Thr
    610                 615                 620

Phe Pro Lys Lys Ile Gly Asn Met Ser Cys Leu Arg Tyr Val Arg Leu
625                 630                 635                 640

Glu Gly Ala Ile Arg Val Lys Leu Pro Asn Ser Ile Val Lys Leu Lys
                645                 650                 655

Cys Leu Glu Thr Leu Asp Ile Phe His Ser Ser Ser Lys Leu Pro Phe
            660                 665                 670

Gly Val Trp Glu Ser Lys Ile Leu Arg His Leu Cys Tyr Thr Glu Glu
        675                 680                 685

Cys Tyr Cys Val Ser Phe Ala Ser Pro Phe Cys Arg Ile Met Pro Pro
    690                 695                 700

Asn Asn Leu Gln Thr Leu Met Trp Val Asp Asp Lys Phe Cys Glu Pro
705                 710                 715                 720

Arg Leu Leu His Arg Leu Ile Asn Leu Arg Thr Leu Cys Ile Met Asp
                725                 730                 735

Val Ser Gly Ser Thr Ile Lys Ile Leu Ser Ala Leu Ser Pro Val Pro
            740                 745                 750

Lys Ala Leu Glu Val Leu Lys Leu Arg Phe Phe Lys Asn Thr Ser Glu
        755                 760                 765

Gln Ile Asn Leu Ser Ser His Pro Asn Ile Val Glu Leu Gly Leu Val
    770                 775                 780

Gly Phe Ser Ala Met Leu Leu Asn Ile Glu Ala Phe Pro Pro Asn Leu
785                 790                 795                 800

Val Lys Leu Asn Leu Val Gly Leu Met Val Asp Gly His Leu Leu Ala
                805                 810                 815

Val Leu Lys Lys Leu Pro Lys Leu Arg Ile Leu Ile Leu Leu Trp Cys
            820                 825                 830

Arg His Asp Ala Glu Lys Met Asp Leu Ser Gly Asp Ser Phe Pro Gln
        835                 840                 845

Leu Glu Val Leu Tyr Ile Glu Asp Ala Gln Gly Leu Ser Glu Val Thr
    850                 855                 860

Cys Met Asp Asp Met Ser Met Pro Lys Leu Lys Lys Leu Phe Leu Val
865                 870                 875                 880

Gln Gly Pro Asn Ile Ser Pro Ile Ser Leu Arg Val Ser Glu Arg Leu
                885                 890                 895

Ala Lys Leu Arg Ile Ser Gln Val Leu
            900                 905

<210> SEQ ID NO 13
```

```
<211> LENGTH: 856
<212> TYPE: PRT
<213> ORGANISM: Solanum mochiquense

<400> SEQUENCE: 13

Met Ala Glu Ile Leu Leu Thr Thr Val Ile Asn Lys Ser Val Gly Ile
1               5                   10                  15

Ala Ala Asn Val Leu Phe Gln Glu Gly Thr Arg Leu Tyr Trp Leu Lys
            20                  25                  30

Glu Asp Ile Asp Trp Leu His Arg Glu Met Arg His Ile Arg Ser Tyr
        35                  40                  45

Val Asp Asp Ala Lys Ala Lys Glu Val Gly Gly Asp Ser Arg Val Arg
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Ile Cys
                85                  90                  95

Cys Leu Lys Thr Val Ser Phe Ala Asp Glu Phe Ala Met Glu Ile Glu
            100                 105                 110

Lys Ile Lys Arg Arg Val Ala Asp Ile Thr Arg Val Arg Thr Thr Tyr
        115                 120                 125

Asn Ile Thr Asp Thr Ser Asn Asn Asn Asp Asp Cys Ile Pro Leu Asp
    130                 135                 140

Arg Arg Arg Leu Phe Leu His Ala Asp Glu Thr Glu Val Ile Gly Leu
145                 150                 155                 160

Glu Asp Asp Phe Asn Thr Leu Lys Ala Lys Leu Leu Asp Gln Asp Leu
                165                 170                 175

Pro Tyr Gly Val Val Ser Ile Val Gly Met Pro Gly Leu Gly Lys Thr
            180                 185                 190

Thr Leu Ala Lys Lys Leu Tyr Arg His Val Arg Asp Gln Phe Glu Ser
        195                 200                 205

Ser Gly Leu Val Tyr Val Ser Gln Gln Pro Arg Ala Gly Glu Ile Leu
    210                 215                 220

Arg Asp Ile Ala Lys Gln Val Gly Leu Pro Lys Glu Glu Arg Lys Glu
225                 230                 235                 240

Asn Leu Glu Gly Asn Leu Arg Ser Leu Leu Lys Thr Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Glu Ile Gly Ser Arg Ile Ile Ile
        275                 280                 285

Thr Ser Arg Asn Ser Asn Val Gly Arg Tyr Ile Gly Gly Asp Phe Ser
    290                 295                 300

Ile His Met Leu Gln Pro Leu Asp Ser Glu Asn Ser Phe Glu Leu Phe
305                 310                 315                 320

Thr Lys Lys Ile Phe Thr Phe Asp Asn Asn Asn Asn Trp Ala Asn Ala
                325                 330                 335

Ser Pro Asp Leu Val Asp Ile Gly Arg Ser Ile Val Gly Arg Cys Gly
            340                 345                 350

Gly Ile Pro Leu Ala Ile Val Val Thr Ala Gly Met Leu Arg Ala Arg
        355                 360                 365

Glu Arg Thr Glu His Ala Trp Asn Arg Val Leu Glu Ser Met Gly His
    370                 375                 380

Lys Val Gln Asp Gly Cys Ala Lys Val Leu Ala Leu Ser Tyr Asn Asp
385                 390                 395                 400
```

```
Leu Pro Ile Ala Leu Arg Pro Cys Phe Leu Tyr Leu Gly Leu Phe Pro
            405                 410                 415

Glu Asp His Glu Ile Arg Ala Phe Asp Leu Thr Asn Met Trp Ile Ala
            420                 425                 430

Glu Lys Leu Ile Val Val Asn Ser Gly Asn Gly Arg Glu Ala Glu Ser
            435                 440                 445

Leu Ala Glu Asp Val Leu Asn Asp Phe Val Ser Arg Asn Leu Ile Gln
            450                 455                 460

Val Ser Gln Arg Lys Cys Asn Gly Arg Ile Ser Ser Tyr Arg Ile His
465                 470                 475                 480

Asp Leu Leu His Ser Leu Cys Val Glu Leu Gly Lys Glu Ser Asn Phe
                485                 490                 495

Phe His Thr Glu His Asn Ala Phe Gly Asp Pro Asp Asn Val Ala Arg
            500                 505                 510

Val Arg Arg Ile Thr Phe Tyr Ser Asp Asn Asn Ala Met Ser Lys Phe
            515                 520                 525

Phe Arg Ser Asn Pro Lys Pro Lys Lys Leu Arg Ala Leu Phe Cys Phe
            530                 535                 540

Thr Asn Leu Asp Ser Cys Ile Phe Ser His Leu Ala His His Asp Phe
545                 550                 555                 560

Lys Leu Leu Gln Val Leu Val Val Ile Ser Tyr Asn Trp Leu Ser
                565                 570                 575

Val Ser Ile Ser Asn Lys Phe Gly Lys Met Ser Cys Leu Arg Tyr Leu
            580                 585                 590

Arg Leu Glu Gly Pro Ile Val Gly Glu Leu Ser Asn Ser Ile Val Lys
            595                 600                 605

Leu Lys Arg Val Glu Thr Ile Asp Ile Ala Gly Asp Asn Ile Lys Ile
            610                 615                 620

Pro Cys Gly Val Trp Glu Ser Lys Gln Leu Arg His Leu Arg Asn Arg
625                 630                 635                 640

Glu Glu Arg Arg Tyr Phe Phe Ser Val Ser Pro Phe Cys Leu Asn Met
                645                 650                 655

Tyr Pro Leu Pro Pro Asn Asn Leu Gln Thr Leu Val Trp Met Asp Asp
            660                 665                 670

Lys Phe Phe Glu Pro Arg Leu Leu His Arg Leu Ile Asn Leu Arg Lys
            675                 680                 685

Leu Gly Ile Trp Gly Thr Ser Asp Ser Thr Ile Lys Ile Leu Ser Ala
            690                 695                 700

Leu Ser Pro Val Pro Thr Ala Leu Glu Val Leu Lys Leu Tyr Phe Leu
705                 710                 715                 720

Arg Asp Leu Ser Glu Gln Ile Asn Leu Ser Thr Tyr Pro Asn Ile Val
                725                 730                 735

Lys Leu Asn Leu Gln Gly Phe Val Arg Val Arg Leu Asn Ser Glu Ala
            740                 745                 750

Phe Pro Pro Asn Leu Val Lys Leu Ile Leu Asp Lys Ile Glu Val Glu
            755                 760                 765

Gly His Val Val Ala Val Leu Lys Lys Leu Pro Thr Leu Arg Ile Leu
            770                 775                 780

Lys Met Tyr Gly Cys Lys His Asn Glu Glu Lys Met Asp Leu Ser Gly
785                 790                 795                 800

Asp Gly Asp Gly Asp Ser Phe Pro Gln Leu Glu Val Leu His Ile Glu
                805                 810                 815

Arg Pro Phe Phe Leu Phe Glu Ile Thr Cys Thr Asp Asp Asp Ser Met
```

```
                     820                 825                 830
Pro Lys Leu Lys Lys Leu Leu Leu Thr Thr Ser Asn Val Arg Leu Ser
        835                 840                 845

Glu Arg Leu Ala Lys Leu Arg Val
    850                 855

<210> SEQ ID NO 14
<211> LENGTH: 861
<212> TYPE: PRT
<213> ORGANISM: Solanum lycopersicum

<400> SEQUENCE: 14

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Ala Gly Gly Asp Ser Arg Val Lys
    50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
        115                 120                 125

Asn Ile Ile Asp Thr Asp Asn Asn Asp Asp Cys Val Leu Leu Asp
    130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
        195                 200                 205

Ser Gly Leu Val Tyr Val Ser Gln Gln Pro Arg Ala Ser Glu Ile Leu
    210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Phe Leu Leu Asp Asp Ile Trp Asp Val Glu Ile Trp Asp Asp Leu Lys
            260                 265                 270

Leu Val Leu Pro Glu Cys Asp Ser Lys Val Gly Ser Arg Ile Ile Ile
        275                 280                 285

Thr Ser Arg Asn Ser Asn Val Gly Arg Tyr Ile Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
```

-continued

```
              340                 345                 350
Gly Ile Pro Leu Ala Ile Val Val Thr Ala Gly Met Leu Arg Ala Arg
            355                 360                 365

Glu Arg Thr Glu His Ala Trp Asn Arg Val Leu Glu Ser Met Gly His
370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
                    420                 425                 430

Glu Lys Phe Ile Val Val Asn Ser Gly Asn Arg Arg Glu Ala Glu Asp
                435                 440                 445

Leu Ala Glu Asp Val Leu Asn Asp Leu Val Ser Arg Asn Leu Ile Gln
                450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Glu Ser Asn Phe
                    485                 490                 495

Phe His Thr Ala His Asp Ala Phe Gly Asp Pro Gly Asn Val Ala Arg
                500                 505                 510

Leu Arg Arg Ile Thr Phe Tyr Ser Asp Asn Val Met Ile Glu Phe Phe
                515                 520                 525

Arg Ser Asn Pro Lys Leu Glu Lys Leu Arg Val Leu Phe Cys Phe Ala
530                 535                 540

Lys Asp Pro Ser Ile Phe Ser His Met Ala Tyr Phe Asp Phe Lys Leu
545                 550                 555                 560

Leu His Thr Leu Val Val Met Ser Gln Ser Phe Gln Ala Tyr Val
                    565                 570                 575

Thr Ile Pro Ser Lys Phe Gly Asn Met Thr Cys Leu Arg Tyr Leu Arg
                580                 585                 590

Leu Glu Gly Asn Ile Cys Gly Lys Leu Pro Asn Ser Ile Val Lys Leu
            595                 600                 605

Thr Arg Leu Glu Thr Ile Asp Ile Asp Arg Arg Ser Leu Ile Gln Pro
            610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
            660                 665                 670

Ile Pro Asp Lys Phe Phe Glu Pro Arg Leu Leu His Arg Leu Ile Asn
            675                 680                 685

Leu Arg Lys Leu Gly Ile Leu Gly Val Ser Asn Ser Thr Val Lys Met
            690                 695                 700

Leu Ser Ile Phe Ser Pro Val Leu Lys Ala Leu Glu Val Leu Lys Leu
705                 710                 715                 720

Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
                740                 745                 750

Ser Gln Ser Phe Pro Pro Asn Leu Ile Lys Leu Thr Leu Ala Asn Phe
            755                 760                 765
```

```
Thr Val Asp Arg Tyr Ile Leu Ala Val Leu Lys Thr Phe Pro Lys Leu
    770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Ser Glu Val Thr Cys Thr Asp Asp
                820                 825                 830

Val Ser Met Pro Lys Leu Lys Lys Leu Leu Leu Thr Gly Phe His Cys
                835                 840                 845

Arg Ile Ser Leu Ser Glu Arg Leu Lys Lys Leu Ser Lys
                850                 855                 860

<210> SEQ ID NO 15
<211> LENGTH: 861
<212> TYPE: PRT
<213> ORGANISM: Solanum lycopersicum

<400> SEQUENCE: 15

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
                20                  25                  30

Glu Asp Ile Asp Trp Leu Gln Arg Glu Met Arg His Ile Arg Ser Tyr
                35                  40                  45

Val Asp Asn Ala Lys Ala Lys Glu Ala Gly Gly Asp Ser Arg Val Lys
            50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
                100                 105                 110

Lys Ile Lys Arg Val Val Asp Ile Asp Arg Ile Arg Lys Thr Tyr Tyr
                115                 120                 125

Asn Ile Ile Asp Thr Asp Asn Asn Asp Asp Cys Val Leu Leu Asp
                130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
                180                 185                 190

Thr Leu Ala Lys Lys Leu Tyr Arg Leu Ile Arg Asp Gln Phe Glu Cys
                195                 200                 205

Ser Gly Leu Val Tyr Val Ser Gln Gln Pro Arg Ala Ser Glu Ile Leu
                210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Phe Leu Leu Asp Asp Val Trp Asp Val Glu Ile Trp Asp Asp Leu Lys
                260                 265                 270

Leu Val Leu Pro Glu Cys Asp Ser Lys Val Gly Ser Arg Ile Ile Ile
                275                 280                 285
```

-continued

```
Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Asn Ser Trp Ala Asn Ala
                325                 330                 335

Ser Pro Asp Leu Val Asn Ile Gly Arg Asn Ile Val Gly Arg Cys Gly
                340                 345                 350

Gly Ile Pro Leu Ala Ile Val Val Thr Ala Gly Met Leu Arg Ala Arg
            355                 360                 365

Glu Arg Thr Glu His Ala Trp Asn Arg Val Leu Glu Ser Met Gly His
    370                 375                 380

Lys Val Gln Asp Gly Cys Ala Lys Val Leu Ala Leu Ser Tyr Asn Asp
385                 390                 395                 400

Leu Pro Ile Ala Ser Arg Pro Cys Phe Leu Tyr Phe Gly Leu Tyr Pro
                405                 410                 415

Glu Asp His Glu Ile Arg Ala Phe Asp Leu Ile Asn Met Trp Ile Ala
                420                 425                 430

Glu Lys Phe Ile Val Val Asn Ser Gly Asn Arg Arg Glu Ala Glu Asp
            435                 440                 445

Leu Ala Glu Asp Val Leu Asn Asp Leu Val Ser Arg Asn Leu Ile Gln
450                 455                 460

Leu Ala Lys Arg Thr Tyr Asn Gly Arg Ile Ser Ser Cys Arg Ile His
465                 470                 475                 480

Asp Leu Leu His Ser Leu Cys Val Asp Leu Ala Lys Gly Ser Asn Phe
                485                 490                 495

Phe His Thr Ala His Asp Ala Phe Gly Asp Pro Gly Asn Val Ala Arg
                500                 505                 510

Leu Arg Arg Ile Thr Phe Tyr Ser Asp Asn Val Met Ile Glu Phe Phe
            515                 520                 525

Arg Ser Asn Pro Lys Leu Glu Lys Leu Arg Val Leu Phe Cys Phe Ala
    530                 535                 540

Lys Asp Pro Ser Ile Phe Ser His Met Ala Tyr Phe Asp Phe Lys Leu
545                 550                 555                 560

Leu His Thr Leu Val Val Met Ser Gln Ser Phe Gln Ala Tyr Val
                565                 570                 575

Thr Ile Pro Ser Lys Phe Gly Asn Met Thr Cys Leu Arg Tyr Leu Arg
                580                 585                 590

Leu Glu Gly Asn Ile Cys Gly Lys Leu Pro Asn Ser Ile Val Lys Leu
            595                 600                 605

Thr Arg Leu Glu Thr Ile Asp Ile Asp Arg Arg Ser Leu Ile Gln Pro
610                 615                 620

Pro Ser Gly Val Trp Glu Ser Lys His Leu Arg His Leu Cys Tyr Arg
625                 630                 635                 640

Asp Tyr Gly Gln Ala Cys Asn Ser Cys Phe Ser Ile Ser Ser Phe Tyr
                645                 650                 655

Pro Asn Ile Tyr Ser Leu His Pro Asn Asn Leu Gln Thr Leu Met Trp
                660                 665                 670

Ile Pro Asp Lys Phe Phe Glu Pro Arg Leu His Arg Leu Ile Asn
            675                 680                 685

Leu Arg Lys Leu Gly Ile Leu Gly Val Ser Asn Ser Thr Val Lys Met
    690                 695                 700

Leu Ser Ile Phe Ser Pro Val Leu Lys Ala Leu Glu Val Leu Lys Leu
705                 710                 715                 720
```

-continued

```
Ser Phe Ser Ser Asp Pro Ser Glu Gln Ile Lys Leu Ser Ser Tyr Pro
                725                 730                 735

His Ile Ala Lys Leu His Leu Asn Val Asn Arg Thr Met Ala Leu Asn
            740                 745                 750

Ser Gln Ser Phe Pro Pro Asn Leu Ile Lys Leu Thr Leu Ala Asn Phe
        755                 760                 765

Thr Val Asp Arg Tyr Ile Leu Ala Val Leu Lys Thr Phe Pro Lys Leu
    770                 775                 780

Arg Lys Leu Lys Met Phe Ile Cys Lys Tyr Asn Glu Glu Lys Met Ala
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Ser Glu Val Thr Cys Thr Asp Asp
            820                 825                 830

Val Ser Met Pro Lys Leu Lys Lys Leu Leu Thr Gly Phe His Cys
        835                 840                 845

Gly Ile Ser Leu Ser Glu Arg Leu Lys Lys Leu Ser Lys
    850                 855                 860

<210> SEQ ID NO 16
<211> LENGTH: 905
<212> TYPE: PRT
<213> ORGANISM: Solanum neorossii

<400> SEQUENCE: 16

Met Asn Tyr Cys Val Tyr Lys Thr Trp Ala Val Asp Ser Asn Thr Lys
1               5                   10                  15

Ala Asn Ser Thr Ser Phe Leu Ser Ser Phe Ser Tyr Phe Pro Phe Leu
            20                  25                  30

Ile Leu Thr Phe Arg Lys Lys Lys Phe Asn Glu Lys Leu Lys Glu Met
        35                  40                  45

Ala Glu Ile Leu Leu Thr Ala Val Ile Asn Lys Ser Ile Glu Ile Ala
    50                  55                  60

Gly Asn Val Leu Phe Gln Glu Gly Thr Arg Leu Tyr Trp Leu Lys Glu
65                  70                  75                  80

Asp Ile Asp Trp Leu Gln Arg Glu Met Arg His Ile Arg Ser Tyr Val
                85                  90                  95

Asp Asn Ala Lys Ala Lys Glu Val Gly Gly Asp Ser Arg Val Lys Asn
            100                 105                 110

Leu Leu Lys Asp Ile Gln Gln Leu Ala Gly Asp Val Glu Asp Leu Leu
        115                 120                 125

Asp Glu Phe Leu Pro Lys Ile Gln Gln Ser Asn Lys Phe Ile Cys Cys
    130                 135                 140

Leu Lys Thr Val Ser Phe Ala Asp Glu Phe Ala Met Glu Ile Glu Lys
145                 150                 155                 160

Ile Lys Arg Arg Val Ala Asp Ile Asp Arg Val Arg Thr Thr Tyr Ser
                165                 170                 175

Ile Thr Asp Thr Ser Asn Asn Asn Asp Asp Cys Ile Pro Leu Asp Arg
            180                 185                 190

Arg Arg Leu Phe Leu His Ala Asp Glu Thr Glu Val Ile Gly Leu Glu
        195                 200                 205

Asp Asp Phe Asn Thr Leu Gln Ala Lys Leu Leu Asp His Asp Leu Pro
    210                 215                 220

Tyr Gly Val Val Ser Ile Val Gly Met Pro Gly Leu Gly Lys Thr Thr
225                 230                 235                 240
```

-continued

```
Leu Ala Lys Lys Leu Tyr Arg His Val Cys His Gln Phe Glu Cys Ser
                245                 250                 255
Gly Leu Val Tyr Val Ser Gln Gln Pro Arg Ala Gly Glu Ile Leu His
            260                 265                 270
Asp Ile Ala Lys Gln Val Gly Leu Thr Glu Glu Arg Lys Glu Asn
        275                 280                 285
Leu Glu Asn Asn Leu Arg Ser Leu Leu Lys Ile Lys Arg Tyr Val Ile
    290                 295                 300
Leu Leu Asp Asp Ile Trp Asp Val Glu Ile Trp Asp Leu Lys Leu
305                 310                 315                 320
Val Leu Pro Glu Cys Asp Ser Lys Ile Gly Ser Arg Ile Ile Ile Thr
                325                 330                 335
Ser Arg Asn Ser Asn Val Gly Arg Tyr Ile Gly Gly Asp Phe Ser Ile
            340                 345                 350
His Val Leu Gln Pro Leu Asp Ser Glu Lys Ser Phe Glu Leu Phe Thr
        355                 360                 365
Lys Lys Ile Phe Asn Phe Val Asn Asp Asn Trp Ala Asn Ala Ser Pro
    370                 375                 380
Asp Leu Val Asn Ile Gly Arg Cys Ile Val Glu Arg Cys Gly Gly Ile
385                 390                 395                 400
Pro Leu Ala Ile Val Val Thr Ala Gly Met Leu Arg Ala Arg Gly Arg
                405                 410                 415
Thr Glu His Ala Trp Asn Arg Val Leu Glu Ser Met Ala His Lys Ile
            420                 425                 430
Gln Asp Gly Cys Gly Lys Val Leu Ala Leu Ser Tyr Asn Asp Leu Pro
        435                 440                 445
Ile Ala Leu Arg Pro Cys Phe Leu Tyr Phe Gly Leu Tyr Pro Glu Asp
    450                 455                 460
His Glu Ile Arg Ala Phe Asp Leu Thr Asn Met Trp Ile Ala Glu Lys
465                 470                 475                 480
Leu Ile Val Val Asn Thr Gly Asn Gly Arg Glu Ala Glu Ser Leu Ala
                485                 490                 495
Asp Asp Val Leu Asn Asp Leu Val Ser Arg Asn Leu Ile Gln Val Ala
            500                 505                 510
Lys Arg Thr Tyr Asp Gly Arg Ile Ser Ser Cys Arg Ile His Asp Leu
        515                 520                 525
Leu His Ser Leu Cys Val Asp Leu Ala Lys Glu Ser Asn Phe Phe His
    530                 535                 540
Thr Glu His Tyr Ala Phe Gly Asp Pro Ser Asn Val Ala Arg Val Arg
545                 550                 555                 560
Arg Ile Thr Phe Tyr Ser Asp Asp Asn Ala Met Asn Glu Phe His
                565                 570                 575
Leu Asn Pro Lys Pro Met Lys Leu Arg Ser Leu Phe Cys Phe Thr Lys
            580                 585                 590
Asp Arg Cys Ile Phe Ser Gln Met Ala His Leu Asn Phe Lys Leu Leu
        595                 600                 605
Gln Val Leu Val Val Met Ser Gln Lys Gly Tyr Gln His Val Thr
    610                 615                 620
Phe Pro Lys Lys Ile Gly Asn Met Ser Cys Leu Arg Tyr Val Arg Leu
625                 630                 635                 640
Glu Gly Ala Ile Arg Val Lys Leu Pro Asn Ser Ile Val Lys Leu Lys
                645                 650                 655
Cys Leu Glu Thr Leu Asp Ile Phe His Ser Ser Ser Lys Leu Pro Phe
```

-continued

```
                660                 665                 670
Gly Val Trp Glu Ser Lys Ile Leu Arg His Leu Cys Tyr Thr Glu Glu
            675                 680                 685
Cys Tyr Cys Val Ser Phe Ala Ser Pro Phe Cys Arg Ile Met Pro Pro
        690                 695                 700
Asn Asn Leu Gln Thr Leu Met Trp Val Asp Asp Lys Phe Cys Glu Pro
705                 710                 715                 720
Arg Leu Leu His Arg Leu Ile Asn Leu Arg Thr Leu Cys Ile Met Asp
                725                 730                 735
Val Ser Gly Ser Thr Ile Lys Ile Leu Ser Ala Leu Ser Pro Val Pro
            740                 745                 750
Lys Ala Leu Glu Val Leu Lys Leu Arg Phe Phe Lys Asn Thr Ser Glu
        755                 760                 765
Gln Ile Asn Leu Ser Ser His Pro Asn Ile Val Glu Leu Gly Leu Val
            770                 775                 780
Gly Phe Ser Ala Met Leu Leu Asn Ile Glu Ala Phe Pro Pro Asn Leu
785                 790                 795                 800
Val Lys Leu Asn Leu Val Gly Leu Met Val Asp Gly His Leu Leu Ala
                805                 810                 815
Val Leu Lys Lys Leu Pro Lys Leu Arg Ile Leu Ile Leu Leu Trp Cys
            820                 825                 830
Arg His Asp Ala Glu Lys Met Asp Leu Ser Gly Asp Ser Phe Pro Gln
        835                 840                 845
Leu Glu Val Leu Tyr Ile Glu Asp Ala Gln Gly Leu Ser Glu Val Thr
    850                 855                 860
Cys Met Asp Asp Met Ser Met Pro Lys Leu Lys Lys Leu Phe Leu Val
865                 870                 875                 880
Gln Gly Pro Asn Ile Ser Pro Ile Ser Leu Arg Val Ser Glu Arg Leu
                885                 890                 895
Ala Lys Leu Arg Ile Ser Gln Val Leu
            900                 905
```

<210> SEQ ID NO 17
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 17
agtgcaccaa gggtgtgac                                               19

<210> SEQ ID NO 18
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 18
aagtgcatgc ctgtaatggc                                              20

<210> SEQ ID NO 19
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 19

```
atgggcgctg catgtttcgt g                                    21

<210> SEQ ID NO 20
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 20
acacctttgt tgaaagccat ccc                                  23

<210> SEQ ID NO 21
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 21
tccccttggc attttcttct cc                                   22

<210> SEQ ID NO 22
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 22
tttagggtgg ggtgaggttg g                                    21

<210> SEQ ID NO 23
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 23
caactcaaac cagaaggcaa a                                    21

<210> SEQ ID NO 24
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 24
gagaaatggg cacaaaaaac a                                    21

<210> SEQ ID NO 25
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 25
tccttatatg gagcaagca                                       19

<210> SEQ ID NO 26
<211> LENGTH: 20
<212> TYPE: DNA
<213> ORGANISM: Artificial sequence
```

```
<220> FEATURE:
<223> OTHER INFORMATION: Synthetic sequence: Primer

<400> SEQUENCE: 26
ccagtagata agtcatccca                                                  20

<210> SEQ ID NO 27
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 27
attgaaagaa tacacaaaca tc                                               22

<210> SEQ ID NO 28
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 28
attcatgttc agatcgttta c                                                21

<210> SEQ ID NO 29
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 29
ttggtgcagc cgtatgacaa atcc                                             24

<210> SEQ ID NO 30
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 30
tccatcatta tttggcgtca tacc                                             24

<210> SEQ ID NO 31
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 31
tagatctata ctacacttgg cac                                              23

<210> SEQ ID NO 32
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 32
taatctcttc catcttccc                                                   19
```

```
<210> SEQ ID NO 33
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 33
acaaacctat gttagcctcc cacac                                          25

<210> SEQ ID NO 34
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 34
ggcatcaagc caatgtcgta aag                                            23

<210> SEQ ID NO 35
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 35
agcaggacac tcgattctct aataagc                                        27

<210> SEQ ID NO 36
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 36
tgcactaagt agtaatgccc aaagctc                                        27

<210> SEQ ID NO 37
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 37
ctgaggtgca gccaataac                                                 19

<210> SEQ ID NO 38
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 38
ccagtgagaa acagcttctc                                                20

<210> SEQ ID NO 39
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 39
```
gatgggcaac gatgttgttg                                            20

<210> SEQ ID NO 40
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 40
gcattagtac agcgtcttgg c                                          21

<210> SEQ ID NO 41
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 41
gtgaagaagg tctacagaaa gcag                                       24

<210> SEQ ID NO 42
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 42
gggcattaat gtagcaatca gc                                         22

<210> SEQ ID NO 43
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 43
catatcctgg aggtgttatg aatgc                                      25

<210> SEQ ID NO 44
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 44
catatcctgg aggtgttatg aatgc                                      25

<210> SEQ ID NO 45
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 45
cacggagact aagattcagg                                            20

<210> SEQ ID NO 46
<211> LENGTH: 20
<212> TYPE: DNA
<213> ORGANISM: Artificial sequence

```
<220> FEATURE:
<223> OTHER INFORMATION: Synthetic sequence: Primer

<400> SEQUENCE: 46
taaaggtgat gctgatgggg                                               20

<210> SEQ ID NO 47
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 47
catcaattga tgcctttgga cc                                            22

<210> SEQ ID NO 48
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 48
ctgcatcagc ttcttcctct gc                                            22

<210> SEQ ID NO 49
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 49
aatcgtgcag tttcagcata agcg                                          24

<210> SEQ ID NO 50
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 50
tgcttccagt tccgtgggat tc                                            22

<210> SEQ ID NO 51
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 51
catatggtga cgcctacag                                                19

<210> SEQ ID NO 52
<211> LENGTH: 18
<212> TYPE: DNA
<213> ORGANISM: Artificial sequence
<220> FEATURE:
<223> OTHER INFORMATION: Synthetic sequence: Primer

<400> SEQUENCE: 52
ggagacattg tcacaagg                                                 18
```

<210> SEQ ID NO 53
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 53
gttcgcgttc tcgttactgg                                        20

<210> SEQ ID NO 54
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 54
gttgcatggt tgacatcagg                                        20

<210> SEQ ID NO 55
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 55
ctgcaaatct actcgtgcaa g                                      21

<210> SEQ ID NO 56
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 56
ctcgtggatt gagaaatccc                                        20

<210> SEQ ID NO 57
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 57
cttactttcc cttcctcatc ctcac                                  25

<210> SEQ ID NO 58
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 58
tgaagtcatc ttccagaccg atg                                    23

<210> SEQ ID NO 59
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 59
agttatacac cctacattct actcg        25

<210> SEQ ID NO 60
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 60
ctttgaaaag aggcttcata ctccc        25

<210> SEQ ID NO 61
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 61
gtatgtttga gttagtcttc c        21

<210> SEQ ID NO 62
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 62
tataataggt gttcttgggg        20

<210> SEQ ID NO 63
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 63
aaggtgttgg gagtttttag        20

<210> SEQ ID NO 64
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 64
tatcttcctc attttggtgc        20

<210> SEQ ID NO 65
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 65
gattgagaca atgctagtcc        20

<210> SEQ ID NO 66
<211> LENGTH: 21
<212> TYPE: DNA
<213> ORGANISM: Artificial sequence

```
<220> FEATURE:
<223> OTHER INFORMATION: Synthetic sequence: Primer

<400> SEQUENCE: 66
agaagcagtc aatagtgatt g                                              21

<210> SEQ ID NO 67
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 67 aagattctttt ttcctcctta g                                             21

<210> SEQ ID NO 68
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 68
aaagatgaag tagagttttg g                                              21

<210> SEQ ID NO 69
<211> LENGTH: 48
<212> TYPE: DNA
<213> ORGANISM: Artificial sequence
<220> FEATURE:
<223> OTHER INFORMATION: Synthetic sequence: Blunt adapter

<400> SEQUENCE: 69
gtaatacgac tcactatagg gcacgcgtgg tcgacggccc gggctgga                 48

<210> SEQ ID NO 70
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 70
taatacgact cactataggg c                                              21

<210> SEQ ID NO 71
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 71
actatagggc acgcgtggt                                                 19

<210> SEQ ID NO 72
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 72
gaagttggag gcgattcaag g                                              21
```

```
<210> SEQ ID NO 73
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 73
ggcttgtagt gtattgaagt c                                          21

<210> SEQ ID NO 74
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 74
ccttcctcat cctcacattt ag                                         22

<210> SEQ ID NO 75
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 75
gcatgccaac tattgaaaca ac                                         22

<210> SEQ ID NO 76
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 76
cacggagact aagattcagg                                            20

<210> SEQ ID NO 77
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 77
taaaggtgat gctgatgggg                                            20

<210> SEQ ID NO 78
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 78
ccagaccacc aagtggttct c                                          21

<210> SEQ ID NO 79
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 79
```
aactttcaga tatgctctgc ag                                           22

<210> SEQ ID NO 80
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 80
aacggtgtac gagattttac                                              20

<210> SEQ ID NO 81
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 81
acctacatag atgaacctcc                                              20

<210> SEQ ID NO 82
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 82
ggatattatc ttgcaacatc tcg                                          23

<210> SEQ ID NO 83
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 83
cttctgatgg tatgcatgag aac                                          23

<210> SEQ ID NO 84
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 84
gcattagcgc aattggaatc cc                                           22

<210> SEQ ID NO 85
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 85
ggagagcatt agtacagcgt c                                            21

<210> SEQ ID NO 86
<211> LENGTH: 21
<212> TYPE: DNA
<213> ORGANISM: Artificial sequence

```
<220> FEATURE:
<223> OTHER INFORMATION: Synthetic sequence: Primer

<400> SEQUENCE: 86
tccaaatatt gtcgagttgg g                                              21

<210> SEQ ID NO 87
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 87
gctttggtgc agacatgatg c                                              21

<210> SEQ ID NO 88
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 88
ggttgtctga agtaacgtgc ac                                             22

<210> SEQ ID NO 89
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 89
tgcacggatg atgtcagtat gcc                                            23

<210> SEQ ID NO 90
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 90
caacttgaag ttttgcatat tc                                             22

<210> SEQ ID NO 91
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 91
atggctgaaa ttcttctcac agc                                            23

<210> SEQ ID NO 92
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 92
ttatagtacc tgtgatattc tcaac                                          25
```

```
<210> SEQ ID NO 93
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 93
atgaattatt gtgtttacaa gacttg                                          26

<210> SEQ ID NO 94
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 94
tgatattctc aactttgcaa gc                                              22

<210> SEQ ID NO 95
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 95
gaacactcaa attgatgaca gacatgcc                                        28

<210> SEQ ID NO 96
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 96
cccaaaccgg gcatgccaac tattg                                           25

<210> SEQ ID NO 97
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 97
aaggcaggaa caagatcagg                                                 20

<210> SEQ ID NO 98
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 98
ttgacagcag ctggaattg                                                  19

<210> SEQ ID NO 99
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 99
```
aattaaatgg aggggggtatc                                              20

<210> SEQ ID NO 100
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 100
cctttgaatg tctagtacca g                                             21

<210> SEQ ID NO 101
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 101
cagaagcagc tgactccaaa                                               20

<210> SEQ ID NO 102
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 102
ttcaacagtg agagagccac a                                             21

<210> SEQ ID NO 103
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 103
gcacaagcac agtctggaaa                                               20

<210> SEQ ID NO 104
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 104
gctgcattaa tagggcttgc                                               20

<210> SEQ ID NO 105
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 105
tactcgtgca agaaggaacg                                               20

<210> SEQ ID NO 106
<211> LENGTH: 21
<212> TYPE: DNA
<213> ORGANISM: Artificial sequence

```
<220> FEATURE:
<223> OTHER INFORMATION: Synthetic sequence: Primer

<400> SEQUENCE: 106
ccaacttgtt tggctatgtc a                                          21

<210> SEQ ID NO 107
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 107
gtggtctttt gaggcagagc                                            20

<210> SEQ ID NO 108
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 108
agattcgccg tctgtgaagt                                            20

<210> SEQ ID NO 109
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 109
tcttgccaag caggtctttt                                            20

<210> SEQ ID NO 110
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 110
cagccattag gcatttgaca                                            20

<210> SEQ ID NO 111
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 111
ctggtcctat agggttacca tt                                         22

<210> SEQ ID NO 112
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 112
agaaccgcac catcatttct tg                                         22
```

```
<210> SEQ ID NO 113
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 113
ccacttcacc cacctggtat                                               20

<210> SEQ ID NO 114
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 114
agctttgcag acattacatg g                                             21

<210> SEQ ID NO 115
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 115
agttatacac cctacattct actcg                                         25

<210> SEQ ID NO 116
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 116
ctttgaaaag aggcttcata ctccc                                         25
```